(12) United States Patent
Natori

(10) Patent No.: US 6,214,599 B1
(45) Date of Patent: Apr. 10, 2001

(54) PROTEASE

(75) Inventor: Shunji Natori, Ibaraki Pref. (JP)

(73) Assignee: University of Tokyo, Tokyo (JP)

( * ) Notice: Subject to any disclaimer, the term of this patent is extended or adjusted under 35 U.S.C. 154(b) by 0 days.

(21) Appl. No.: 09/515,039

(22) Filed: Mar. 6, 2000

Related U.S. Application Data

(62) Division of application No. 09/120,365, filed on Jul. 22, 1998.

(30) Foreign Application Priority Data

Nov. 18, 1997 (JP) ..................................... 9-333474

(51) Int. Cl.⁷ ............................... C12N 9/52; C12N 1/20; C12N 15/00; C07H 21/04

(52) U.S. Cl. ................... 435/220; 435/252.3; 435/320.1; 536/23.2

(58) Field of Search ................................. 435/220, 252.3, 435/320.1; 536/23.2

(56) References Cited

PUBLICATIONS

Eur. J. Biochem. 209, 939–944, 1992.*

* cited by examiner

*Primary Examiner*—Tekchand Saidha
(74) *Attorney, Agent, or Firm*—Venable; Marina V. Schneller

(57) ABSTRACT

The object of this invention is to provide a new cysteine protease. The object is achieved by providing a new cysteine protease which is obtained from a flesh fly (*Sarcophaga peregrina*) and comprises 26 kDa and 29 kDa subunits.

3 Claims, 25 Drawing Sheets

| | |
|---|---|
| 26KNterm | TNPPRWD |
| 26KE | TNPPRWDPNYIVK |
| 26KD | gTLYIPYAEIAEPFYAWxK |
| | a |
| 26KR3 | xNPxxWxPNYIVKgTLYIPYAEI |
| 26K1 | TNPPRWDPNYIVKgTLYIPYAEIAEPFYAWYxK |
| | |
| 26KA | VTALQLyGTsEDPVQVQAILpNAK |
| | |
| 26KB | NVYTLWVRYK |
| | |
| 26KC | xPHYPAsrMPIpVrYEM |
| 26KG | xPHYPAsRMPIIVrYEMr |
| | v |
| 26KR7 | MPIPVRYEMx |
| 26K2 | xPHYPAsRMPIPVrYEMr |
| | |
| 26KH | NTRRSRIDYYGGMVK |
| 26KF | xYQLANEHPFGTSLK |
| 26KR2 | xxxDYYGGMVKTYQLANEhPFG |
| 26K3 | NTRRSRIDYYGGMVKTYQLANEHPFGTSLK |
| | |
| 26KI | FRLEETIGDK |
| | |
| 26KJ | LIGTETFLGFNyDK |
| | a |
| 26KR5 | xYNTLLGSHYD |

FIG. 2

```
29KNterm      DTVPDQYDxRLYGAV

29KD          DTVPDQYDWrLYGAVTPVK

29KB1         xGwNTYWGNDQYILMSAWK
                 s

29KB2         NVsLVAPITGFFxVTPNDPMALK
                 w

29KE1         nGLdELDHAVLAVGYGTINGEDYWLVK
              d   v

29KE2         dqSvTGSxWxFGtIxHLegaFFLK
              n  d              vk

29KF          NNAGVMTMPTYVEM

29KJ          xMMEMGGVPTEEEYGPYLGQDGY
```

FIG. 3

```
26K1     T  N  P  P  R  W  D  P  N  Y  I  V  K  G  T  L  Y  I  P  Y  A  E  I  A  E  P  F  Y  A  W  Y  X  K
26K5'-1  5'AATCCACCCCGNTGGGATC 3'                              26K5'-3  5'GAGCCCTTTTATGCNTGTA 3'
            A       C                                                             C  C

26K5'-2  5'TGGGACCCCAATTATATTGT 3'                    26K3'-N  3'CTTGGNAAAATGCGGACCAT 5'
                       C  C  C                                                  C       G
                          A

26K3     N  T  R  R  S  R  I  D  Y  Y  G  G  M  V  K  T  Y  Q  L  A  N  E  H  P  F  G  T  S  L  K
                           26K3'-2  3'ATAATACCNCCGTACCACTT 5'  26K3'-1  3'TTACTTGTAGGNAAGCCGTG 5'
                                              G                              G  C  G

26KI     F  R  L  E  E  T  I  G  D  K
26K3'-I  3'CTTCTTGNTAACCGCTGTT 5'
              C  C        G
                          T
```

FIG. 4

```
   1 AAACACTACATTATTATTCATTCATTTTGAACAAAAAGAAGAGAATTATTTTATCATCATTTTGCAAAGTCATTAAAAGTAACAAAGAAG   90

91 ACTGCGAGGAGTGAAAGTGCATCAGGGATAAGGAAGAAAATGCGTTGCACATTGATTTTTGCAATTATTGCTGGCATTGCAATTACAGCT  180
                                    M  R  C  T  L  I  F  A  I  I  A  G  I  A  I  T  A
 181 TTGGCCACAAATCCACCACGCTGGGATCCCAACTATATAGTTAAGGGCACATTATATATTCCCTATGCGGAAATAGCTGAACCATTTTAT  270
      L  A  T  N  P  P  R  W  D  P  N  Y  I  V  K  G  T  L  Y  I  P  Y  A  E  I  A  E  P  F  Y
 271 GCCTGGTACGATAAGAATACACGACGTTCCCGTATTGATTACTATGGTGGCATGGTGAAAACCTATCAATTGGCAAATGAACATCCTTTT  360
      A  W  Y  D  K  N  T  R  R  S  R  I  D  Y  Y  G  G  M  V  K  T  Y  Q  L  A  N  E  H  P  F
 361 GGTACTTCTTTAAAATTGGCCCCCATTACCACTAAATCAGAGTTAAACAAAGTAACATGTCTTCAACTGAATGGCACTTCTGAAGATCCC  450
      G  T  S  L  K  L  A  P  I  T  T  K  S  E  L  N  K  V  T  C  L  Q  L  N  G  T  S  E  D  P
 451 GTACAAGTGCAAGCAATATTGCCAAATGCCAAGGACTTCAAACTTATAGGCACTGAAACCTTTTTAGGCTTCAACTGTGACAAATTCCGC  540
      V  Q  V  Q  A  I  L  P  N  A  K  D  F  K  L  I  G  T  E  T  F  L  G  F  N  C  D  K  F  R
 541 TTAGAGGAAACAATTGGCGATAAGAAAAATGTATACACTTTGTGGGTACGTTATAAGAAGTCACCCCATTATCCGGCTTCAAGAATGCCC  630
      L  E  E  T  I  G  D  K  K  N  V  Y  T  L  W  V  R  Y  K  K  S  P  H  Y  P  A  S  R  M  P
 631 ATACCAGTACGCTATGAAATGAGAGGTTACAATACCCTTTTGGGTTCCCATTATGATCACTATTATCTGGATTATGATAGTTACGATCAC  720
      I  P  V  R  Y  E  M  R  G  Y  N  T  L  L  G  S  H  Y  D  H  Y  Y  L  D  Y  D  S  Y  D  H
 721 GATGATATACCCAATGAAGTATTTGAATTGGATGATAACATGGAATGTATGCCTTTCCCTGGACCCGGCAAAGGTCATTATGCCACCTTC  810
      D  D  I  P  N  E  V  F  E  L  D  D  N  M  E  C  M  P  F  P  G  P  G  K  G  H  Y  A  T  F
 811 AATCCCATGCAAGAGTTTGTTCATCCCACTGTAGACCATCATGTGGAGCATGCCTTTAAACATTTCAAAAACAAGCATGGCATTGATTAT  900
      N  P  M  Q  E  F  V  H  P  T  V  D  H  H  V  E  H  A  F  K  H  F  K  N  K  H  G  I  D  Y
 901 CGCACCGAACAAGAGCATGAATATCGTAAAAACATCTTTAGACAAAATCTGAGATTTATTAATTCGAAAAATCGTGGCAAATTAAGTTAT  990
      R  T  E  Q  E  H  E  Y  R  K  N  I  F  R  Q  N  L  R  F  I  N  S  K  N  R  G  K  L  S  Y
 991 ACTCTTGCCATTAACCACTTGGCAGATAAAAGCGATGATGAACTAAAGGGTCGTCGAGGTTATAAATCATCGGGTGTCTTTAATACAGGC 1080
      T  L  A  I  N  H  L  A  D  K  S  D  D  E  L  K  G  R  R  G  Y  K  S  S  G  V  F  N  T  G
1081 AAACCATTCCCTTACAATTTGGAAAAGTACCGTGACACAGTGCCAGATCAATATGATTGGCGTTTGTATGGTGCCGTAACACCCGTTAAA 1170
      K  P  F  P  Y  N  L  E  K  Y  R  D  T  V  P  D  Q  Y  D  W  R  L  T  G  A  V  T  P  V  K
1171 GATCAATCTGTTTGCGGTTCTTGTTGGTCTTTTGGCACTATTGGCCATTTGGAGGGTGCATTTTTCCTTAAGAATGCGGCAATTTGGTA  1260
      D  Q  S  V  C  G  S  C  W  S  F  G  T  I  G  H  L  E  G  A  F  F  L  K  N  G  G  N  L  V
1261 CGCTTATCGCAACAAGCTTTAATCGATTGCTCTTGGGAGTATGGCAACAACGGTTGTGATGGTGGCGAAGATTTCCGTGCCTATAAATGG 1350
      R  L  S  Q  Q  A  L  I  D  C  S  W  E  Y  G  N  N  G  C  D  G  G  E  D  F  R  A  Y  K  W
1351 ATGATGGAAATGGGCGGTGTACCCACAGAAGAAGAATATGGTCCCTATTTAGGTCAAGATGGTTATTGTCATGCCAAAAATGTTAGTCTG 1440
      M  M  E  M  G  G  V  P  T  E  E  E  Y  G  P  Y  L  G  Q  D  G  Y  C  H  A  K  N  V  S  L
1441 GTGGCACCCATTACTGGCTTCTTTAATGTTACACCTAATGATCCTATGGCTTTAAAAATTGCCCTTTTAAAACATGGCCCCATATCGGTT 1530
      V  A  P  I  T  G  F  F  N  V  T  P  N  D  P  M  A  L  K  I  A  L  L  K  H  G  P  I  S  V
1531 GCTATTGATGCCTCACCCAAAACCTTTAGTTTCTATTCGCACGGTGTCTACTATGAACCTACCTGCAAGAATGGTCTTGATGAACTTGAT 1620
      A  I  D  A  S  P  K  T  F  S  F  Y  S  H  G  V  Y  Y  E  P  T  C  K  N  G  L  D  E  L  D
1621 CATGCTGTCTTGGCCGTGGGCTATGGCACAATCAACGGCGAAGATTACTGGCTGGTAAAGAATTCTTGGTCTACTTATTGGGGCAATGAT 1710
      H  A  V  L  A  V  G  Y  G  T  I  N  G  E  D  Y  W  L  V  K  N  S  W  S  T  T  W  G  N  D
1711 GGTTATATTTTAATGTCTGCCCCGTAAAAATAATTGCGGTGTTATGACCATGCCCACTTATGTAGAGATGTAAGCATATTGATGGTCTGCT 1800
      G  Y  I  L  M  S  A  R  K  N  N  C  G  V  M  T  M  P  T  Y  V  E  M  *
1801 TAAAGCTTTATAAAATGACTTTAATTTTCATTTAATTTTTCTTTAATTTTTTTTTTTATAAGTTGATCTACTAAAATAAGAAAGAAAATA 1890

1891 AAAATTGTTTAAATAAAAAAAAAA
```

FIG. 5

```
seq SA    5' TGGCCACAAATCCACCACGC  3'
seq SB    5' CAATTGGCAAATGAACATCC  3'
seq SC    5' CTCTTGCCATTAACCACTTG  3'
seq SD    5' GGCACTATTGGCCATTTGGAG 3'
seq SE    5' CCATATCGGTTGCTATTGATGC 3'
seq SF    5' ATGGCACAATCAACGGCGAAG 3'
seq AA    5' GCTTACATCTACATAAGTG   3'
seq AB    5' AGCCATAGGATCATTAGGTGT 3'
seq AC    5' GCTTGTTGCGATAAGCGTACC 3'
seq AD    5' CCAAGTGGTTAATGGCAAGAG 3'
seq AE    5' GATCGTAACTATCATAATCCAG 3'
seq AF    5' CTATAAGTTTGAAGTCCTTGGC 3'
seq AG    5' GCGTGGTGGATTTGTGGCCA  3'
```

FIG. 6

```
        10         20         30         40         50         60         70         80         90
AAACACTACATTATTATTCATTCATTTTGAACAAAAAGAAGAGAATTATTTTATCATCATTTTGCAAAGTCATTAAAAGTAACAAAGAAG
        100        110        120        130        140        150        160        170        180
ACTGCGAGGAGTGAAAGTGCATCAGGGATAAGGAAGAAAATGCGTTGCACATTGATTTTTGCAATTATTGCTGGCATTGCAATTACAGCT
                                         M  R  C  T  L  I  F  A  I  I  A  G  I  A  I  T  A
        190        200        210        220        230        240        250        260        270
TTGGCCACAAATCCACCACGCTGGGATCCCAACTATATAGTTAAGGGCACATTATATATTCCCTATGCGGAAATAGCTGAACCATTTTAT
 L  A  T  N  P  P  R  W  D  P  N  Y  I  V  K  G  T  L  Y  I  P  Y  A  E  I  A  P  F  Y

─── SEQ SA ──→
    ←────────── SEQ AG

─── RECOMB 26K5' ──→
        280        290        300        310        320        330        340        350        360
GCCTGGTACGATAAGAATACACGACGTTCCCGTATTGATTACTATGGTGGCATGGTGAAAACCTATCAATTGGCAAATGAACATCCTTTT
 A  W  Y  D  K  N  T  R  R  S  R  I  D  Y  Y  G  G  M  V  K  T  Y  Q  L  A  N  E  H  P  F
                                                                 SEQ SB ──────────────→

370        380        390        400        410        420        430        440        450
GGTACTTCTTTAAAATTGGCCCCCATTACCACTAAATCAGAGTTAAACAAAGTAACATGTCTTCAACTGAATGGCACTTCTGAAGATCCC
 G  T  S  L  K  L  A  P  I  T  T  K  S  E  L  N  K  V  T  C  L  Q  L  N  G  T  S  E  D  P
        460        470        480        490        500        510        520        530        540
GTACAAGTGCAAGCAATATTGCCAAATGCCAAGGACTTCAAACTTATAGGCACTGAAACCTTTTTAGGCTTCAACTGTGACAAATTCCGC
 V  Q  V  Q  A  I  L  P  N  A  K  D  F  K  L  I  G  T  E  T  F  L  G  F  N  C  D  K  F  R
                                 ←────────── SEQ AF 550        560        570        580        590        600        610        620        630
TTAGAGGAAACAATTGGCGATAAGAAAAATGTATACACTTTGTGGGTACGTTATAAGAAGTCACCCCATTATCCGGCTTCAAGAATGCCC
 L  E  E  T  I  G  D  K  K  N  V  Y  T  L  W  V  R  Y  K  K  S  P  H  Y  P  A  S  R  M  P 640        650        660        670        680        690        700        710        720
ATACCAGTACGCTATGAAATGAGAGGTTACAATACCCTTTTGGGTTCCCATTATGATCACTATTATCTGGATTATGATAGTTACGATCAC
 I  P  V  R  Y  E  M  R  G  Y  N  T  L  L  G  S  H  Y  D  H  Y  Y  L  D  Y  D  S  Y  D  H
                                                                         ←────────── SEQ AE 730        740        750        760        770        780        790        800        810
GATGATATACCCAATGAAGTATTTGAATTGGATGATAACATGGAATGTATGCCTTTCCCTGGACCCGGCAAAGGTCATTATGCCACCTTC
 D  D  I  P  N  E  V  F  E  L  D  D  N  M  E  C  M  P  F  P  G  P  G  K  G  H  Y  A  T  F 820        830        840        850        860        870        880        890        900
AATCCCATGCAAGAGTTTGTTCATCCCACTGTAGACCATCATGTGGAGCATGCCTTTAAACATTTCAAAAACAAGCATGGCATTGATTAT
 N  P  M  Q  E  F  V  H  P  T  V  D  H  H  V  E  H  A  F  K  H  F  K  N  K  H  G  I  D  Y 910        920        930        940        950        960        970        980        990
CGCACCGAACAAGAGCATGAATATCGTAAAAAACATCTTTAGACAAAATCTGAGATTTATTAATTCGAAAAATCGTGGCAAATTAAGTTAT
 R  T  E  Q  E  H  E  Y  R  K  N  I  F  R  Q  N  L  R  F  I  N  S  K  N  R  G  K  L  S  Y
```

FIG. 7

```
      1000      1010      1020      1030      1040      1050      1060      1070      1080
ACTCTTGCCATTAACCACTTGGCAGATAAAAGCGATGATGAACTAAAGGGTCGTCGAGGTTATAAATCATCGGGTGTCTTTAATACAGGC
 T  L  A  I  N  H  L  A  D  K  S  D  D  E  L  K  G  R  R  G  Y  K  S  S  G  V  F  N  T  G
─────────────►
SEQ SC
         ◄──────────── SEQ AD 1090      1100      1110      1120      1130      1140      1150      1160      1170
AAACCATTCCCTTACAATTTGGAAAAGTACCGTGACACAGTGCCAGATCAATATGATTGGCGTTTGTATGGTGCCGTAACACCCGTTAAA
 K  P  F  P  Y  N  L  E  K  Y  R  D  T  V  P  D  Q  Y  D  W  R  L  Y  G  A  V  T  P  V  K
                     RECOMB 29K5'────────────►

1180      1190      1200      1210      1220      1230      1240      1250      1260
GATCAATCTGTTTGCGGTTCTTGTTGGTCTTTTGGCACTATTGGCCATTTGGAGGGTGCATTTTTCCTTAAGAATGGCGGCAATTTGGTA
 D  Q  S  V  C  G  S  C  W  S  F  G  T  I  G  H  L  E  G  A  F  F  L  K  N  G  G  N  L  V
                   SEQ SD ────────────►                                              ◄──────

1270      1280      1290      1300      1310      1320      1330      1340      1350
CGCTTATCGCAACAAGCTTTAATCGATTGCTCTTGGGAGTATGGCAACAACGGTTGTGATGGTGGCGAAGATTTCCGTGCCTATAAATGG
 R  L  S  Q  Q  A  L  I  D  C  S  W  E  Y  G  N  N  G  C  D  G  G  E  D  F  R  A  Y  K  W
─────────────── SEQ AC 1360      1370      1380      1390      1400      1410      1420      1430      1440
ATGATGGAAATGGGCGGTGTACCCACAGAAGAAGAATATGGTCCCTATTTAGGTCAAGATGGTTATTGTCATGCCAAAAATGTTAGTCTG
 M  M  E  M  G  G  V  P  T  E  E  E  Y  G  P  Y  L  G  Q  D  G  Y  C  H  A  K  N  V  S  L 1450      1460      1470      1480      1490      1500      1510      1520      1530
GTGGCACCCATTACTGGCTTCTTTAATGTTACACCTAATGATCCTATGGCTTTAAAAATTGCCCTTTTAAAACATGGCCCCATATCGGTT
 V  A  P  I  T  G  F  F  N  V  T  P  N  D  P  M  A  L  K  I  A  L  L  K  H  G  P  I  S  V
                                    ◄──────────── SEQ AB                        SEQ SE ─────

1540      1550      1560      1570      1580      1590      1600      1610      1620
GCTATTGATGCCTCACCCAAAACCTTTAGTTTCTATTCGCACGGTGTCTACTATGAACCTACCTGCAAGAATGGTCTTGATGAACTTGAT
 A  I  D  A  S  P  K  T  F  S  F  Y  S  H  G  V  Y  Y  E  P  T  C  K  N  G  L  D  E  L  D
───────────►

1630      1640      1650      1660      1670      1680      1690      1700      1710
CATGCTGTCTTGGCCGTGGGCTATGGCACAATCAACGGCGAAGATTACTGGCTGGTAAAGAATTCTTGGTCTACTTATTGGGCAATGAT
 H  A  V  L  A  V  G  Y  G  T  I  N  G  E  D  Y  W  L  V  K  N  S  W  S  T  Y  W  G  N  D
        SEQ SF ────────────►

1720      1730      1740      1750      1760      1770      1780      1790      1800
GGTTATATTTTAATGTCTGCCCGTAAAAATAATTGCGGTGTTATGACCATGCCCACTTATGTAGAGATGTAAGCATATTGATGGTCTGCT
 G  Y  I  L  M  S  A  R  K  N  N  C  G  V  M  T  M  P  T  Y  V  E  M  *
                                                                        ◄──────────── SEQ AA
                                                                        ◄──────────── RECOMB 26,29K3'

1810      1820      1830      1840      1850      1860      1870      1880      1890
TAAAGCTTTATAAAATGACTTTAATTTTCATTTAATTTTTCTTTAATTTTTTTTTTTATAAGTTGATCTACTAAAATAAGAAAGAAAATA 1900      1910      1920
AAAATTGTTTAAATAAAAAAAAAAA
```

```
26,29K  MRCTLIFAIIAGIAITALATNPPRWDPNYIVKGTLYIPYAEIAEPFYAWYDKNTRRSRIDYYGGMVKTYQ
cath L  MR-TVLVALIALVALTQ-A-------------------------------------------------

26,29K  LANEHPFGTSLKLAPITTKSELNKVTCLQLNGTSEDPVQVQAILPNAKDFKLIGTETFLGFNCDKFRLEE
cath L  --------------------------------------------------------------------

26,29K  TIGDKKNVYTLWVRYKKSPHYPASRNPIPVRYEMRGYNTLLGSHYDHYYLDYDSYDHDDIPNEVFELDDN
cath L  --------------------------------------------------------------------

26,29K  MECMPFPGPGKGHYATFNPMQEFVHPTVDHHVEHAFKHFKNKHGIDYRTEQEHEYRKNIFRQNLRFINSK
cath L  ------------------------ISPLDLIKEEWHTYKLQHRKNYANEVEERFRMKIFNENRHKIAKH 26,29K  N-R---GKLSYILAINHLADKSDDELKG-RRGYKSSG--VF-N-TGKPFPYNLEKYRDTVPDQYDWRLYG
cath L  NQLFAQGKVSYKLGLNKYADMLHHEFKETMNGYNHTLRQLMRERTGLVGATYIPPAHVTVPKSVDWREHG 26,29K  AVTPVKDQSVCGSCWSFGTIGHLEGAFFIKNGGNIVRLSQQALIDCSWEYGNNGCDGGEDFRAYKWMMEM
cath L  AVIGVKDQGHCGSCWAFSSTGALEGQHFRK-AGVLVSLSEQNLVDCSTKYGNNGCNGGLMDNAFRYIKDN 26,29K  GGVPTEEEYGPYLGQDGYCHAKNVSLVAPITGFFNVTPNDPMALKIALLKHGPISVAIDASPKTFSFYSH
cath L  GGIDTEKSY-PYEGIDDSCHFNKATIGATDTGFVDIPEGDEEKMKKAVATMGPVSVAIDASHESFQIYSE 26,29K  GVYYEPTCKNGLDELDHAVLAVGYGTIN-GEDYWLVKNSWSTYWGNDGYILMSARK-NN--CGVMTMPTYVEM
cath L  GVYNEPECDE--QNLDHGVLVVGYGTDESGMDYWLVKNSWGTTWGEQGYIKM-ARNQNNQCGIATASSYPTV
```

FIG. 13

```
                        ↓
FLESH FLY  242  HCGIES A IAAGLPK  255
                       248
MOUSE      239  HCGIES E IVAGIPR  252
                       245
RAT        239  HCGIES E IVAGIPR  252
                       245
BOVINE     239  HCGIES E IVAGMPC  252
                       245
HUMAN      239  HCGIES E VVAGIPR  252
                       245
CHICKEN    240  HCGIES E IVAGVPR  253
                       246
TOBACCO    236  ECEIED E VVAGLPS  249
                       242
```

FIG. 17

```
FLESH FLY  : TGCGGTTCTT GTTGGTCTTT TGGCACTATT GGCCATTTGG AGGGTGCATT TTTCCTTAAG AATGGCGGCA ATTTGGTACG CTTATCGCAA CAAGCTTTAA
FRUIT FLY  : TCGCCATCGT GCTGGTCATT TGGCACCATT GGTCACCTGG AGGGCGCCTT CTTCCTGAAG AATGGCGGCA ATCTGGTCCG GCTTTCCCAG CAGGCGTTGA
COCKROACH  : TGCGGCTCTT GTTGGAGTTT TGGGACTACT GGCACCATCG AAGGAGCTTA TTTCTTGAAG TATGGA---C ATTTGGTGCG ATTGTCACNA CAGGCTCTAA

FLESH FLY  : TCGATTGCTC TTGGGAGTAT GGCAACAACG GTTGTGATGG TGGCGAAGAT TTCCGTGCCT ATAAATGGAT GATGGAAATG GGCGGTGTAC CCACAGAAGA
FRUIT FLY  : TTGACTGCTC GTGGGCCTAT GGCAACAATG GCTGCGATGG TGGCGAGGAT TTCCGCGGTG TACCAGTGGAT GCTGCAGTCC GGCGGAGTGC CCACGGAGGA
COCKROACH  : TTGACTGCAG CTGGGGCTAT GGTAACAATG GTTGTGATGG AGGTGAAGAT TCCCGCTCTT ATGAATGGAT GATGAAGCAT GGTGGCATCC CACTGGAAGA

FLESH FLY  : AGAATATGGT CCCTATTTAG GTCAAGATGG TTATTGTCAT GCCAAAAATG TTAGTCTGGT GGCACCCATT ACTGGCTTCT TTAATGTTAC ACCTAATGAT
FRUIT FLY  : GGAGTACGGT CCCTATCTGG GCCAGGATGG CTACTGTCAC GTGAACAACG TGACCCTGGT GGCACCCATT AAGGGATTCG TCAATGTGAC CTCCAACGAT
COCKROACH  : CGAATATGGA GGCTATTTGG GCCAGGATGG CTATTGTCAT GTCGAAAATG TAACTCTCAC AGCAAAGATC ACTGGCTATG TGAACGTCAC ATCTGGAGAC

FLESH FLY  : CCTATGGCTT TAAAAATTGC CCTTTTAAAA CATGGCCCCA TATCGGTTGC TATTGATGCC CCTTTAGTTT CTATTCGCAC GGTGTCTACT
FRUIT FLY  : CCGAATGCCT TCAAGCTGGC TTTGCTCAAG CACGGTCCTC TGTCGGTGGC CATTGATGCT TCTCCCAAGA CATTTAGCTT CTACTGCGAC GGAGTTTACT
COCKROACH  : ATTGATGXXX XXXXXXXXXX XXXXXXXXXX XXXXXXXXXX XXXXXXXXXX XXXXXXXXXX XXXXXXXXXX XXXXXXXXXX XXXXXXXXXX XXXXXXXXXX

FLESH FLY  : ATGAACCTAC CTGCAAGAAT GGTCTTGATG AACTTGATCA TGCTGTCTTG GCCGTGGGCT ATGGCACAAT CAACGGCGAA GATTACTGGC TGGTAAAGAA
FRUIT FLY  : ATGAGCCAAC CTGCAAGAAC GATGTAAATG GACTGGATCA TGCTGTCTTG GCCGTGGGCG GGGGCTCAGT CAATGGACAA GACTATTGGC TGGTAAAAAA
COCKROACH  : XXXXXXXXXX XXXXXXXXXX XXXXXXXXXX XXXXXXXXXX XXXXXXXXXX XXXXXXXXXX XXXXXXXXXX XXXXXXXXXX XXXXXXXXXX XXXXXXXXXX

FLESH FLY  : TTCTTGGTCT ACTTATTGGG GCAATGATGG TTATATTTA ATGTCTGCCC GTAAAAATAA TTGCGGTGTT ATGACCATGC CCACTTATGT AGAGATGTAA
FRUIT FLY  : CCCCNGGTCC ACCTACTGGG GCAACGATGG CTACATCCTG ATGTTCGGGC AAAAAAACAA TTGCGGTGTT ATGACCATGC CCACTTATGT GGANATGTAA
COCKROACH  : XXXXXXXXXX XXXXXXXXXX XXXXXXXXXX XXXXXXXXXX XXXXXXXXXX XXXXXXXXXX XXXXXXXXXX XXXXXXXXXX XXXXXXXXXX XXXXXXXXXX

FLESH FLY  : GCATATTGAT GGTCTGCTTA AGCTTTATA AATGACTTT AATTTTCATT TAATTTTCT TAATTTTT TTTTTATAAG TTGATCTACT AAAATAAGAA

FLESH FLY  : AGAAAATAAA AATTGTTTAA ATAAAAAAAA AAAA
```

FIG. 21

```
FLESH FLY  : CTTCAAACTT ATAGGCACTG AAACCTTTTT AGCCTTCAAC TGTGACAAAT TCCGCTTAGA GGAAACAATT GGGGATAAGA AAAATGTATA CACTTTGTGG
FRUIT FLY  : TTTCAGCCTG GTGGGCACCG AATCCTTTTT GGGCTACACG TGCGACAAGT TCCGCCTGGA GTCGACAATT GGCCAAAAGA AAAACATCTA TACGCTGTTG
COCKROACH  : ATTCAAGTTG ATTGGTACAG AACCAATAAA TGCCCTGAAT TGCGAAAAAT GGCGTTTGGT GGACACAAAG GGAGCCAAGG TCAACAAATA CACAATGTGG

FLESH FLY  : GTACGTTATA AGAAGTCACC CCATTATCCG GCTTCAAGAA TGCCCATACC AGTACGCTAT GAAATGAGAG GTTACAATAC CCTTTTGGGT TCCCATTATG
FRUIT FLY  : GTxxxxxxxx xxxxxxxxxx xxxxxxxxxx xxxxxxxxxx xxxxxxxxxx xxxxxxxxxx xxxxxxxxxx xxxxxxxxxx xxxxxxxxxx xxxxxxxxxx
COCKROACH  : ATTCGGTACA AGAATCTGCA AATGATCCTG GTGTTAAAAA TCGCCATCCC AGTTCGATAC GAAATGAAGG GTTACNACTC TTTGCTGGGT TCTCATTATG FLESH FLY  : ATCACTATTA TCTGGATTAT GATAGTTACG ATCACGATGA TATACCCAAT GAAGTATTTG AATTGGATGA TAACATGGAA TGTATGCCTT TCCCTGACC
FRUIT FLY  : XXXXXXXXXX XTTGGACTAT GACAGCTACG TATTCCCAAC GAGGTGTTCG AGATCGATGA CAGCCTGCAG TGCCTGGAT TCCCGGACC
COCKROACH  : ACCACTACTA CCTGGAGTAC CAT------T GTTGCTTTCA GAAACCTGAT CCAGTGTTTT CCAAGTTGAA AGCAATTGAC ATGCACCAGC TTCCCAGTCC FLESH FLY  : CGGCAAAGGT CATTATGCCA CCTTCAATCC CATGCAAGAG CCATCATGTG GAGCATGCCT TTAAACATTT CAAAAACAAG
FRUIT FLY  : CGGCACCGGT CCTTCAATCC CATGCAGGAG TTCCGTCAG GAACC---GA TGAGCATGTG GACAAGCCT TCCACCACTT CAAGCGCAAG
COCKROACH  : AGGAGACAGA CATATTACA CATTTAACCC TATGAAGGAG TTCATTCATA ATTAT---GA CGAACATGTA GAAACCGCAT TTGATCACTT CCGAAAAAGA FLESH FLY  : CATGGCATTG ATTATGCCAC CGAACAAGAG CATGAATATC GTAAAAACAT CTTTAGACAA AATCTGAGAT TTATTAATTC GAAAAATCGT GGCAAATTAA
FRUIT FLY  : CACGGAGTTG CTTATCACAG CGAACGGAA GCAAGACATC AACCTGCCT ACATCCACTC CAAGAACCGG GCCGAACTCA
COCKROACH  : CACACAAGG ANTACGCCAG CAATTGGAA CACACAAGA GAAAAGAAT TTTCCGACAG AATTTGAGGT TCATCCATTC TAAGAATCGT GCTAGATTAG FLESH FLY  : GTTATACTCT TGCCATTAAC CACTTGGCAG ATAAAAGCCGA TGATGAACTA AAGGGTCGTC GAGGTTATAA ATCATCGGGT GTCTTTAATA CAGGCAAACC
FRUIT FLY  : CTTACACTTT GGCCGTTAAT CACTTGGCCG ACAAGACCGA AGAGGAGTTG AAGGCACGAC GCGATACAA ATCATCGGGC ATCTACACA CCGGCAAACC
COCKROACH  : GATTCACTCT GGACGTGAAC CATTTGGTGG CACACAAGA GCTCGAACTG AAAGTCTGA GGGGAAGCA ATACACTGAC GGTACAATG GAGGTTCTCC FLESH FLY  : ATTCCCTTAC AAT---TTGG AAAAGTACCG TGACACAGTG CCAGATCAAT ATGATTGGCG TTTGTATGGT GCCGTAACAC CCGTTAAAGA TCAATCTGTT
FRUIT FLY  : GTTCCCCTAT GAT---GTGC CCAAGTACAA GGACGAGATT CCCGACCAGT ACGACGAGGC CGTGTCACTC GGTGAAAGA TCAATCTGTG
COCKROACH  : ATTTCCTTAT ACCAATCTTG ACGCAATCAT GGACCAAATT CCTGATGATT TGGACTGGAG AATTTATGGT GCTGTGACTC CAGTTAAAGA TCAGTCTGTT
```

FIG. 22

```
FLESH FLY  :                AAACACT ACATTATTAT TCATTCATTT TGAACAAAAA GAAGAGAATT ATTTTATCAT CATTTTGCAA AGTCATTAAA AGTAACAAAG AAGACTGCGA
FRUIT FLY  :                                                                  GAANAA ACTGTTNTTT CGAAAAGATA GGTANTATAG TNGAGTCGGG ATCAGTTCAT
COCKROACH  :                                          GTTTG TGGGGTGCAC AGTNNACTTA CAGGGAAAGG GCCAATTTNT GTATCGGTAC TTTTGCTGTT

FLESH FLY  : GGAGTGAAAG TGCATCAGGG ATAAGGAAGA AAATGCGTTG CACATTGATT TTT------- ------GCAAT TATTGCTGGC ATTGCAATTA CAGCTTTGGC
FRUIT FLY  : ATTCCAGACA ATTCTCTGGT GAATTCTCAA GAATGCAAGT GTTTTTAGCT TTA------- ------GCCCT GCTCGCAGGC TTGGCTTTCT CAGCTAATGC
COCKROACH  : CCTGATTTCG AGAACTTCAG CTGAAGCATT ACATGGCTTG GAATCTTTTA TTTTCGGCGG TGTTGGCCAT CGCTTTTGTG TCTGTGCTGG GTGCAGATCC

FLESH FLY  : CACAAATCCA CCACGCTGGG ATCCCAACTA TATAGTTAAG GGCACATTAT TGCGGAAATA GCTGAACCAT TTTATGCCTG GTACGATAAG
FRUIT FLY  : CACGAATCCG CGGAAATGGG ATCCAAACTA CATAGTCAAA GGAACCCTGT ACATTCCGTA CGCCGAGATT GCCGAACCCT TCTACGCCTG GTATGACAAG
COCKROACH  : AACACCACCG AACTTC---A GTGATACTTA TACAGTAAAG GGAACACTTT ACATTCCATA TGCAGAGATT CGTGAGCCTT TCTTAGCGTA TTACGACTTG

FLESH FLY  : AATACACGAC GTTCCCGTAT TGATTACTAT GGTGGCATGG TGAAAACCTA TCAATTGGCA AATGAACATC CTTTTGGTAC TTGGCCCCCA
FRUIT FLY  : AATACGAGGC GATCCCGCAT CGATTACTAC GGCGGAATGG TGAAGACATA CCAACTGGCT GGCGAGGGTC AGTACGGAAC CCTGCTGAAG CTGGCACCGA
COCKROACH  : ACTGTTGGGT CTAGCCGCAT TGATTACTAT GGAGGAATGG TGAAAACGTA TCAAATCAGC TCAAATGGCA AGTATGGAAC AATTTCGAAC AAGTTTAAAG GTTGCACCTG

FLESH FLY  : TTACCACTAA ATCAGAGTTA AACAAAGTAA CATGTCTTCA ACTGAATGGC ACTTCTGAAG ATCCCGTACA AGTGCAAGCA ATATTGCCAA ATGCCAAGGA
FRUIT FLY  : TTACCACCAA GACGGAGAAC AACAAGCTAA CCTGTCTGCA GGTGAATGGC ACCGCCGACC AGGCTGTGCA TATTCAGAGC ATCCTGCCCG ATGCGAAACC
COCKROACH  : TGACAACAGA GAAAGTAGAG AATAAGGAAA CTTGCCTACA ACCACAGGA ACCAAAGACA ACCAAAATCGA AGTCAACGGA ACCACAGAGT ATTCTTCCAG ACTTAACAGG
```

FIG. 23

```
FLESH FLY         MRCT LIF---AII AGIAITALAT NPPRWDPNYI VKGTLYIPYA EIAEPFYAWY DKNTRRSRID YYGGMVKTYQ LANEHPFGTS LKLAPITTKS
FRUIT FLY         MQVF LAL---ALL AGLAFSANAT NPRKWDPNYI VKGTLYIPYA EIAEPFYAWY DKNTRRSRID YYGGMVKTYQ LAGEGQYGTL LKLAPITTKT
COCKROACH         MAWN LLFSAVLAIA FVSVLGADPT -PPNFSDTYT VKGTLYIPYA EIREPFLAYY DLTVGSSRID YYGGMVKTYQ ISKYGNFGTS LKVAPVTTEK

FLESH FLY   ELNKVTCLQL NGTSEDPVQV QAILPNAKDF KLIGTETFLG FNCDKFRLEE TIGDKKNVYT LWVRYKKSPH YPASRMPIPV RYEMRGYNTL LGSHYDHYL
FRUIT FLY   ENNKLITCLQV NGTADQAVDI QSILPDAKPF SLVGTESFLG YTCDKFRLES TIGQKKNIYT LXXXXXXXXX XXXXXXXXXX XXLHLGAIYL
COCKROACH   VENKETCLQV NGTKDNKIEP QSILPDLTGF KLIGTEPING LNCEKWRLVD TKGAKVNKYT MWIRYKNLQM ILVLKIAIPV RYEMKGYxSL LGSHYDHYL

FLESH FLY   DYDSYDHDDI PNEVFELDDN MECMPFPGPG KGHYATFNPM QEFVHPTVDH HVEHAFKHFK NKHGIDYRTE QEHEYRKNIF RQNLRFINSK NRGKLSYTLA
FRUIT FLY   DYDSYEHDDI PNEVFEIDDS LQCVGFPGPG TGHYATFNPM QEFISGT-DE HVDKAFHHFK RKHGVAYHSD TEHEHRKNIF RQNLRYIHSK NRAELTYTLA
COCKROACH   EYD--CCFQK PDPVFSKLKA IDMHQLPSPG DRHIYTFNPM KEFIHNY-DE HVETAFDHFR KRHSKxYSAN LEHTKRKEIF RQNLRFIHSK NRARLGFTLD

FLESH FLY   INHLADKSDD ELKGRRGYKS SGVFNTGKPF PY-NLEKYRDT VPDQYDWRLY GAVTPVKDQS VCGSCWSFGT IGHLEGAFFL KNGGNLVRLS QQALIDCSWE
FRUIT FLY   VNHLADKTEE ELKARRGYKS SGIYNTGKPF PYD-VPKYKDE IPDQYDWRLY GAVTPVKDQS VCGSCWSFGT IGHLEGAFFL KNGGNLVRLS QQALIDCSWA
COCKROACH   VNHLVDRTEL ELKALRGKQY TDGYNGGSPF PYTNLDIAMDQ IPDDLDWRIY GAVTPVKDQS VCGSCWSFGT TGTIEGAYFL KYG-HLVRLS xQALIDCSWG

FLESH FLY   YGNNGCDGGE DFRAYKWMME MGGVPTEEEY GPYLGQDGYC HAKNVSLVAP ITGFFNVTPN DPMALKIALL KHGPISVAID ASPKTFSFYS HGVYYEPTCK
FRUIT FLY   YGNNGCDGGE DFRVYQWMLQ SGGVPTEEEY GPYLGQDGYC HVNNVTLVAP IKGFVNVTSN DPNAFKLALL KHGPLSVAID ASPKTFSFYS HGVYYEPTCK
COCKROACH   YGNNGCDGGE DFRSYEWMMK HGGIPLEDEY GGYLGQDGYC HVENVTLTAK ITGYVNVTSG DIDAxxxxxx xxxxxxxxxx xxxxxxxxxx xxxxxxxxxx FLESH FLY   NGLDELDHAV LAVGYGTING EDYWLVKNSW STYWGNDGYI LMSARKNNCG VMTMPTYVEM
FRUIT FLY   NDVNGLDHAV LAVGYGSVNG EDYWLVKNSW STYWGNDGYI LMFGQKNNCG VMTMPTYVEM
COCKROACH   xxxxxxxxxx xxxxxxxxxx xxxxxxxxxx xxxxxxxxxx xxxxxxxxxx xxxxxxxxxx
```

FIG. 24

| | | | |
|---|---|---|---|
| 26kDa | FLESH FLY | PNYIVKGTLYIPYAEIAEPFYAWYDKNTRRSRIDYYGGMVKTYQLANEHPFGTSLKLAPITTKSELN |
| 26kDa | FRUIT FLY | PNYIVKGTLYIPYAEIAEPFYAWYDKNTRRSRIDYYGGMVKTYQLAGEGQYGTLLKLAPITTKTENN |
| 26kDa | COCKROACH | DTYTVKGTLYIPYAEIREPFLAYYDLTVGSSRIDYYGGMVKTYQISKYGNFGTSLKVAPVTTEKVEN |
| CALPAIN | HUMAN | GNEFWSALLEKAYAKVNGSYEALSGGSTSEGFEDFTGGVTEWYELRKAPSDLYQIILKALERGSLLG |
| CALPAIN | RAT | RNEFWSALLEKAYAKLHGSYEALKGGNTTEAMEDFTGGVTEFFEIKDAPSDMYKIMRKAIERGSLMG |
| CALPAIN | CHICKEN | CTEFWSALLEKAYAKLNGCYESLSGGSTTEGFEDFTGGVAEMYDLKRAPRNMGHIIRKALERGSLLG |
| CALPAIN | FRUIT FLY | KNEFWSALLEKAYAKLHGSYEALKGGSTCEAMEDFTGGVSEWYDLKEAPGNLFTILQKAAERNSMMG |
| CALPAIN | NEMATODE | NNEFWSALLEKAYAKLFGSYEALKGGTTSEALEDMTGGLTEFIDLKNPPRNLMQMMRGFEMGSLFG |
| CALPAIN | FLUKE | PTEFWSALLEKAYAKLNGCYAHLSGGSQSEAMEDLTGGICLSLELNQKERPSDLIDQLKIYAQRCCL |

FIG. 25

SEQUENCE LISTING

```
<160> NUMBER OF SEQ ID NOS: 101

<210> SEQ ID NO 1
<211> LENGTH: 550
<212> TYPE: PRT
<213> ORGANISM: Sarcophaga peregrina

<400> SEQUENCE: 1

Met  Arg  Cys  Thr  Leu  Ile  Phe  Ala  Ile  Ile  Ala  Gly  Ile  Ala  Ile  Thr
  1              5                  10                  15

Ala  Leu  Ala  Thr  Asn  Pro  Pro  Arg  Trp  Asp  Pro  Asn  Tyr  Ile  Val  Lys
            20                  25                  30

Gly  Thr  Leu  Tyr  Ile  Pro  Tyr  Ala  Glu  Ile  Ala  Glu  Pro  Phe  Tyr  Ala
            35                  40                  45

Trp  Tyr  Asp  Lys  Asn  Thr  Arg  Arg  Ser  Arg  Ile  Asp  Tyr  Tyr  Gly  Gly
     50                  55                  60

Met  Val  Lys  Thr  Tyr  Gln  Leu  Ala  Asn  Glu  His  Pro  Phe  Gly  Thr  Ser
 65                  70                  75                  80

Leu  Lys  Leu  Ala  Pro  Ile  Thr  Thr  Lys  Ser  Glu  Leu  Asn  Lys  Val  Thr
                85                  90                  95

Cys  Leu  Gln  Leu  Asn  Gly  Thr  Ser  Glu  Asp  Pro  Val  Gln  Val  Gln  Ala
               100                 105                 110

Ile  Leu  Pro  Asn  Ala  Lys  Asp  Phe  Lys  Leu  Ile  Gly  Thr  Glu  Thr  Phe
               115                 120                 125

Leu  Gly  Phe  Asn  Cys  Asp  Lys  Phe  Arg  Leu  Glu  Glu  Thr  Ile  Gly  Asp
          130                 135                 140

Lys  Lys  Asn  Val  Tyr  Thr  Leu  Trp  Val  Arg  Tyr  Lys  Lys  Ser  Pro  His
145                 150                 155                 160

Tyr  Pro  Ala  Ser  Arg  Met  Pro  Ile  Pro  Val  Arg  Tyr  Glu  Met  Arg  Gly
                    165                 170                 175

Tyr  Asn  Thr  Leu  Leu  Gly  Ser  His  Tyr  Asp  His  Tyr  Tyr  Leu  Asp  Tyr
               180                 185                 190

Asp  Ser  Tyr  Asp  His  Asp  Asp  Ile  Pro  Asn  Glu  Val  Phe  Glu  Leu  Asp
          195                 200                 205

Asp  Asn  Met  Glu  Cys  Met  Pro  Phe  Pro  Gly  Pro  Gly  Lys  Gly  His  Tyr
     210                 215                 220

Ala  Thr  Phe  Asn  Pro  Met  Gln  Glu  Phe  Val  His  Pro  Thr  Val  Asp  His
225                 230                 235                 240

His  Val  Glu  His  Ala  Phe  Lys  His  Phe  Lys  Asn  Lys  His  Gly  Ile  Asp
```

```
                   245                250                255

Tyr Arg Thr Glu Gln Glu His Glu Tyr Arg Lys Asn Ile Phe Arg Gln
            260                265                270

Asn Leu Arg Phe Ile Asn Ser Lys Asn Arg Gly Lys Leu Ser Tyr Thr
        275                280                285

Leu Ala Ile Asn His Leu Ala Asp Lys Ser Asp Glu Leu Lys Gly
    290                295                300

Arg Arg Gly Tyr Lys Ser Ser Val Phe Asn Thr Gly Lys Pro Phe
305                310                315                320

Pro Tyr Asn Leu Glu Lys Tyr Arg Asp Thr Val Pro Asp Gln Tyr Asp
                325                330                335

Trp Arg Leu Tyr Gly Ala Val Thr Pro Val Lys Asp Gln Ser Val Cys
            340                345                350

Gly Ser Cys Trp Ser Phe Gly Thr Ile Gly His Leu Glu Gly Ala Phe
        355                360                365

Phe Leu Lys Asn Gly Gly Asn Leu Val Arg Leu Ser Gln Gln Ala Leu
    370                375                380

Ile Asp Cys Ser Trp Glu Tyr Gly Asn Asn Gly Cys Asp Gly Gly Glu
385                390                395                400

Asp Phe Arg Ala Tyr Lys Trp Met Met Glu Met Gly Gly Val Pro Thr
                405                410                415

Glu Glu Glu Tyr Gly Pro Tyr Leu Gly Gln Asp Gly Tyr Cys His Ala
            420                425                430

Lys Asn Val Ser Leu Val Ala Pro Ile Thr Gly Phe Phe Asn Val Thr
        435                440                445

Pro Asn Asp Pro Met Ala Leu Lys Ile Ala Leu Leu Lys His Gly Pro
    450                455                460

Ile Ser Val Ala Ile Asp Ala Ser Pro Lys Thr Phe Ser Phe Tyr Ser
465                470                475                480

His Gly Val Tyr Tyr Glu Pro Thr Cys Lys Asn Gly Leu Asp Glu Leu
                485                490                495

Asp His Ala Val Leu Ala Val Gly Tyr Gly Thr Ile Asn Gly Glu Asp
            500                505                510

Tyr Trp Leu Val Lys Asn Ser Trp Ser Thr Tyr Trp Gly Asn Asp Gly
        515                520                525

Tyr Ile Leu Met Ser Ala Arg Lys Asn Asn Cys Gly Val Met Thr Met
    530                535                540

Pro Thr Tyr Val Glu Met
545                550

<210> SEQ ID NO 2
<211> LENGTH: 1915
<212> TYPE: DNA
<213> ORGANISM: Sarcophaga peregrina
<220> FEATURE:
<221> NAME/KEY: CDS
<222> LOCATION: (130)..(1779)

<400> SEQUENCE: 2
aaacactaca ttattattca ttcattttga acaaaaagaa gagaattatt ttatcatcat    60
tttgcaaagt cattaaaagt aacaaagaag actgcgagga gtgaaagtgc atcagggata    120 aggaagaaa atg cgt tgc aca ttg att ttt gca att att gct ggc att gca    171
         Met Arg Cys Thr Leu Ile Phe Ala Ile Ile Ala Gly Ile Ala
           1               5                  10 att aca gct ttg gcc aca aat cca cca cgc tgg gat ccc aac tat ata    219
```

```
Ile Thr Ala Leu Ala Thr Asn Pro Pro Arg Trp Asp Pro Asn Tyr Ile
 15                  20                  25                  30 gtt aag ggc aca tta tat att ccc tat gcg gaa ata gct gaa cca ttt         267
Val Lys Gly Thr Leu Tyr Ile Pro Tyr Ala Glu Ile Ala Glu Pro Phe
                 35                  40                  45 tat gcc tgg tac gat aag aat aca cga cgt tcc cgt att gat tac tat         315
Tyr Ala Trp Tyr Asp Lys Asn Thr Arg Arg Ser Arg Ile Asp Tyr Tyr
             50                  55                  60 ggt ggc atg gtg aaa acc tat caa ttg gca aat gaa cat cct ttt ggt         363
Gly Gly Met Val Lys Thr Tyr Gln Leu Ala Asn Glu His Pro Phe Gly
         65                  70                  75 act tct tta aaa ttg gcc ccc att acc act aaa tca gag tta aac aaa         411
Thr Ser Leu Lys Leu Ala Pro Ile Thr Thr Lys Ser Glu Leu Asn Lys
     80                  85                  90 gta aca tgt ctt caa ctg aat ggc act tct gaa gat ccc gta caa gtg         459
Val Thr Cys Leu Gln Leu Asn Gly Thr Ser Glu Asp Pro Val Gln Val
 95                 100                 105                 110 caa gca ata ttg cca aat gcc aag gac ttc aaa ctt ata ggc act gaa         507
Gln Ala Ile Leu Pro Asn Ala Lys Asp Phe Lys Leu Ile Gly Thr Glu
                115                 120                 125 acc ttt tta ggc ttc aac tgt gac aaa ttc cgc tta gag gaa aca att         555
Thr Phe Leu Gly Phe Asn Cys Asp Lys Phe Arg Leu Glu Glu Thr Ile
            130                 135                 140 ggc gat aag aaa aat gta tac act ttg tgg gta cgt tat aag aag tca         603
Gly Asp Lys Lys Asn Val Tyr Thr Leu Trp Val Arg Tyr Lys Lys Ser
        145                 150                 155 ccc cat tat ccg gct tca aga atg ccc ata cca gta cgc tat gaa atg         651
Pro His Tyr Pro Ala Ser Arg Met Pro Ile Pro Val Arg Tyr Glu Met
    160                 165                 170 aga ggt tac aat acc ctt ttg ggt tcc cat tat gat cac tat tat ctg         699
Arg Gly Tyr Asn Thr Leu Leu Gly Ser His Tyr Asp His Tyr Tyr Leu
175                 180                 185                 190 gat tat gat agt tac gat cac gat gat ata ccc aat gaa gta ttt gaa         747
Asp Tyr Asp Ser Tyr Asp His Asp Asp Ile Pro Asn Glu Val Phe Glu
                195                 200                 205 ttg gat gat aac atg gaa tgt atg cct ttc cct gga ccc ggc aaa ggt         795
Leu Asp Asp Asn Met Glu Cys Met Pro Phe Pro Gly Pro Gly Lys Gly
            210                 215                 220 cat tat gcc acc ttc aat ccc atg caa gag ttt gtt cat ccc act gta         843
His Tyr Ala Thr Phe Asn Pro Met Gln Glu Phe Val His Pro Thr Val
        225                 230                 235 gac cat cat gtg gag cat gcc ttt aaa cat ttc aaa aac aag cat ggc         891
Asp His His Val Glu His Ala Phe Lys His Phe Lys Asn Lys His Gly
    240                 245                 250 att gat tat cgc acc gaa caa gag cat gaa tat cgt aaa aac atc ttt         939
Ile Asp Tyr Arg Thr Glu Gln Glu His Glu Tyr Arg Lys Asn Ile Phe
255                 260                 265                 270 aga caa aat ctg aga ttt att aat tcg aaa aat cgt ggc aaa tta agt         987
Arg Gln Asn Leu Arg Phe Ile Asn Ser Lys Asn Arg Gly Lys Leu Ser
                275                 280                 285 tat act ctt gcc att aac cac ttg gca gat aaa agc gat gat gaa cta        1035
Tyr Thr Leu Ala Ile Asn His Leu Ala Asp Lys Ser Asp Asp Glu Leu
            290                 295                 300 aag ggt cgt cga ggt tat aaa tca tcg ggt gtc ttt aat aca ggc aaa        1083
Lys Gly Arg Arg Gly Tyr Lys Ser Ser Gly Val Phe Asn Thr Gly Lys
        305                 310                 315 cca ttc cct tac aat ttg gaa aag tac cgt gac aca gtg cca gat caa        1131
Pro Phe Pro Tyr Asn Leu Glu Lys Tyr Arg Asp Thr Val Pro Asp Gln
    320                 325                 330
```

-continued

```
tat gat tgg cgt ttg tat ggt gcc gta aca ccc gtt aaa gat caa tct     1179
Tyr Asp Trp Arg Leu Tyr Gly Ala Val Thr Pro Val Lys Asp Gln Ser
335                 340                 345                 350 gtt tgc ggt tct tgt tgg tct ttt ggc act att ggc cat ttg gag ggt     1227
Val Cys Gly Ser Cys Trp Ser Phe Gly Thr Ile Gly His Leu Glu Gly
            355                 360                 365 gca ttt ttc ctt aag aat ggc ggc aat ttg gta cgc tta tcg caa caa     1275
Ala Phe Phe Leu Lys Asn Gly Gly Asn Leu Val Arg Leu Ser Gln Gln
        370                 375                 380 gct tta atc gat tgc tct tgg gag tat ggc aac aac ggt tgt gat ggt     1323
Ala Leu Ile Asp Cys Ser Trp Glu Tyr Gly Asn Asn Gly Cys Asp Gly
    385                 390                 395 ggc gaa gat ttc cgt gcc tat aaa tgg atg atg gaa atg ggt ggt gta     1371
Gly Glu Asp Phe Arg Ala Tyr Lys Trp Met Met Glu Met Gly Gly Val
400                 405                 410 ccc aca gaa gaa gaa tat ggt ccc tat tta ggt caa gat ggt tat tgt     1419
Pro Thr Glu Glu Glu Tyr Gly Pro Tyr Leu Gly Gln Asp Gly Tyr Cys
415                 420                 425                 430 cat gcc aaa aat gtt agt ctg gtg gca ccc att act ggc ttc ttt aat     1467
His Ala Lys Asn Val Ser Leu Val Ala Pro Ile Thr Gly Phe Phe Asn
            435                 440                 445 gtt aca cct aat gat cct atg gct tta aaa att gcc ctt tta aaa cat     1515
Val Thr Pro Asn Asp Pro Met Ala Leu Lys Ile Ala Leu Leu Lys His
        450                 455                 460 ggc ccc ata tcg gtt gct att gat gcc tca ccc aaa acc ttt agt ttc     1563
Gly Pro Ile Ser Val Ala Ile Asp Ala Ser Pro Lys Thr Phe Ser Phe
    465                 470                 475 tat tcg cac ggt gtc tac tat gaa cct acc tgc aag aat ggt ctt gat     1611
Tyr Ser His Gly Val Tyr Tyr Glu Pro Thr Cys Lys Asn Gly Leu Asp
480                 485                 490 gaa ctt gat cat gct gtc ttg gcc gtg ggc tat ggc aca atc aac ggc     1659
Glu Leu Asp His Ala Val Leu Ala Val Gly Tyr Gly Thr Ile Asn Gly
495                 500                 505                 510 gaa gat tac tgg ctg gta aag aat tct tgg tct act tat tgg ggc aat     1707
Glu Asp Tyr Trp Leu Val Lys Asn Ser Trp Ser Thr Tyr Trp Gly Asn
            515                 520                 525 gat ggt tat att tta atg tct gcc cgt aaa aat aat tgc ggt gtt atg     1755
Asp Gly Tyr Ile Leu Met Ser Ala Arg Lys Asn Asn Cys Gly Val Met
        530                 535                 540 acc atg ccc act tat gta gag atg taagcatatt gatggtctgc ttaaagcttt    1809
Thr Met Pro Thr Tyr Val Glu Met
            545                 550 ataaaatgac tttaattttc atttaatttt tctttaattt ttttttttat aagttgatct   1869
actaaaataa gaaagaaaat aaaaattgtt taaataaaaa aaaaaa                  1915
```

<210> SEQ ID NO 3
<211> LENGTH: 549
<212> TYPE: PRT
<213> ORGANISM: Drosophila melanogaster

<400> SEQUENCE: 3

```
Met Gln Val Phe Leu Ala Leu Ala Leu Leu Ala Gly Leu Ala Phe Ser
1               5                   10                  15

Ala Asn Ala Thr Asn Pro Pro Lys Trp Asp Pro Asn Tyr Ile Val Lys
            20                  25                  30

Gly Thr Leu Tyr Ile Pro Tyr Ala Glu Ile Ala Glu Pro Phe Tyr Ala
        35                  40                  45

Trp Tyr Asp Lys Asn Thr Arg Ser Arg Ile Asp Tyr Tyr Gly Gly
    50                  55                  60
```

-continued

```
Met Val Lys Thr Tyr Gln Leu Ala Gly Glu Gly Gln Tyr Gly Thr Leu
 65                  70                  75                  80

Leu Lys Leu Ala Pro Ile Thr Lys Thr Glu Asn Asn Lys Leu Thr
                 85                  90                  95

Cys Leu Gln Val Asn Gly Thr Ala Asp Gln Ala Val Asp Ile Gln Ser
                100                 105                 110

Ile Leu Pro Asp Ala Lys Pro Phe Ser Leu Val Gly Thr Glu Ser Phe
            115                 120                 125

Leu Gly Tyr Thr Cys Asp Lys Phe Arg Leu Glu Ser Thr Ile Gly Gln
        130                 135                 140

Lys Lys Asn Ile Tyr Thr Leu Trp Val Arg Tyr Lys Lys Ser Pro His
145                 150                 155                 160

Tyr Pro Ser Ser Arg Met Pro Ile Pro Val Arg Tyr Glu Met Arg Gly
                165                 170                 175

Tyr Asn Thr Leu Leu Gly Ser His Tyr Asp His Tyr Tyr Leu Asp Tyr
            180                 185                 190

Asp Ser Tyr Glu His Asp Asp Ile Pro Asn Glu Val Phe Glu Ile Asp
        195                 200                 205

Asp Ser Leu Gln Cys Val Gly Phe Pro Gly Pro Gly Thr Gly His Tyr
    210                 215                 220

Ala Thr Phe Asn Pro Met Gln Glu Phe Ile Ser Gly Thr Asp Glu His
225                 230                 235                 240

Val Asp Lys Ala Phe His His Phe Lys Arg Lys His Gly Val Ala Tyr
                245                 250                 255

His Ser Asp Thr Glu His Glu His Arg Lys Asn Ile Phe Arg Gln Asn
            260                 265                 270

Leu Arg Tyr Ile His Ser Lys Asn Arg Ala Lys Leu Thr Tyr Thr Leu
        275                 280                 285

Ala Val Asn His Leu Ala Asp Lys Thr Glu Glu Leu Lys Ala Arg
    290                 295                 300

Arg Gly Tyr Lys Ser Ser Gly Ile Tyr Asn Thr Gly Lys Pro Phe Pro
305                 310                 315                 320

Tyr Asp Val Pro Lys Tyr Lys Asp Glu Ile Pro Asp Gln Tyr Asp Trp
                325                 330                 335

Arg Leu Tyr Gly Ala Val Thr Pro Val Lys Asp Gln Ser Val Cys Gly
            340                 345                 350

Ser Cys Trp Ser Phe Gly Thr Ile Gly His Leu Glu Gly Ala Phe Phe
        355                 360                 365

Leu Lys Asn Gly Gly Asn Leu Val Arg Leu Ser Gln Gln Ala Leu Ile
    370                 375                 380

Asp Cys Ser Trp Ala Tyr Gly Asn Asn Gly Cys Asp Gly Gly Glu Asp
385                 390                 395                 400

Phe Arg Val Tyr Gln Trp Met Leu Gln Ser Gly Val Pro Thr Glu
                405                 410                 415

Glu Glu Tyr Gly Pro Tyr Leu Gly Gln Asp Gly Tyr Cys His Val Asn
            420                 425                 430

Asn Val Thr Leu Val Ala Pro Ile Lys Gly Phe Val Asn Val Thr Ser
        435                 440                 445

Asn Asp Pro Asn Ala Phe Lys Leu Ala Leu Leu Lys His Gly Pro Leu
    450                 455                 460

Ser Val Ala Ile Asp Ala Ser Pro Lys Thr Phe Ser Phe Tyr Ser His
465                 470                 475                 480
```

```
Gly Val Tyr Tyr Glu Pro Thr Cys Lys Asn Asp Val Asp Gly Leu Asp
              485                 490                 495

His Ala Val Leu Ala Val Gly Tyr Gly Ser Ile Asn Gly Glu Asp Tyr
        500                 505                 510

Trp Leu Val Lys Asn Ser Trp Ser Thr Tyr Trp Gly Asn Asp Gly Tyr
            515                 520                 525

Ile Leu Met Ser Ala Lys Lys Asn Asn Cys Gly Val Met Thr Met Pro
        530                 535                 540

Thr Tyr Val Glu Met
545

<210> SEQ ID NO 4
<211> LENGTH: 1839
<212> TYPE: DNA
<213> ORGANISM: Drosophila melanogaster

<400> SEQUENCE: 4
```

| | | | | | |
|---|---|---|---|---|---|
| aaagataggt | agtatagtag | agtcgggatc | agttcatatt | ccagacaatt | ctctggtgaa     60 |
| ttctcaagaa | tgcaagtgtt | tttagcttta | gccctgctcg | caggcttggc | tttctcagct    120 |
| aatgccacga | atccgccgaa | atgggatcca | aactacatag | tcaaaggaac | cctgtacatt    180 |
| ccgtacgccg | agattgcgga | acccttctac | gcctggtatg | acaagaatac | gaggcgatcc    240 |
| cgcatcgatt | actacggcgg | aatggtgaag | acataccaac | tggctggcga | gggtcagtac    300 |
| ggaaccctgc | tgaagctggc | accgattacc | accaagacgg | agaacaacaa | gctaacctgt    360 |
| ctgcaggtga | atggcaccgc | cgaccaggct | gtcgatattc | agagcatcct | gcccgatgcg    420 |
| aaacctttca | gcctggtggg | caccgaatcc | tttttgggct | cacgtgcga | caagttccgc    480 |
| ctggagtcga | caattggcca | aagaagaac | atctatacgc | tgtgggtgcg | gtacaagaag    540 |
| tcgccgcatt | atccctccag | ccgaatgccc | attcccgtgc | gctacgagat | gaggggctat    600 |
| aacaccctgc | tgggatcgca | ctacgatcat | tactacttgg | actatgacag | ctacgagcac    660 |
| gatgatattc | caacgaggt | gttcgagatc | gatgacagcc | tgcagtgcgt | cggattcccc    720 |
| ggacccggca | ccggtcacta | tgccaccttc | aatcccatgc | aggagttcat | atccggaacc    780 |
| gatgagcatg | tggacaaggc | cttccaccac | ttcaagcgca | agcacggagt | tgcttatcac    840 |
| agcgacacgg | aacacgagca | tcgcaagaac | atcttccgtc | agaacctgcg | ctacatccac    900 |
| tccaagaacc | gggccaaact | cacttacacg | ttggccgtta | atcacttggc | cgacaagacc    960 |
| gaagaggagt | tgaaggcacg | acgcggatac | aaatcatcgg | gcatctacaa | caccggcaaa   1020 |
| ccgttcccct | atgatgtgcc | caagtacaag | gacgagattc | ccgaccagta | cgactggcgg   1080 |
| ctgtacggcg | ctgtcactcc | ggtgaaagat | caatctgtgt | gcggatcgtg | ctggtcattt   1140 |
| ggcaccattg | gtcacctgga | gggcgccttc | ttcctgaaga | atggcggcaa | tctggtccgg   1200 |
| ctttcccagc | aggcgttgat | tgactgctcg | tgggcctatg | caacaatgg | ctgcgatggt   1260 |
| ggcgaggatt | ccgcgtgta | ccagtggatg | ctgcagtccg | gcggagtgcc | cacggaggag   1320 |
| gagtacggtc | cctatctggg | ccaggatggc | tactgtcacg | tgaacaacgt | gacgctggtg   1380 |
| gcacccatta | agggattcgt | caatgtgacc | tccaacgatc | gaatgccttt | caagctggct   1440 |
| ttgctcaagc | acgtcctctt | gtcggtggcc | attgatgctt | ctcccaagac | atttagcttc   1500 |
| tactcgcacg | gagtttacta | tgagccaacg | tgcaagaacg | atgtagatgg | actggatcat   1560 |
| gctgtcttgg | ccgtgggcta | tggctcaatc | aatggagagg | actattggct | ggtgaagaac   1620 |
| tcgtggtcca | cctactgggg | caacgatggc | tacatcctga | tgtcggccaa | gaagaacaat   1680 |

```
tgcggtgtta tgaccatgcc cacttatgtg gagatgtaga ttgtcccgtt cctgcctaca    1740
tatttcttat tttgtgtact cttttattt ttacgcccac agggcgctaa atatgcaata    1800
catttcatga actctttgt aaaaaaaaaa aaaaaaaa                             1839
```

<210> SEQ ID NO 5
<211> LENGTH: 552
<212> TYPE: PRT
<213> ORGANISM: Periplaneta americana

<400> SEQUENCE: 5

```
Met Ala Trp Asn Leu Leu Phe Ser Ala Val Leu Ala Ile Ala Phe Val
 1               5                   10                  15

Ser Val Leu Gly Ala Asp Pro Thr Pro Pro Asn Phe Ser Asp Thr Tyr
            20                  25                  30

Thr Val Lys Gly Thr Leu Tyr Ile Pro Tyr Ala Glu Ile Arg Glu Pro
        35                  40                  45

Phe Leu Ala Tyr Tyr Asp Leu Thr Val Gly Ser Ser Arg Ile Asp Tyr
    50                  55                  60

Tyr Gly Gly Met Val Lys Thr Tyr Gln Ile Ser Lys Tyr Gly Asn Phe
 65                  70                  75                  80

Gly Thr Ser Leu Lys Val Ala Pro Val Thr Thr Glu Lys Val Glu Asn
                85                  90                  95

Lys Glu Thr Cys Leu Gln Val Asn Gly Thr Lys Asp Asn Lys Ile Glu
            100                 105                 110

Pro Gln Ser Ile Leu Pro Asp Leu Thr Gly Phe Lys Leu Ile Gly Thr
        115                 120                 125

Glu Pro Ile Asn Gly Leu Asn Cys Glu Lys Trp Arg Leu Val Asp Thr
    130                 135                 140

Lys Gly Ala Lys Val Asn Lys Tyr Thr Met Trp Ile Arg Tyr Lys Lys
145                 150                 155                 160

Ser Ala Asn Asp Pro Gly Val Lys Ile Ala Ile Pro Val Arg Tyr Glu
                165                 170                 175

Met Lys Gly Tyr Asn Ser Leu Leu Gly Ser His Tyr Asp His Tyr Tyr
            180                 185                 190

Leu Glu Tyr Asp Trp Phe Ala Phe Lys Lys Pro Asp Pro Val Val Phe
        195                 200                 205

Lys Val Asp Ser Asn Leu Thr Cys Thr Ser Phe Pro Gly Pro Gly Asp
    210                 215                 220

Arg His Ile Tyr Thr Phe Asn Pro Met Lys Glu Phe Ile His Asn Tyr
225                 230                 235                 240

Asp Glu His Val Glu Thr Ala Phe Asp His Phe Arg Lys Arg His Ser
                245                 250                 255

Lys Asp Tyr Ala Ser Asn Leu Glu His Thr Lys Arg Lys Glu Ile Phe
            260                 265                 270

Arg Gln Asn Leu Arg Phe Ile His Ser Lys Asn Arg Ala Arg Leu Gly
        275                 280                 285

Phe Thr Leu Asp Val Asn His Leu Ala Asp Arg Thr Glu Leu Glu Leu
    290                 295                 300

Lys Ala Leu Arg Gly Lys Gln Tyr Thr Asp Gly Tyr Asn Gly Gly Ser
305                 310                 315                 320

Pro Phe Pro Tyr Thr Asn Leu Asp Ala Ile Met Asp Gln Ile Pro Asp
                325                 330                 335

Asp Leu Asp Trp Arg Ile Tyr Gly Ala Val Thr Pro Val Lys Asp Gln
            340                 345                 350
```

```
Ser Val Cys Gly Ser Cys Trp Ser Phe Gly Thr Thr Gly Thr Ile Glu
        355                 360                 365
Gly Ala Tyr Phe Leu Lys Tyr Gly His Leu Val Arg Leu Ser Gln Gln
    370                 375                 380
Ala Leu Ile Asp Cys Ser Trp Gly Tyr Gly Asn Asn Gly Cys Asp Gly
385                 390                 395                 400
Gly Glu Asp Phe Arg Ser Tyr Glu Trp Met Met Lys His Gly Gly Ile
                405                 410                 415
Pro Leu Glu Asp Glu Tyr Gly Gly Tyr Leu Gly Gln Asp Gly Tyr Cys
            420                 425                 430
His Val Glu Asn Val Thr Leu Thr Ala Lys Ile Thr Gly Tyr Val Asn
        435                 440                 445
Val Thr Ser Gly Asp Ile Asp Ala Leu Lys Val Ala Leu Ala Lys His
    450                 455                 460
Gly Pro Ile Ser Val Ala Ile Asp Ala Ser His Lys Thr Phe Ser Phe
465                 470                 475                 480
Tyr Ser Asn Gly Ile Tyr Tyr Asp Pro Glu Cys Gly Asn Lys Leu Asp
                485                 490                 495
Gln Leu Asp His Ala Val Leu Leu Val Gly Tyr Gly Ile Ile Asn Gly
            500                 505                 510
Asn Pro Tyr Trp Leu Val Lys Asn Ser Trp Ser Asn Tyr Trp Gly Asn
        515                 520                 525
Asp Gly Tyr Ile Leu Met Ser Pro Lys Asp Asn Asn Cys Gly Val Ala
    530                 535                 540
Thr Asp Pro Thr Tyr Val Thr Met
545                 550

<210> SEQ ID NO 6
<211> LENGTH: 1833
<212> TYPE: DNA
<213> ORGANISM: Periplaneta americana

<400> SEQUENCE: 6 gggaagggc caatttctgt atcggtactt ttgctcttcc tgatttcgag aacttcagct      60
gaagcattac atggcttgga atcttttatt ttcggcggtg ttggccatcg cttttgtgtc     120
tgtgctgggt gcagatccaa caccaccgaa cttcagtgat acttatacag taaagggaac    180
actttacatt ccatatgcag agattcgtga gcctttctta gcgtattacg acttgactgt    240
tgggtctagc cgcattgatt actatggagg aatggtgaaa acgtatcaaa tcagcaagta    300
tggaaatttc ggaacaagtt taaggttgc acctgtgaca acagagaaag tagagaataa     360
ggaaacttgc ttacaagtca acggaaccaa agacaacaaa atcgaaccac agagtattct    420
tccagactta acaggattca agttgattgg tacagaacca ataaatggcc tgaattgcga    480
aaaatggcgt ttggtggaca caaaaggagc caaggtcaac aaatacacaa tgtggattcg    540
gtacaagaag tctgcaaatg atcctggtgt aaaaatcgcc atcccagttc gatacgaaat    600
gaagggttac aactctttgc tgggttctca ttatgaccac tactacctgg agtacgattg    660
gtttgctttc aagaagcctg atccagttgt gttcaaagtt gacagcaatt gacatgcac    720
cagcttccca ggtccaggag acagacatat ttatacattt aacctatga aggagttcat    780
tcataattat gacgaacatg tagaaaccgc atttgatcac ttcgaaaaaa gacacagcaa    840
ggactacgcc agcaatttgg aacacacaaa gagaaaagaa attttccgac agaatttgag    900
gttcatccat tctaagaatc gtgctagatt aggattcact ctggacgtga accatttggc    960
```

```
ggaccggaca gagctcgaac tgaaagctct gaggggggaag caatacactg atgggtacaa    1020
tggaggttct ccatttcctt ataccaatct tgacgcaatc atggaccaaa ttcctgatga    1080
tttggactgg agaatttatg gtgctgtgac tccagttaaa gatcagtctg tttgcggctc    1140
ttgttggagt tttgggacta ctggcaccat cgaaggagct tatttcttaa agtatggaca    1200
tttggtgcga ttgtcacaac aggctctaat tgactgcagc tggggctatg gtaacaatgg    1260
ttgtgatgga ggtgaagatt ccgctctta tgaatggatg atgaagcatg gtggcatccc    1320 actgaagac gaatatggag gctatttggg ccaggatggc tattgtcatg tcgaaaatgt    1380
aactctcaca gcaaagatca ctggctatgt gaacgtcaca tctggagaca ttgatgcttt    1440
gaaggtagca ctagccaagc atggtcccat ctctgttgca attgatgctt ctcacaagac    1500
cttctccttc tattcgaatg gcatctacta tgatcctgag tgtggaaaca agctagatca    1560
gttggaccac gcagttctgc tggttggtta tggcatcata aatggaaacc cttattggtt    1620
ggtcaaaaat tcctggtcta attattgggg caacgatggc tacatcctta tgtcacctaa    1680
ggataacaac tgtggtgttg caactgaccc tacctacgta acaatgtaga ggaagacatg    1740
acttggcggc atatgtgata atttgttgcc tcaacacttg gggctgctta cgggaggtac    1800
attttactac gtttaattta agagctgcat cag                                 1833

<210> SEQ ID NO 7
<211> LENGTH: 221
<212> TYPE: DNA
<213> ORGANISM: Periplaneta americana

<400> SEQUENCE: 7
aaatgtatat taatatagtt ggtgtccaag caatgtacct gtgctgcttt tcctattcag     60
ggtttttctt tcattaagaa aattgcccct tacctcagat acagagattg acaccattg    120 ggtgaaacag atacagaatg agactgtaga ctgaaaaaaa gactttgatg gagttgaaat    180
aaaactagtt tgtttcaatg tgcaaaaaaa aaaaaaaaa a                         221

<210> SEQ ID NO 8
<211> LENGTH: 28
<212> TYPE: DNA
<213> ORGANISM: Artificial Sequence
<220> FEATURE:
<223> OTHER INFORMATION: Description of Artificial Sequence: primer

<400> SEQUENCE: 8
aaacatatga caaatccacc acgctggg                                         28

<210> SEQ ID NO 9
<211> LENGTH: 28
<212> TYPE: DNA
<213> ORGANISM: Artificial Sequence
<220> FEATURE:
<223> OTHER INFORMATION: Description of Artificial Sequence: primer

<400> SEQUENCE: 9
ccacatatgg acacagtgcc agatcaat                                         28

<210> SEQ ID NO 10
<211> LENGTH: 28
<212> TYPE: DNA
<213> ORGANISM: Artificial Sequence
<220> FEATURE:
<223> OTHER INFORMATION: Description of Artificial Sequence: primer
```

```
<400> SEQUENCE: 10
ccctcgagtt acatctctac ataagtgg                                    28

<210> SEQ ID NO 11
<211> LENGTH: 7
<212> TYPE: PRT
<213> ORGANISM: Sarcophaga peregrina

<400> SEQUENCE: 11

Thr Asn Pro Pro Arg Trp Asp
  1               5

<210> SEQ ID NO 12
<211> LENGTH: 13
<212> TYPE: PRT
<213> ORGANISM: Sarcophaga peregrina

<400> SEQUENCE: 12

Thr Asn Pro Pro Arg Trp Asp Pro Asn Tyr Ile Val Lys
  1               5                  10

<210> SEQ ID NO 13
<211> LENGTH: 20
<212> TYPE: PRT
<213> ORGANISM: Sarcophaga peregrina
<220> FEATURE:
<221> NAME/KEY: MOD_RES
<222> LOCATION: (1)
<223> OTHER INFORMATION: may be Gly or Ala

<400> SEQUENCE: 13

Xaa Thr Leu Tyr Ile Pro Tyr Ala Glu Ile Ala Glu Pro Phe Tyr Ala
  1               5                  10                  15

Trp Tyr Asp Lys
           20

<210> SEQ ID NO 14
<211> LENGTH: 23
<212> TYPE: PRT
<213> ORGANISM: Sarcophaga peregrina

<400> SEQUENCE: 14

Thr Asn Pro Pro Arg Trp Asp Pro Asn Tyr Ile Val Lys Gly Thr Leu
  1               5                  10                  15

Tyr Ile Pro Tyr Ala Glu Ile
              20

<210> SEQ ID NO 15
<211> LENGTH: 33
<212> TYPE: PRT
<213> ORGANISM: Sarcophaga peregrina

<400> SEQUENCE: 15

Thr Asn Pro Pro Arg Trp Asp Pro Asn Tyr Ile Val Lys Gly Thr Leu
  1               5                  10                  15

Tyr Ile Pro Tyr Ala Glu Ile Ala Glu Pro Phe Tyr Ala Trp Tyr Asp
              20                  25                  30

Lys

<210> SEQ ID NO 16
<211> LENGTH: 24
<212> TYPE: PRT
<213> ORGANISM: Sarcophaga peregrina
```

```
<400> SEQUENCE: 16

Val Thr Ala Leu Gln Leu Tyr Gly Thr Ser Glu Asp Pro Val Gln Val
1               5                   10                  15

Gln Ala Ile Leu Pro Asn Ala Lys
            20

<210> SEQ ID NO 17
<211> LENGTH: 10
<212> TYPE: PRT
<213> ORGANISM: Sarcophaga peregrina

<400> SEQUENCE: 17

Asn Val Tyr Thr Leu Trp Val Arg Tyr Lys
1               5                   10

<210> SEQ ID NO 18
<211> LENGTH: 17
<212> TYPE: PRT
<213> ORGANISM: Sarcophaga peregrina

<400> SEQUENCE: 18

Ser Pro His Tyr Pro Ala Ser Arg Met Pro Ile Pro Val Arg Tyr Glu
1               5                   10                  15

Met

<210> SEQ ID NO 19
<211> LENGTH: 18
<212> TYPE: PRT
<213> ORGANISM: Sarcophaga peregrina
<220> FEATURE:
<221> NAME/KEY: MOD_RES
<222> LOCATION: (14)
<223> OTHER INFORMATION: may be Arg or Val

<400> SEQUENCE: 19

Ser Pro His Tyr Pro Ala Ser Arg Met Pro Ile Ile Val Xaa Tyr Glu
1               5                   10                  15

Met Arg

<210> SEQ ID NO 20
<211> LENGTH: 10
<212> TYPE: PRT
<213> ORGANISM: Sarcophaga peregrina

<400> SEQUENCE: 20

Met Pro Ile Pro Val Arg Tyr Glu Met Arg
1               5                   10

<210> SEQ ID NO 21
<211> LENGTH: 18
<212> TYPE: PRT
<213> ORGANISM: Sarcophaga peregrina

<400> SEQUENCE: 21

Ser Pro His Tyr Pro Ala Ser Arg Met Pro Ile Pro Val Arg Tyr Glu
1               5                   10                  15

Met Arg

<210> SEQ ID NO 22
<211> LENGTH: 15
<212> TYPE: PRT
<213> ORGANISM: Sarcophaga peregrina
```

<400> SEQUENCE: 22

Asn Thr Arg Arg Ser Arg Ile Asp Tyr Tyr Gly Gly Met Val Lys
1               5                   10                  15

<210> SEQ ID NO 23
<211> LENGTH: 15
<212> TYPE: PRT
<213> ORGANISM: Sarcophaga peregrina

<400> SEQUENCE: 23

Thr Tyr Gln Leu Ala Asn Glu His Pro Phe Gly Thr Ser Leu Lys
1               5                   10                  15

<210> SEQ ID NO 24
<211> LENGTH: 22
<212> TYPE: PRT
<213> ORGANISM: Sarcophaga peregrina

<400> SEQUENCE: 24

Ser Arg Ile Asp Tyr Tyr Gly Gly Met Val Lys Thr Tyr Gln Leu Ala
1               5                   10                  15

Asn Glu His Pro Phe Gly
            20

<210> SEQ ID NO 25
<211> LENGTH: 30
<212> TYPE: PRT
<213> ORGANISM: Sarcophaga peregrina

<400> SEQUENCE: 25

Asn Thr Arg Arg Ser Arg Ile Asp Tyr Tyr Gly Gly Met Val Lys Thr
1               5                   10                  15

Tyr Gln Leu Ala Asn Glu His Pro Phe Gly Thr Ser Leu Lys
            20                  25                  30

<210> SEQ ID NO 26
<211> LENGTH: 10
<212> TYPE: PRT
<213> ORGANISM: Sarcophaga peregrina

<400> SEQUENCE: 26

Phe Arg Leu Glu Glu Thr Ile Gly Asp Lys
1               5                   10

<210> SEQ ID NO 27
<211> LENGTH: 14
<212> TYPE: PRT
<213> ORGANISM: Sarcophaga peregrina
<220> FEATURE:
<221> NAME/KEY: MOD_RES
<222> LOCATION: (12)
<223> OTHER INFORMATION: may be Tyr or Ala

<400> SEQUENCE: 27

Leu Ile Gly Thr Glu Thr Phe Leu Gly Phe Asn Xaa Asp Lys
1               5                   10

<210> SEQ ID NO 28
<211> LENGTH: 11
<212> TYPE: PRT
<213> ORGANISM: Sarcophaga peregrina

<400> SEQUENCE: 28

```
Gly Tyr Asn Thr Leu Leu Gly Ser His Tyr Asp
 1               5                  10

<210> SEQ ID NO 29
<211> LENGTH: 15
<212> TYPE: PRT
<213> ORGANISM: Sarcophaga peregrina

<400> SEQUENCE: 29

Asp Thr Val Pro Asp Gln Tyr Asp Trp Arg Leu Tyr Gly Ala Val
 1               5                  10                  15

<210> SEQ ID NO 30
<211> LENGTH: 19
<212> TYPE: PRT
<213> ORGANISM: Sarcophaga peregrina

<400> SEQUENCE: 30

Asp Thr Val Pro Asp Gln Tyr Asp Trp Arg Leu Tyr Gly Ala Val Thr
 1               5                  10                  15

Pro Val Lys

<210> SEQ ID NO 31
<211> LENGTH: 19
<212> TYPE: PRT
<213> ORGANISM: Sarcophaga peregrina
<220> FEATURE:
<221> NAME/KEY: MOD_RES
<222> LOCATION: (1)
<223> OTHER INFORMATION: undetermined amino acid
<220> FEATURE:
<221> NAME/KEY: MOD_RES
<222> LOCATION: (3)
<223> OTHER INFORMATION: may be Trp or Ser

<400> SEQUENCE: 31

Xaa Gly Xaa Asn Thr Tyr Trp Gly Asn Asp Gln Tyr Ile Leu Met Ser
 1               5                  10                  15

Ala Trp Lys

<210> SEQ ID NO 32
<211> LENGTH: 23
<212> TYPE: PRT
<213> ORGANISM: Sarcophaga peregrina
<220> FEATURE:
<221> NAME/KEY: MOD_RES
<222> LOCATION: (3)
<223> OTHER INFORMATION: may be Ser or Trp

<400> SEQUENCE: 32

Asn Val Xaa Leu Val Ala Pro Ile Thr Gly Phe Phe Asn Val Thr Pro
 1               5                  10                  15

Asn Asp Pro Met Ala Leu Lys
            20

<210> SEQ ID NO 33
<211> LENGTH: 27
<212> TYPE: PRT
<213> ORGANISM: Sarcophaga peregrina
<220> FEATURE:
<221> NAME/KEY: MOD_RES
<222> LOCATION: (1)
<223> OTHER INFORMATION: may be Asn or Asp
<220> FEATURE:
<221> NAME/KEY: MOD_RES
<222> LOCATION: (3)
<223> OTHER INFORMATION: may be Asp or Val
```

```
<400> SEQUENCE: 33

Xaa Gly Leu Xaa Glu Leu Asp His Ala Val Leu Ala Val Gly Tyr Gly
 1               5                  10                  15

Thr Ile Asn Gly Glu Asp Tyr Trp Leu Val Lys
                20                  25

<210> SEQ ID NO 34
<211> LENGTH: 24
<212> TYPE: PRT
<213> ORGANISM: Sarcophaga peregrina
<220> FEATURE:
<221> NAME/KEY: MOD_RES
<222> LOCATION: (1)
<223> OTHER INFORMATION: may be Asp or Asn
<220> FEATURE:
<221> NAME/KEY: MOD_RES
<222> LOCATION: (3)
<223> OTHER INFORMATION: may be Val or Asp
<220> FEATURE:
<221> NAME/KEY: MOD_RES
<222> LOCATION: (18)
<223> OTHER INFORMATION: may be Glu or Val
<220> FEATURE:
<221> NAME/KEY: MOD_RES
<222> LOCATION: (19)
<223> OTHER INFORMATION: may be Gly or Lys

<400> SEQUENCE: 34

Xaa Gln Ser Xaa Thr Gly Ser Cys Trp Ser Phe Gly Thr Ile Gly His
 1               5                  10                  15

Leu Xaa Xaa Ala Phe Phe Leu Lys
                20

<210> SEQ ID NO 35
<211> LENGTH: 14
<212> TYPE: PRT
<213> ORGANISM: Sarcophaga peregrina

<400> SEQUENCE: 35

Asn Asn Ala Gly Val Met Thr Met Pro Thr Tyr Val Glu Met
 1               5                  10

<210> SEQ ID NO 36
<211> LENGTH: 23
<212> TYPE: PRT
<213> ORGANISM: Sarcophaga peregrina

<400> SEQUENCE: 36

Trp Met Met Glu Met Gly Gly Val Pro Thr Glu Glu Tyr Gly Pro
 1               5                  10                  15

Tyr Leu Gly Gln Asp Gly Tyr
                20

<210> SEQ ID NO 37
<211> LENGTH: 33
<212> TYPE: PRT
<213> ORGANISM: Sarcophaga peregrina

<400> SEQUENCE: 37

Thr Asn Pro Pro Arg Trp Asp Pro Asn Tyr Ile Val Lys Gly Thr Leu
 1               5                  10                  15

Tyr Ile Pro Tyr Ala Glu Ile Ala Glu Pro Phe Tyr Ala Trp Tyr Asp
                20                  25                  30

Lys
```

```
<210> SEQ ID NO 38
<211> LENGTH: 19
<212> TYPE: DNA
<213> ORGANISM: Artificial Sequence
<220> FEATURE:
<223> OTHER INFORMATION: Description of Artificial Sequence: primer
<220> FEATURE:
<223> OTHER INFORMATION: "n" is A, T, C, G, other or unknown

<400> SEQUENCE: 38
aatccacccm gntgggayc                                                    19

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: primer
<220> FEATURE:
<223> OTHER INFORMATION: "n" is A, T, C, G, other or unknown

<400> SEQUENCE: 39
gagcccttyt aygcntggta                                                   20

<210> SEQ ID NO 40
<211> LENGTH: 20
<212> TYPE: DNA
<213> ORGANISM: Artificial Sequence
<220> FEATURE:
<223> OTHER INFORMATION: Description of Artificial Sequence: primer
<220> FEATURE:
<223> OTHER INFORMATION: "n" is A, T, C, G, other or unknown

<400> SEQUENCE: 40
tgggacccca aytayathgt                                                   20

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence: primer
<220> FEATURE:
<223> OTHER INFORMATION: "n" is A, T, C, G, other or unknown

<400> SEQUENCE: 41
taccaggcgt araanggytc                                                   20

<210> SEQ ID NO 42
<211> LENGTH: 30
<212> TYPE: PRT
<213> ORGANISM: Sarcophaga peregrina

<400> SEQUENCE: 42

Asn Thr Arg Arg Ser Arg Ile Asp Tyr Tyr Gly Gly Met Val Lys Thr
 1               5                  10                  15

Tyr Gln Leu Ala Asn Glu His Pro Phe Gly Thr Ser Leu Lys
             20                  25                  30

<210> SEQ ID NO 43
<211> LENGTH: 20
<212> TYPE: DNA
<213> ORGANISM: Artificial Sequence
<220> FEATURE:
<223> OTHER INFORMATION: Description of Artificial Sequence: primer
<220> FEATURE:
```

```
<223> OTHER INFORMATION: "n" is A, T, C, G, other or unknown

<400> SEQUENCE: 43
ttcaccatgc cnccrtarta                                               20

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence: primer
<220> FEATURE:
<223> OTHER INFORMATION: "n" is A, T, C, G, other or unknown

<400> SEQUENCE: 44
gtgccgaang grtgytcrtt                                               20

<210> SEQ ID NO 45
<211> LENGTH: 10
<212> TYPE: PRT
<213> ORGANISM: Sarcophaga peregrina

<400> SEQUENCE: 45

Phe Arg Leu Glu Glu Thr Ile Gly Asp Lys
  1               5                  10

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: primer
<220> FEATURE:
<223> OTHER INFORMATION: "n" is A, T, C, G, other or unknown

<400> SEQUENCE: 46
ttgtcgccda tngtytcytc                                               20

<210> SEQ ID NO 47
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 47
tggccacaaa tccaccacgc                                               20

<210> SEQ ID NO 48
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 48
caattggcaa atgaacatcc                                               20

<210> SEQ ID NO 49
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 49
```

```
ctcttgccat taaccacttg                                          20

<210> SEQ ID NO 50
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 50
ggcactattg gccatttgga g                                        21

<210> SEQ ID NO 51
<211> LENGTH: 22
<212> TYPE: DNA
<213> ORGANISM: Artificial Sequence
<220> FEATURE:
<223> OTHER INFORMATION: Description of Artificial Sequence: primer

<400> SEQUENCE: 51
ccatatcggt tgctattgat gc                                       22

<210> SEQ ID NO 52
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 52
atggcacaat caacggcgaa g                                        21

<210> SEQ ID NO 53
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 53
gcttacatct ctacataagt g                                        21

<210> SEQ ID NO 54
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 54
agccatagga tcattaggtg t                                        21

<210> SEQ ID NO 55
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 55
gcttgttgcg ataagcgtac c                                        21

<210> SEQ ID NO 56
<211> LENGTH: 21
<212> TYPE: DNA
<213> ORGANISM: Artificial Sequence
```

-continued

```
<220> FEATURE:
<223> OTHER INFORMATION: Description of Artificial Sequence: primer

<400> SEQUENCE: 56
ccaagtggtt aatggcaaga g                                                    21

<210> SEQ ID NO 57
<211> LENGTH: 22
<212> TYPE: DNA
<213> ORGANISM: Artificial Sequence
<220> FEATURE:
<223> OTHER INFORMATION: Description of Artificial Sequence: primer

<400> SEQUENCE: 57
gatcgtaact atcataatcc ag                                                   22

<210> SEQ ID NO 58
<211> LENGTH: 22
<212> TYPE: DNA
<213> ORGANISM: Artificial Sequence
<220> FEATURE:
<223> OTHER INFORMATION: Description of Artificial Sequence: primer

<400> SEQUENCE: 58
ctataagttt gaagtccttg gc                                                   22

<210> SEQ ID NO 59
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 59
gcgtggtgga tttgtggcca                                                      20

<210> SEQ ID NO 60
<211> LENGTH: 340
<212> TYPE: PRT
<213> ORGANISM: Sarcophaga peregrina

<400> SEQUENCE: 60

Met Glu Cys Met Pro Phe Pro Gly Pro Gly Lys Gly His Tyr Ala Thr
  1               5                  10                  15

Phe Asn Pro Met Gln Glu Phe Val His Pro Thr Val Asp His His Val
                 20                  25                  30

Glu His Ala Phe Lys His Phe Lys Asn Lys His Gly Ile Asp Tyr Arg
             35                  40                  45

Thr Glu Gln Glu His Glu Tyr Arg Lys Asn Ile Phe Arg Gln Asn Leu
         50                  55                  60

Arg Phe Ile Asn Ser Lys Asn Arg Gly Lys Leu Ser Tyr Thr Leu Ala
 65                  70                  75                  80

Ile Asn His Leu Ala Asp Lys Ser Asp Glu Leu Lys Gly Arg Arg
                 85                  90                  95

Gly Tyr Lys Ser Ser Gly Val Phe Asn Thr Gly Lys Pro Phe Pro Tyr
            100                 105                 110

Asn Leu Glu Lys Tyr Arg Asp Thr Val Pro Asp Gln Tyr Asp Trp Arg
        115                 120                 125

Leu Tyr Gly Ala Val Thr Pro Val Lys Asp Gln Ser Val Cys Gly Ser
    130                 135                 140

Cys Trp Ser Phe Gly Thr Ile Gly His Leu Glu Gly Ala Phe Phe Leu
```

```
                    145                 150                 155                 160
        Lys Asn Gly Gly Asn Leu Val Arg Leu Ser Gln Gln Ala Leu Ile Asp
                        165                 170                 175

Cys Ser Trp Glu Tyr Gly Asn Asn Gly Cys Asp Gly Gly Glu Asp Phe
                        180                 185                 190

Arg Ala Tyr Lys Trp Met Met Glu Met Gly Gly Val Pro Thr Glu Glu
                        195                 200                 205

Glu Tyr Gly Pro Tyr Leu Gly Gln Asp Gly Tyr Cys His Ala Lys Asn
                        210                 215                 220

Val Ser Leu Val Ala Pro Ile Thr Gly Phe Phe Asn Val Thr Pro Asn
        225                 230                 235                 240

Asp Pro Met Ala Leu Lys Ile Ala Leu Leu Lys His Gly Pro Ile Ser
                        245                 250                 255

Val Ala Ile Asp Ala Ser Pro Lys Thr Phe Ser Phe Tyr Ser His Gly
                        260                 265                 270

Val Tyr Tyr Glu Pro Thr Cys Lys Asn Gly Leu Asp Glu Leu Asp His
                        275                 280                 285

Ala Val Leu Ala Val Gly Tyr Gly Thr Ile Asn Gly Glu Asp Tyr Trp
                        290                 295                 300

Leu Val Lys Asn Ser Trp Ser Thr Tyr Trp Gly Asn Asp Gly Tyr Ile
        305                 310                 315                 320

Leu Met Ser Ala Arg Lys Asn Asn Cys Gly Val Met Thr Met Pro Thr
                        325                 330                 335

Tyr Val Glu Met
                    340

<210> SEQ ID NO 61
<211> LENGTH: 323
<212> TYPE: PRT
<213> ORGANISM: lobster CP2

<400> SEQUENCE: 61

Met Lys Val Ala Val Leu Phe Leu Cys Gly Val Ala Leu Ala Ala Ala
        1               5                   10                  15

Ser Pro Ser Trp Glu His Phe Lys Gly Lys Tyr Gly Arg Gln Tyr Val
                        20                  25                  30

Asp Ala Glu Glu Asp Ser Tyr Arg Arg Val Ile Phe Glu Gln Asn Gln
                        35                  40                  45

Lys Tyr Ile Glu Glu Phe Asn Lys Lys Tyr Glu Asn Gly Glu Val Thr
                        50                  55                  60

Phe Asn Leu Ala Met Asn Lys Phe Gly Asp Met Thr Leu Glu Glu Phe
        65                  70                  75                  80

Asn Ala Val Met Lys Gly Asn Ile Pro Arg Arg Ser Ala Pro Val Ser
                        85                  90                  95

Val Phe Tyr Pro Lys Lys Glu Thr Gly Pro Gln Ala Thr Glu Val Asp
                        100                 105                 110

Trp Arg Thr Lys Gly Ala Val Thr Pro Val Lys Asp Gln Gly Gln Cys
                        115                 120                 125

Gly Ser Cys Trp Ala Phe Ser Thr Thr Gly Ser Leu Glu Gly Gln His
                        130                 135                 140

Phe Leu Lys Thr Gly Ser Leu Ile Ser Leu Ala Glu Gln Gln Leu Val
        145                 150                 155                 160

Asp Cys Ser Arg Pro Tyr Gly Pro Asn Gly Cys Asn Gly Gly Trp Met
                        165                 170                 175
```

```
Asn Asp Ala Phe Asp Tyr Ile Lys Ala Asn Asn Gly Ile Asp Thr Glu
            180                 185                 190

Ala Ala Tyr Pro Tyr Glu Ala Arg Asp Gly Ser Cys Arg Phe Asp Ser
            195                 200                 205

Asn Ser Val Ala Ala Thr Cys Ser Gly His Thr Asn Ile Ala Ser Gly
            210                 215                 220

Ser Glu Thr Gly Leu Gln Gln Ala Val Arg Asp Ile Gly Pro Ile Ser
225                 230                 235                 240

Val Thr Ile Asp Ala Ala His Ser Ser Phe Gln Phe Tyr Ser Ser Gly
            245                 250                 255

Val Tyr Tyr Glu Pro Ser Cys Ser Pro Ser Tyr Leu Asp His Ala Val
            260                 265                 270

Leu Ala Val Gly Tyr Gly Ser Glu Gly Gly Gln Asp Phe Trp Leu Val
            275                 280                 285

Lys Asn Ser Trp Ala Thr Ser Trp Gly Asp Ala Gly Tyr Ile Lys Met
            290                 295                 300

Ser Arg Asn Arg Asn Asn Cys Gly Ile Ala Thr Val Ala Ser Tyr
305                 310                 315                 320

Pro Leu Val
```

<210> SEQ ID NO 62
<211> LENGTH: 339
<212> TYPE: PRT
<213> ORGANISM: Sarcophaga cathepsin L

<400> SEQUENCE: 62

```
Met Arg Thr Val Leu Val Ala Leu Leu Ala Leu Val Ala Leu Thr Gln
  1               5                  10                  15

Thr Ile Ser Pro Leu Gln Leu Ile Lys Glu Glu Trp His Thr Tyr Lys
             20                  25                  30

Leu Gln His Arg Lys Asn Tyr Ala Asn Glu Val Glu Glu Arg Phe Arg
         35                  40                  45

Met Lys Ile Phe Asn Glu Asn Arg His Lys Ile Ala Lys His Asn Gln
     50                  55                  60

Leu Phe Ala Gln Gly Lys Val Ser Tyr Lys Leu Gly Leu Asn Lys Tyr
 65                  70                  75                  80

Ala Asp Met Leu His His Glu Phe Lys Glu Thr Met Asn Gly Tyr Asn
                 85                  90                  95

His Thr Leu Arg Gln Leu Met Arg Glu Arg Thr Gly Leu Val Gly Ala
            100                 105                 110

Thr Tyr Ile Pro Pro Ala His Val Thr Val Pro Lys Ser Val Asp Trp
            115                 120                 125

Arg Glu His Gly Ala Val Thr Gly Val Lys Asp Gln Gly His Cys Gly
            130                 135                 140

Ser Cys Trp Ala Phe Ser Ser Thr Gly Ala Leu Glu Gly Gln His Phe
145                 150                 155                 160

Arg Lys Ala Gly Val Leu Val Ser Leu Ser Glu Gln Asn Leu Val Asp
            165                 170                 175

Cys Ser Thr Lys Tyr Gly Asn Asn Gly Cys Asn Gly Gly Leu Met Asp
            180                 185                 190

Asn Ala Phe Arg Tyr Ile Lys Asp Asn Gly Gly Ile Asp Thr Glu Lys
            195                 200                 205

Ser Tyr Pro Tyr Glu Gly Ile Asp Asp Ser Cys His Phe Asn Lys Ala
            210                 215                 220
```

```
Thr Ile Gly Ala Thr Asp Thr Gly Phe Val Asp Ile Pro Glu Gly Asp
225                 230                 235                 240

Glu Glu Lys Met Lys Ala Val Ala Thr Met Gly Pro Val Ser Val
            245                 250                 255

Ala Ile Asp Ala Ser His Glu Ser Phe Gln Leu Tyr Ser Glu Gly Val
                260                 265                 270

Tyr Asn Glu Pro Glu Cys Asp Glu Gln Asn Leu Asp His Gly Val Leu
            275                 280                 285

Val Val Gly Tyr Gly Thr Asp Glu Ser Gly Met Asp Tyr Trp Leu Val
            290                 295                 300

Lys Asn Ser Trp Gly Thr Thr Trp Gly Glu Gln Gly Tyr Ile Lys Met
305                 310                 315                 320

Ala Arg Asn Gln Asn Asn Gln Cys Gly Ile Ala Thr Ala Ser Ser Tyr
                325                 330                 335

Pro Thr Val

<210> SEQ ID NO 63
<211> LENGTH: 344
<212> TYPE: PRT
<213> ORGANISM: silkworm CP

<400> SEQUENCE: 63

Met Lys Cys Leu Val Leu Leu Cys Ala Val Ala Val Ser Ala
1               5                   10                  15

Val Gln Phe Phe Asp Leu Val Lys Glu Glu Trp Ser Ala Phe Lys Leu
                20                  25                  30

Gln His Arg Leu Asn Tyr Lys Ser Glu Val Glu Asp Asn Phe Arg Met
            35                  40                  45

Lys Ile Tyr Ala Glu His Lys His Ile Ile Ala Lys His Asn Gln Lys
50                  55                  60

Tyr Glu Met Gly Leu Val Ser Tyr Lys Leu Gly Met Asn Ser Trp Trp
65                  70                  75                  80

Glu His Gly Asp Met Leu His His Glu Phe Val Lys Thr Met Asn Gly
                85                  90                  95

Phe Asn Lys Thr Ala Lys His Asn Lys Asn Leu Tyr Met Lys Gly Gly
            100                 105                 110

Ser Val Arg Gly Ala Lys Phe Ile Ser Pro Ala Asn Val Lys Leu Pro
        115                 120                 125

Glu Gln Val Asp Trp Arg Lys His Gly Ala Val Thr Asp Ile Lys Asp
    130                 135                 140

Gln Gly Lys Cys Gly Ser Cys Trp Ser Phe Ser Thr Thr Gly Ala Leu
145                 150                 155                 160

Glu Gly Gln His Phe Arg Gln Ser Gly Tyr Leu Val Ser Leu Ser Glu
                165                 170                 175

Gln Asn Leu Ile Asp Cys Ser Glu Gln Tyr Gly Asn Asn Gly Cys Asn
            180                 185                 190

Gly Gly Leu Met Asp Asn Ala Phe Lys Tyr Ile Lys Asp Asn Gly Gly
        195                 200                 205

Ile Asp Thr Glu Gln Ala Tyr Pro Tyr Glu Gly Val Asp Asp Lys Cys
    210                 215                 220

Arg Tyr Asn Pro Lys Asn Thr Gly Ala Glu Asp Val Gly Phe Val Asp
225                 230                 235                 240

Ile Pro Glu Gly Asp Glu Gln Lys Leu Met Glu Ala Val Ala Thr Val
                245                 250                 255
```

```
Gly Pro Val Ser Val Ala Ile Asp Ala Ser His Thr His Phe Gln Leu
            260                 265                 270

Tyr Ser Ser Gly Val Tyr Asn Glu Glu Cys Ser Ser Thr Asp Leu
        275                 280                 285

Asp His Gly Val Leu Val Gly Tyr Gly Thr Asp Glu Gln Gly Val
    290                 295                 300

Asp Tyr Trp Leu Val Lys Asn Ser Trp Gly Arg Ser Trp Gly Glu Leu
305                 310                 315                 320

Gly Tyr Ile Lys Met Ile Arg Asn Lys Asn Asn Arg Cys Gly Ile Ala
                325                 330                 335

Ser Ser Ala Ser Tyr Pro Leu Val
            340

<210> SEQ ID NO 64
<211> LENGTH: 334
<212> TYPE: PRT
<213> ORGANISM: Murine cathepsin L

<400> SEQUENCE: 64

Met Asn Leu Leu Leu Leu Leu Ala Val Leu Cys Leu Gly Thr Ala Leu
 1               5                  10                  15

Ala Thr Pro Lys Phe Asp Gln Thr Phe Ser Ala Glu Trp His Gln Trp
             20                  25                  30

Lys Ser Thr His Arg Arg Leu Tyr Gly Thr Asn Glu Glu Glu Trp Arg
         35                  40                  45

Arg Ala Ile Trp Glu Lys Asn Met Arg Ile Ile Gln Leu His Asn Gly
     50                  55                  60

Glu Tyr Ser Asn Gly Gln His Gly Phe Ser Met Glu Met Asn Ala Phe
 65                  70                  75                  80

Gly Asp Met Thr Asn Glu Glu Phe Arg Gln Val Val Asn Gly Tyr Arg
                 85                  90                  95

His Gln Lys His Lys Lys Gly Arg Leu Phe Gln Glu Pro Leu Met Leu
            100                 105                 110

Lys Ile Pro Lys Ser Val Asp Trp Arg Glu Lys Gly Cys Val Thr Pro
        115                 120                 125

Val Lys Asn Gln Gly Gln Cys Gly Ser Cys Trp Ala Phe Ser Ala Ser
130                 135                 140

Gly Cys Leu Glu Gly Gln Met Phe Leu Lys Thr Gly Lys Leu Ile Ser
145                 150                 155                 160

Leu Ser Glu Gln Asn Leu Val Asp Cys Ser His Ala Gln Gly Asn Gln
                165                 170                 175

Gly Cys Asn Gly Gly Leu Met Asp Phe Ala Phe Gln Tyr Ile Lys Glu
            180                 185                 190

Asn Gly Gly Leu Asp Ser Glu Glu Ser Tyr Pro Tyr Glu Ala Lys Asp
        195                 200                 205

Gly Ser Cys Lys Tyr Arg Ala Glu Phe Ala Val Ala Asn Asp Thr Gly
    210                 215                 220

Phe Val Asp Ile Pro Gln Gln Glu Lys Ala Leu Met Lys Ala Val Ala
225                 230                 235                 240

Thr Val Gly Pro Ile Ser Val Ala Met Asp Ala Ser His Pro Ser Leu
                245                 250                 255

Gln Phe Tyr Ser Ser Gly Ile Tyr Tyr Glu Pro Asn Cys Ser Ser Lys
            260                 265                 270

Asn Leu Asp His Gly Val Leu Val Gly Tyr Gly Tyr Glu Gly Thr
        275                 280                 285
```

```
Asp Ser Asn Lys Asn Lys Tyr Trp Leu Val Lys Asn Ser Trp Gly Ser
        290                 295                 300

Glu Trp Gly Met Glu Gly Tyr Ile Lys Ile Ala Lys Asp Arg Asp Asn
305                 310                 315                 320

His Cys Gly Leu Ala Thr Ala Ala Ser Tyr Pro Val Val Asn
                325                 330

<210> SEQ ID NO 65
<211> LENGTH: 333
<212> TYPE: PRT
<213> ORGANISM: Homo sapiens cathepsin L

<400> SEQUENCE: 65

Met Asn Pro Thr Leu Ile Leu Ala Ala Phe Cys Leu Gly Ile Ala Ser
  1               5                  10                  15

Ala Thr Leu Thr Phe Asp His Ser Leu Glu Ala Gln Trp Thr Lys Trp
                 20                  25                  30

Lys Ala Met His Asn Arg Leu Tyr Gly Met Asn Glu Glu Gly Trp Arg
             35                  40                  45

Arg Ala Val Trp Glu Lys Asn Met Lys Met Ile Glu Leu His Asn Gln
         50                  55                  60

Glu Tyr Arg Glu Gly Lys His Ser Phe Thr Met Ala Met Asn Ala Phe
 65                  70                  75                  80

Gly Asp Met Thr Ser Glu Glu Phe Arg Gln Val Met Asn Gly Phe Gln
                 85                  90                  95

Asn Arg Lys Pro Arg Lys Gly Lys Val Phe Gln Glu Pro Leu Phe Tyr
                100                 105                 110

Glu Ala Pro Arg Ser Val Asp Trp Arg Glu Lys Gly Tyr Val Thr Pro
            115                 120                 125

Val Lys Asn Gln Gly Gln Cys Gly Ser Cys Trp Ala Phe Ser Ala Thr
        130                 135                 140

Gly Ala Leu Glu Gly Gln Met Phe Arg Lys Thr Gly Arg Leu Ile Ser
145                 150                 155                 160

Leu Ser Glu Gln Asn Leu Val Asp Cys Ser Gly Pro Gln Gly Asn Glu
                165                 170                 175

Gly Cys Asn Gly Gly Leu Met Asp Tyr Ala Phe Gln Tyr Val Gln Asp
            180                 185                 190

Asn Gly Gly Leu Asp Ser Glu Glu Ser Tyr Pro Tyr Glu Ala Thr Glu
        195                 200                 205

Glu Ser Cys Lys Tyr Asn Pro Lys Tyr Ser Val Ala Asn Asp Thr Gly
    210                 215                 220

Phe Val Asp Ile Pro Lys Gln Glu Lys Ala Leu Met Lys Ala Val Ala
225                 230                 235                 240

Thr Val Gly Pro Ile Ser Val Ala Ile Asp Ala Gly His Glu Ser Phe
                245                 250                 255

Leu Phe Tyr Lys Glu Gly Ile Tyr Phe Glu Pro Asp Cys Ser Ser Glu
            260                 265                 270

Asp Met Asp His Gly Val Leu Val Val Gly Tyr Gly Phe Glu Ser Thr
        275                 280                 285

Glu Ser Asp Asn Asn Lys Tyr Trp Leu Val Lys Asn Ser Trp Gly Glu
    290                 295                 300

Glu Trp Gly Met Gly Gly Tyr Val Lys Met Ala Lys Asp Arg Arg Asn
305                 310                 315                 320

His Cys Gly Ile Ala Ser Ala Ala Ser Tyr Pro Thr Val
                325                 330
```

<210> SEQ ID NO 66
<211> LENGTH: 335
<212> TYPE: PRT
<213> ORGANISM: Homo sapien cathepsin H

<400> SEQUENCE: 66

```
Met Trp Ala Thr Leu Pro Leu Leu Cys Ala Gly Ala Trp Leu Leu Gly
  1               5                  10                  15
Val Pro Val Cys Gly Ala Ala Glu Leu Ser Val Asn Ser Leu Glu Lys
             20                  25                  30
Phe His Phe Lys Ser Trp Met Ser Lys His Arg Lys Thr Tyr Ser Thr
         35                  40                  45
Glu Glu Tyr His His Arg Leu Gln Thr Phe Ala Ser Asn Trp Arg Lys
     50                  55                  60
Ile Asn Ala His Asn Asn Gly Asn His Thr Phe Lys Met Ala Leu Asn
 65                  70                  75                  80
Gln Phe Ser Asp Met Ser Phe Ala Glu Ile Lys His Lys Tyr Leu Trp
                 85                  90                  95
Ser Glu Pro Gln Asn Cys Ser Ala Thr Lys Ser Asn Tyr Leu Arg Gly
            100                 105                 110
Thr Gly Pro Tyr Pro Pro Ser Val Asp Trp Arg Lys Lys Gly Asn Phe
        115                 120                 125
Val Ser Pro Val Lys Asn Gln Gly Ala Cys Gly Ser Cys Trp Thr Phe
    130                 135                 140
Ser Thr Thr Gly Ala Leu Glu Ser Ala Ile Ala Ile Ala Thr Gly Lys
145                 150                 155                 160
Met Leu Ser Leu Ala Glu Gln Gln Leu Val Asp Cys Ala Gln Asp Phe
                165                 170                 175
Asn Asn Tyr Gly Cys Gln Gly Gly Leu Pro Ser Gln Ala Phe Glu Tyr
            180                 185                 190
Ile Leu Tyr Asn Lys Gly Ile Met Gly Glu Asp Thr Tyr Pro Tyr Gln
        195                 200                 205
Gly Lys Asp Gly Tyr Cys Lys Phe Gln Pro Gly Lys Ala Ile Gly Phe
    210                 215                 220
Val Lys Asp Val Ala Asn Ile Thr Ile Tyr Asp Glu Glu Ala Met Val
225                 230                 235                 240
Glu Ala Val Ala Leu Tyr Asn Pro Val Ser Phe Ala Phe Glu Val Thr
                245                 250                 255
Gln Asp Phe Met Met Tyr Arg Thr Gly Ile Tyr Ser Ser Thr Ser Cys
            260                 265                 270
His Lys Thr Pro Asp Lys Val Asn His Ala Val Leu Ala Val Gly Tyr
        275                 280                 285
Gly Glu Lys Asn Gly Ile Pro Tyr Trp Ile Val Lys Asn Ser Trp Gly
    290                 295                 300
Pro Gln Trp Gly Met Asn Gly Tyr Phe Leu Ile Glu Arg Gly Lys Asn
305                 310                 315                 320
Met Cys Gly Leu Ala Ala Cys Ala Ser Tyr Pro Ile Pro Leu Val
                325                 330                 335
```

<210> SEQ ID NO 67
<211> LENGTH: 326
<212> TYPE: PRT
<213> ORGANISM: Fasciola hepatica -continued

```
<400> SEQUENCE: 67

Met Arg Leu Phe Ile Leu Ala Val Leu Thr Val Gly Val Leu Gly Ser
 1               5                  10                  15

Asn Asp Asp Leu Trp His Gln Trp Lys Arg Met Tyr Asn Lys Glu Tyr
            20                  25                  30

Asn Gly Ala Asp Asp Gln His Arg Arg Asn Ile Trp Glu Lys Asn Val
        35                  40                  45

Lys His Ile Gln Glu His Asn Leu Arg His Asp Leu Gly Leu Val Thr
    50                  55                  60

Tyr Thr Leu Gly Leu Asn Gln Phe Thr Asp Met Thr Phe Glu Glu Phe
 65                  70                  75                  80

Lys Ala Lys Tyr Leu Thr Glu Met Ser Arg Ala Ser Asp Ile Leu Ser
                85                  90                  95

His Gly Val Pro Tyr Glu Ala Asn Asn Arg Ala Val Pro Asp Lys Ile
            100                 105                 110

Asp Trp Arg Glu Ser Gly Tyr Val Thr Glu Val Lys Asp Gln Gly Asn
        115                 120                 125

Cys Gly Ser Cys Trp Ala Phe Ser Thr Thr Gly Thr Met Glu Gly Gln
    130                 135                 140

Tyr Met Lys Asn Glu Arg Thr Ser Ile Ser Phe Ser Glu Gln Gln Leu
145                 150                 155                 160

Val Asp Cys Ser Gly Pro Trp Gly Asn Asn Gly Cys Ser Gly Gly Leu
                165                 170                 175

Met Glu Asn Ala Tyr Gln Tyr Leu Lys Gln Phe Gly Leu Glu Thr Glu
            180                 185                 190

Ser Ser Tyr Pro Tyr Thr Ala Val Glu Gly Gln Cys Arg Tyr Asn Lys
        195                 200                 205

Gln Leu Gly Val Ala Lys Val Thr Gly Tyr Tyr Thr Val His Ser Gly
    210                 215                 220

Ser Glu Val Glu Leu Lys Asn Leu Val Gly Ala Arg Arg Pro Ala Ala
225                 230                 235                 240

Val Ala Val Asp Val Glu Ser Asp Phe Met Met Tyr Arg Ser Gly Ile
                245                 250                 255

Tyr Gln Ser Gln Thr Cys Ser Pro Leu Arg Val Asn His Ala Val Leu
            260                 265                 270

Ala Val Gly Tyr Gly Thr Gln Gly Gly Thr Asp Tyr Trp Ile Val Lys
        275                 280                 285

Asn Ser Trp Gly Thr Tyr Trp Gly Glu Arg Gly Tyr Ile Arg Met Ala
    290                 295                 300

Arg Asn Arg Gly Asn Met Cys Gly Ile Ala Ser Leu Ala Ser Leu Pro
305                 310                 315                 320

Met Val Ala Arg Phe Pro
                325

<210> SEQ ID NO 68
<211> LENGTH: 450
<212> TYPE: PRT
<213> ORGANISM: Tripanosoma

<400> SEQUENCE: 68

Met Pro Arg Thr Glu Met Val Arg Phe Val Arg Leu Pro Val Val Leu
 1               5                  10                  15

Leu Ala Met Ala Ala Cys Leu Ala Ser Val Ala Leu Gly Ser Leu His
            20                  25                  30
```

-continued

```
Val Glu Glu Ser Leu Glu Met Arg Phe Ala Ala Phe Lys Lys Lys Tyr
        35                  40                  45

Gly Lys Val Tyr Lys Asp Ala Lys Glu Glu Ala Phe Arg Phe Arg Ala
        50                  55                  60

Phe Glu Glu Asn Met Glu Gln Ala Lys Ile Gln Ala Ala Asn Pro
 65                  70                  75                  80

Tyr Ala Thr Phe Gly Val Thr Pro Phe Ser Asp Met Thr Arg Glu Glu
                85                  90                  95

Phe Arg Ala Arg Tyr Arg Asn Gly Ala Ser Tyr Phe Ala Ala Ala Gln
                100                 105                 110

Lys Arg Leu Arg Lys Thr Val Asn Val Thr Thr Gly Arg Ala Pro Ala
        115                 120                 125

Ala Val Asp Trp Arg Glu Lys Gly Ala Val Thr Pro Val Lys Val Gln
        130                 135                 140

Gly Gln Cys Gly Ser Cys Trp Ala Phe Ser Thr Ile Gly Asn Ile Glu
145                 150                 155                 160

Gly Gln Trp Gln Val Ala Gly Asn Pro Leu Val Ser Leu Ser Glu Gln
                165                 170                 175

Met Leu Val Ser Cys Asp Thr Ile Asp Ser Gly Cys Asn Gly Gly Leu
                180                 185                 190

Met Asp Asn Ala Phe Asn Trp Ile Val Asn Ser Asn Gly Gly Asn Val
        195                 200                 205

Phe Thr Glu Ala Ser Tyr Pro Tyr Val Ser Gly Asn Gly Glu Gln Pro
210                 215                 220

Gln Cys Gln Met Asn Gly His Glu Ile Gly Ala Ala Ile Thr Asp His
225                 230                 235                 240

Val Asp Leu Pro Gln Asp Glu Asp Ala Ile Ala Ala Tyr Leu Ala Glu
                245                 250                 255

Asn Gly Pro Leu Ala Ile Ala Val Asp Ala Glu Ser Phe Met Asp Tyr
        260                 265                 270

Asn Gly Gly Ile Leu Thr Ser Cys Thr Ser Lys Gln Leu Asp His Gly
        275                 280                 285

Val Leu Leu Val Gly Tyr Asn Asp Ser Asn Pro Pro Tyr Trp Ile
        290                 295                 300

Ile Lys Asn Ser Trp Ser Asn Met Trp Gly Glu Asp Gly Tyr Ile Arg
305                 310                 315                 320

Ile Glu Lys Gly Thr Asn Gln Cys Leu Met Asn Gln Ala Val Ser Ser
                325                 330                 335

Ala Val Val Gly Gly Pro Thr Pro Pro Pro Pro Pro Pro Pro
                340                 345                 350

Ser Ala Thr Phe Thr Gln Asp Phe Cys Glu Gly Lys Gly Cys Thr Lys
        355                 360                 365

Gly Cys Ser His Ala Thr Phe Pro Thr Gly Glu Cys Val Gln Thr Thr
        370                 375                 380

Gly Val Gly Ser Val Ile Ala Thr Cys Gly Ala Ser Asn Leu Thr Gln
385                 390                 395                 400

Ile Ile Tyr Pro Leu Ser Arg Ser Cys Ser Gly Pro Ser Val Pro Ile
                405                 410                 415

Thr Val Pro Leu Asp Lys Cys Ile Pro Ile Leu Ile Gly Ser Val Glu
                420                 425                 430

Tyr His Cys Ser Thr Asn Pro Pro Thr Lys Ala Ala Arg Leu Val Pro
        435                 440                 445

His Gln
```

450

<210> SEQ ID NO 69
<211> LENGTH: 443
<212> TYPE: PRT
<213> ORGANISM: Leishmania

<400> SEQUENCE: 69

```
Met Ala Thr Ser Arg Ala Ala Leu Cys Ala Val Ala Val Val Cys Val
 1               5                  10                  15

Val Leu Ala Val Ala Cys Ala Pro Ala Arg Ala Ile Tyr Val Gly Thr
             20                  25                  30

Pro Ala Ala Ala Leu Phe Glu Glu Phe Lys Arg Thr Tyr Gln Arg Ala
         35                  40                  45

Tyr Gly Thr Leu Thr Glu Glu Gln Arg Leu Ala Asn Phe Glu Arg
 50                  55                  60

Asn Leu Glu Leu Met Arg Glu His Gln Ala Arg Asn Pro His Ala Arg
 65                  70                  75                  80

Phe Gly Ile Thr Lys Phe Phe Asp Leu Ser Glu Ala Glu Phe Ala Ala
                 85                  90                  95

Arg Tyr Leu Asn Gly Ala Ala Tyr Phe Ala Ala Lys Gln His Ala
            100                 105                 110

Gly Gln His Tyr Arg Lys Ala Arg Ala Asp Leu Ser Ala Val Pro Asp
        115                 120                 125

Ala Val Asp Trp Arg Glu Lys Gly Ala Val Thr Pro Val Lys Asn Gln
    130                 135                 140

Gly Ala Cys Gly Ser Cys Trp Ala Phe Ser Ala Val Gly Asn Ile Glu
145                 150                 155                 160

Ser Gln Trp Ala Val Ala Gly His Lys Leu Val Arg Leu Ser Glu Gln
                165                 170                 175

Gln Leu Val Ser Cys Asp His Val Asp Asn Gly Cys Gly Gly Gly Leu
            180                 185                 190

Met Leu Gln Ala Phe Glu Trp Val Leu Arg Asn Met Asn Gly Thr Val
        195                 200                 205

Phe Thr Glu Lys Ser Tyr Pro Tyr Val Ser Gly Asn Gly Asp Val Pro
    210                 215                 220

Glu Cys Ser Asn Ser Ser Glu Leu Ala Pro Gly Ala Arg Ile Asp Gly
225                 230                 235                 240

Tyr Val Ser Met Glu Ser Ser Glu Arg Val Met Ala Ala Trp Leu Ala
                245                 250                 255

Lys Asn Gly Pro Ile Ser Ile Ala Val Asp Ala Ser Ser Phe Met Ser
            260                 265                 270

Tyr His Ser Gly Val Leu Thr Ser Cys Ile Gly Glu Gln Leu Asn His
        275                 280                 285

Gly Val Leu Leu Val Gly Tyr Asn Met Thr Gly Glu Val Pro Tyr Trp
    290                 295                 300

Val Ile Lys Asn Ser Trp Gly Glu Asp Trp Gly Glu Lys Gly Tyr Val
305                 310                 315                 320

Arg Val Thr Met Gly Val Asn Ala Cys Leu Leu Thr Gly Tyr Pro Val
                325                 330                 335

Ser Val His Val Ser Gln Ser Pro Thr Pro Gly Pro Asn Thr Thr Thr
            340                 345                 350

Thr Thr His Ala Pro Lys Arg Val Thr Val Lys Gln Ile Thr Cys Thr
        355                 360                 365
```

-continued

```
Asp Tyr Phe Cys Arg Lys Gly Cys Lys Thr Thr Val Ile Pro Thr Lys
    370                 375                 380

Glu Cys Leu Pro Asn Gly Ala Gly Gly Ser Phe Gln Met Glu Cys Gly
385                 390                 395                 400

Asp His Gln Val Leu Lys Leu Thr Tyr Thr Ser Met Asn Cys Thr Gly
                    405                 410                 415

Glu Ala Lys Tyr Thr Val Thr Arg Glu Gly Lys Cys Gly Ile Ser Trp
                420                 425                 430

Ser Gly Ser Ser Lys Ser Ile Cys Gln Tyr Val
            435                 440

<210> SEQ ID NO 70
<211> LENGTH: 336
<212> TYPE: PRT
<213> ORGANISM: Tetrahimena

<400> SEQUENCE: 70

Met Asn Lys Lys Phe Ile Ile Leu Ser Ile Ile Met Leu Met Pro Leu
  1               5                  10                  15

Cys Leu Ala Gln Asp Ile Ser Val Glu Lys Leu Leu Ala Tyr Asn Lys
                 20                  25                  30

Trp Ser Ser Gln Asn Gln Arg Ala Tyr Leu Asn Glu Asp Glu Lys Leu
             35                  40                  45

Tyr Arg Gln Ile Val Phe Phe Glu Asn Leu Gln Lys Ile Lys Glu His
     50                  55                  60

Asn Ser Asn Pro Asn Asn Thr Tyr Ser Ile His Leu Asn Gln Phe Ser
 65                  70                  75                  80

Asp Met Thr Arg Glu Glu Phe Ala Glu Lys Ile Leu Met Lys Gln Asp
                 85                  90                  95

Leu Ile Asn Asp Tyr Met Lys Gly Ile Gly Gln Gln Ala Thr His Asn
                100                 105                 110

Asn Ala Asn Asn Glu Thr Gln Met Asn Ser Gln Asn His Thr Leu Ala
             115                 120                 125

Ala Ser Ile Asp Trp Arg Thr Lys Gly Ala Val Thr Ser Val Lys Asp
    130                 135                 140

Gln Gly Gln Cys Gly Ser Cys Trp Ser Phe Ser Ala Ala Ala Leu Met
145                 150                 155                 160

Glu Ser Phe Asn Phe Ile Gln Asn Lys Ala Leu Val Asn Phe Ser Glu
                165                 170                 175

Gln Gln Leu Val Asp Cys Val Thr Pro Glu Asn Gly Tyr Pro Ser Tyr
                180                 185                 190

Gly Cys Lys Gly Gly Trp Pro Ala Thr Cys Leu Asp Tyr Ala Ser Lys
            195                 200                 205

Val Gly Ile Thr Thr Leu Asp Lys Tyr Pro Tyr Val Ala Val Gln Lys
    210                 215                 220

Asn Cys Thr Val Thr Gly Thr Asn Gly Phe Lys Leu Lys Lys Trp
225                 230                 235                 240

Ile Val Ile Pro Asn Thr Ser Asn Asp Leu Lys Ser Ala Leu Asn Phe
                245                 250                 255

Ser Pro Val Ser Val Leu Val Asp Ala Thr Asn Trp Asp Tyr Tyr Ser
                260                 265                 270

Ser Gly Ile Phe Asn Gly Cys Asn Gln Thr Asn Ile Asn Leu Asn His
            275                 280                 285

Ala Val Leu Ala Val Gly Tyr Asp Glu Lys Asp Asn Trp Ile Val Lys
    290                 295                 300
```

```
Asn Ser Trp Ser Ala Gly Trp Gly Glu His Gly Tyr Ile Arg Leu Ala
305                 310                 315                 320

Pro Asn Asn Thr Cys Gly Ile Leu Ser Ser Asn Ile Gln Val Thr Ala
            325                 330                 335

<210> SEQ ID NO 71
<211> LENGTH: 343
<212> TYPE: PRT
<213> ORGANISM: Dictyostelium

<400> SEQUENCE: 71

Met Lys Val Ile Leu Leu Phe Val Leu Ala Val Phe Thr Val Phe Val
1               5                   10                  15

Ser Ser Arg Gly Ile Pro Pro Glu Glu Gln Ser Gln Phe Leu Glu Phe
                20                  25                  30

Gln Asp Lys Phe Asn Lys Lys Tyr Ser His Glu Glu Tyr Leu Glu Arg
            35                  40                  45

Phe Glu Ile Phe Lys Ser Asn Leu Gly Lys Ile Glu Glu Leu Asn Leu
        50                  55                  60

Ile Ala Ile Asn His Lys Ala Asp Thr Lys Phe Gly Val Asn Lys Phe
65                  70                  75                  80

Ala Asp Leu Ser Ser Asp Glu Phe Lys Asn Tyr Tyr Leu Asn Asn Lys
                85                  90                  95

Glu Ala Ile Phe Thr Asp Asp Leu Pro Val Ala Asp Tyr Leu Asp Asp
            100                 105                 110

Glu Phe Ile Asn Ser Ile Pro Thr Ala Phe Asp Trp Arg Thr Arg Gly
        115                 120                 125

Ala Val Thr Pro Val Lys Asn Gln Gly Gln Cys Gly Ser Cys Trp Ser
130                 135                 140

Phe Ser Thr Thr Gly Asn Val Glu Gly Gln His Phe Ile Ser Gln Asn
145                 150                 155                 160

Lys Leu Val Ser Leu Ser Glu Gln Asn Leu Val Asp Cys Asp His Glu
                165                 170                 175

Cys Met Glu Tyr Glu Gly Glu Glu Ala Cys Asp Glu Gly Cys Asn Gly
            180                 185                 190

Gly Leu Gln Pro Asn Ala Tyr Asn Tyr Ile Ile Lys Asn Gly Gly Ile
        195                 200                 205

Gln Thr Glu Ser Ser Tyr Pro Tyr Thr Ala Glu Thr Gly Thr Gln Cys
210                 215                 220

Asn Phe Asn Ser Ala Asn Ile Gly Ala Lys Ile Ser Asn Phe Thr Met
225                 230                 235                 240

Ile Pro Lys Asn Glu Thr Val Met Ala Gly Tyr Ile Val Ser Thr Gly
                245                 250                 255

Pro Leu Ala Ile Ala Ala Asp Ala Val Glu Trp Gln Phe Tyr Ile Gly
            260                 265                 270

Gly Val Phe Asp Ile Pro Cys Asn Pro Asn Ser Leu Asp His Gly Ile
        275                 280                 285

Leu Ile Val Gly Tyr Ser Ala Lys Asn Thr Ile Phe Arg Lys Asn Met
290                 295                 300

Pro Tyr Trp Ile Val Lys Asn Ser Trp Gly Ala Asp Trp Gly Glu Gln
305                 310                 315                 320

Gly Tyr Ile Tyr Leu Arg Arg Gly Lys Asn Thr Cys Gly Val Ser Asn
                325                 330                 335

Phe Val Ser Thr Ser Ile Ile
```

340

<210> SEQ ID NO 72
<211> LENGTH: 457
<212> TYPE: PRT
<213> ORGANISM: Oryzain

<400> SEQUENCE: 72

| Met | Arg | Ile | Ser | Met | Ala | Leu | Ala | Ala | Ala | Leu | Leu | Leu | Leu |
| 1 | | | | 5 | | | | | 10 | | | | 15 |

| Ser | Leu | Ala | Ala | Ala | Asp | Met | Ser | Ile | Val | Ser | Tyr | Gly | Glu | Arg | Ser |
| | | | 20 | | | | | 25 | | | | | 30 | | |

Glu Glu Glu Ala Arg Arg Leu Tyr Ala Glu Trp Lys Ala Glu His Gly
            35                  40                  45

Lys Ser Tyr Asn Ala Val Gly Glu Glu Arg Arg Tyr Ala Ala Phe
     50                  55                  60

Arg Asp Asn Leu Arg Tyr Ile Asp Glu His Asn Ala Ala Ala Asp Ala
 65                  70                  75                  80

Gly Val His Ser Phe Arg Leu Gly Leu Asn Arg Phe Ala Asp Leu Thr
                85                  90                  95

Asn Glu Glu Tyr Arg Asp Thr Tyr Leu Gly Leu Arg Asn Lys Pro Arg
            100                 105                 110

Arg Glu Arg Lys Val Ser Asp Arg Tyr Leu Ala Ala Asp Asn Glu Ala
        115                 120                 125

Leu Pro Glu Ser Val Asp Trp Arg Thr Lys Gly Ala Val Ala Glu Ile
    130                 135                 140

Lys Asp Gln Gly Gly Cys Gly Ser Cys Trp Ala Phe Ser Ala Ile Ala
145                 150                 155                 160

Ala Val Glu Asp Ile Asn Gln Ile Val Thr Gly Asp Leu Ile Ser Leu
                165                 170                 175

Ser Glu Gln Glu Leu Val Asp Cys Asp Thr Ser Tyr Asn Glu Gly Cys
            180                 185                 190

Asn Gly Gly Leu Met Asp Tyr Ala Phe Asp Phe Ile Ile Asn Asn Gly
        195                 200                 205

Gly Ile Asp Thr Glu Asp Asp Tyr Pro Tyr Lys Gly Lys Asp Glu Arg
    210                 215                 220

Cys Asp Val Asn Arg Lys Asn Ala Lys Val Val Thr Ile Asp Ser Tyr
225                 230                 235                 240

Glu Asp Val Thr Pro Asn Ser Glu Thr Ser Leu Gln Lys Ala Val Arg
                245                 250                 255

Asn Gln Pro Val Ser Val Ala Ile Glu Ala Gly Gly Arg Ala Phe Gln
            260                 265                 270

Leu Tyr Ser Ser Gly Ile Phe Thr Gly Lys Cys Gly Thr Ala Leu Asp
        275                 280                 285

His Gly Val Ala Val Gly Tyr Gly Thr Glu Asn Gly Lys Asp Tyr
    290                 295                 300

Trp Ile Val Arg Asn Ser Trp Gly Lys Ser Trp Gly Glu Ser Gly Tyr
305                 310                 315                 320

Val Arg Met Glu Arg Asn Ile Lys Ala Ser Ser Gly Lys Cys Gly Ile
                325                 330                 335

Ala Val Glu Pro Ser Tyr Pro Leu Lys Lys Gly Glu Asn Pro Pro Asn
            340                 345                 350

Pro Gly Pro Thr Pro Ser Pro Thr Pro Pro Thr Val Cys Asp Asn
        355                 360                 365

```
Tyr Tyr Thr Cys Pro Asp Ser Thr Thr Cys Cys Cys Ile Tyr Glu Tyr
    370                 375                 380

Gly Lys Tyr Cys Tyr Ala Trp Gly Cys Cys Pro Leu Glu Gly Ala Thr
385                 390                 395                 400

Cys Cys Asp Asp His Tyr Ser Cys Cys Pro His Glu Tyr Pro Ile Cys
                405                 410                 415

Asn Val Gln Gln Gly Thr Cys Leu Met Ala Lys Asp Ser Pro Leu Ala
            420                 425                 430

Val Lys Ala Leu Lys Arg Thr Leu Ala Lys Pro Asn Leu Ser Phe Leu
        435                 440                 445

Phe Gly Asn Gly Lys Lys Ser Ser Ala
    450                 455

<210> SEQ ID NO 73
<211> LENGTH: 345
<212> TYPE: PRT
<213> ORGANISM: Papain

<400> SEQUENCE: 73

Met Ala Met Ile Pro Ser Ile Ser Lys Leu Leu Phe Val Ala Ile Cys
1               5                   10                  15

Leu Phe Val Tyr Met Gly Leu Ser Phe Gly Asp Phe Ser Ile Val Gly
            20                  25                  30

Tyr Ser Gln Asn Asp Leu Thr Ser Thr Glu Arg Leu Ile Gln Leu Phe
        35                  40                  45

Glu Ser Trp Met Leu Lys His Asn Lys Ile Tyr Lys Asn Ile Asp Glu
    50                  55                  60

Lys Ile Tyr Arg Phe Glu Ile Phe Lys Asp Asn Leu Lys Tyr Ile Asp
65                  70                  75                  80

Glu Thr Asn Lys Lys Asn Asn Ser Tyr Trp Leu Gly Leu Asn Val Phe
                85                  90                  95

Ala Asp Met Ser Asn Asp Glu Phe Lys Glu Lys Tyr Thr Gly Ser Ile
            100                 105                 110

Ala Gly Asn Tyr Thr Thr Thr Glu Leu Ser Tyr Glu Glu Val Leu Asn
        115                 120                 125

Asp Gly Asp Val Asn Ile Pro Glu Tyr Val Asp Trp Arg Gln Lys Gly
    130                 135                 140

Ala Val Thr Pro Val Lys Asn Gln Gly Ser Cys Gly Ser Cys Trp Ala
145                 150                 155                 160

Phe Ser Ala Val Val Thr Ile Glu Gly Ile Ile Lys Ile Arg Thr Gly
                165                 170                 175

Asn Leu Asn Glu Tyr Ser Glu Gln Glu Leu Leu Asp Cys Asp Arg Arg
            180                 185                 190

Ser Tyr Gly Cys Asn Gly Gly Tyr Pro Trp Ser Ala Leu Gln Leu Val
        195                 200                 205

Ala Gln Tyr Gly Ile His Tyr Arg Asn Thr Tyr Pro Tyr Glu Gly Val
    210                 215                 220

Gln Arg Tyr Cys Arg Ser Arg Glu Lys Gly Pro Tyr Ala Ala Lys Thr
225                 230                 235                 240

Asp Gly Val Arg Gln Val Gln Pro Tyr Asn Glu Gly Ala Leu Leu Tyr
                245                 250                 255

Ser Ile Ala Asn Gln Pro Val Ser Val Val Leu Glu Ala Ala Gly Lys
            260                 265                 270

Asp Phe Gln Leu Tyr Arg Gly Gly Ile Phe Val Gly Pro Cys Gly Asn
        275                 280                 285
```

```
Lys Val Asp His Ala Val Ala Val Gly Tyr Gly Pro Asn Tyr Ile
    290                 295                 300

Leu Ile Lys Asn Ser Trp Gly Thr Gly Trp Gly Glu Asn Gly Tyr Ile
305                 310                 315                 320

Arg Ile Lys Arg Gly Thr Gly Asn Ser Tyr Gly Val Cys Gly Leu Tyr
                325                 330                 335

Thr Ser Ser Phe Tyr Pro Val Lys Asn
                340                 345

<210> SEQ ID NO 74
<211> LENGTH: 362
<212> TYPE: PRT
<213> ORGANISM: Vigna mungo CP

<400> SEQUENCE: 74

Met Ala Met Lys Lys Leu Leu Trp Val Val Leu Ser Leu Ser Leu Val
  1               5                  10                  15

Leu Gly Val Ala Asn Ser Phe Asp Phe His Glu Lys Asp Leu Glu Ser
                 20                  25                  30

Glu Glu Ser Leu Trp Asp Leu Tyr Glu Arg Trp Arg Ser His His Thr
             35                  40                  45

Val Ser Arg Ser Leu Gly Glu Lys His Lys Arg Phe Asn Val Phe Lys
 50                  55                  60

Ala Asn Val Met His Val His Asn Thr Asn Lys Met Asp Lys Pro Tyr
 65                  70                  75                  80

Lys Leu Lys Leu Asn Lys Phe Ala Asp Met Thr Asn His Glu Phe Arg
                 85                  90                  95

Ser Thr Tyr Ala Gly Ser Lys Val Asn His His Lys Met Phe Arg Gly
            100                 105                 110

Ser Gln His Gly Ser Gly Thr Phe Met Tyr Glu Lys Val Gly Ser Val
            115                 120                 125

Pro Ala Ser Val Asp Trp Arg Lys Lys Gly Ala Val Thr Asp Val Lys
130                 135                 140

Asp Gln Gly Gln Cys Gly Ser Cys Trp Ala Phe Ser Thr Ile Val Ala
145                 150                 155                 160

Val Glu Gly Ile Asn Gln Ile Lys Thr Asn Lys Leu Val Ser Leu Ser
                165                 170                 175

Glu Gln Glu Leu Val Asp Cys Asp Lys Glu Glu Asn Gln Gly Cys Asn
            180                 185                 190

Gly Gly Leu Met Glu Ser Ala Phe Glu Phe Ile Lys Gln Lys Gly Gly
            195                 200                 205

Ile Thr Thr Glu Ser Asn Tyr Pro Tyr Thr Ala Gln Glu Gly Thr Cys
            210                 215                 220

Asp Glu Ser Lys Val Asn Asp Leu Ala Val Ser Ile Asp Gly His Glu
225                 230                 235                 240

Asn Val Pro Val Asn Asp Glu Asn Ala Leu Leu Lys Ala Val Ala Asn
                245                 250                 255

Gln Pro Val Ser Val Ala Ile Asp Ala Gly Gly Ser Asp Phe Gln Phe
            260                 265                 270

Tyr Ser Glu Gly Val Phe Thr Gly Asp Cys Asn Thr Asp Leu Asn His
            275                 280                 285

Gly Val Ala Ile Val Gly Tyr Gly Thr Thr Val Asp Gly Thr Asn Tyr
            290                 295                 300

Trp Ile Val Arg Asn Ser Trp Gly Pro Glu Trp Gly Glu Gln Gly Tyr
```

```
                         305                 310                 315                 320
Ile Arg Met Gln Arg Asn Ile Ser Lys Lys Glu Gly Leu Cys Gly Ile
                    325                 330                 335
Ala Met Met Ala Ser Tyr Pro Ile Lys Asn Ser Ser Asp Asn Pro Thr
                340                 345                 350
Gly Ser Leu Ser Ser Pro Lys Asp Glu Leu
            355                 360

<210> SEQ ID NO 75
<211> LENGTH: 361
<212> TYPE: PRT
<213> ORGANISM: Aleurain

<400> SEQUENCE: 75

Met Ala His Ala Arg Val Leu Leu Ala Leu Ala Val Leu Ala Thr
  1               5                  10                  15
Ala Ala Val Ala Val Ala Ser Ser Ser Phe Ala Asp Ser Asn Pro
                 20                  25                  30
Ile Arg Pro Val Thr Asp Arg Ala Ala Ser Thr Leu Glu Ser Ala Val
                 35                  40                  45
Leu Gly Ala Leu Gly Arg Thr Arg His Ala Leu Arg Phe Ala Arg Phe
     50                  55                  60
Ala Val Arg Tyr Gly Lys Ser Tyr Glu Ser Ala Ala Glu Val Arg Arg
 65                  70                  75                  80
Arg Phe Arg Ile Phe Ser Glu Ser Leu Glu Glu Val Arg Ser Thr Asn
                 85                  90                  95
Arg Lys Gly Leu Pro Tyr Arg Leu Gly Ile Asn Arg Phe Ser Asp Met
                100                 105                 110
Ser Trp Glu Glu Phe Gln Ala Thr Arg Leu Gly Ala Ala Gln Thr Cys
                115                 120                 125
Ser Ala Thr Leu Ala Gly Asn His Leu Met Arg Asp Ala Ala Ala Leu
            130                 135                 140
Pro Glu Thr Lys Asp Trp Arg Glu Asp Gly Ile Val Ser Pro Val Lys
145                 150                 155                 160
Asn Gln Ala His Cys Gly Ser Cys Trp Thr Phe Ser Thr Thr Gly Ala
                165                 170                 175
Leu Glu Ala Ala Tyr Thr Gln Ala Thr Gly Lys Asn Ile Ser Leu Ser
                180                 185                 190
Glu Gln Gln Leu Val Asp Cys Ala Gly Gly Phe Asn Asn Phe Gly Cys
            195                 200                 205
Asn Gly Gly Leu Pro Ser Gln Ala Phe Glu Tyr Gln Tyr Asn Gly Gly
        210                 215                 220
Ile Asp Thr Glu Glu Ser Tyr Pro Tyr Lys Gly Val Asn Gly Val Cys
225                 230                 235                 240
His Tyr Lys Ala Glu Asn Ala Ala Val Gln Val Leu Asp Ser Val Asn
                245                 250                 255
Ile Thr Leu Asn Ala Glu Asp Glu Leu Lys Asn Ala Val Gly Leu Val
                260                 265                 270
Arg Pro Val Ser Val Ala Phe Gln Val Ile Asp Gly Phe Arg Gln Tyr
            275                 280                 285
Lys Ser Gly Val Tyr Thr Ser Asp His Cys Gly Thr Thr Pro Asp Asp
        290                 295                 300
Val Asn His Ala Val Leu Ala Val Gly Tyr Gly Val Glu Asn Gly Val
305                 310                 315                 320
```

```
Pro Tyr Trp Leu Thr Lys Asn Ser Trp Gly Ala Asp Trp Gly Asp Asn
            325                 330                 335

Gly Tyr Phe Lys Met Glu Met Gly Lys Asn Met Cys Ala Ile Ala Thr
            340                 345                 350

Cys Ala Ser Tyr Pro Val Val Ala Ala
            355                 360

<210> SEQ ID NO 76
<211> LENGTH: 380
<212> TYPE: PRT
<213> ORGANISM: Actinidin

<400> SEQUENCE: 76

Met Gly Leu Pro Lys Ser Phe Val Ser Met Ser Leu Leu Phe Phe Ser
 1               5                  10                  15

Thr Leu Ile Leu Ser Leu Ala Phe Asn Ala Lys Asn Leu Thr Gln
            20                  25                  30

Arg Thr Asn Asp Glu Val Lys Ala Met Tyr Glu Ser Trp Leu Ile Lys
            35                  40                  45

Tyr Gly Lys Ser Tyr Asn Ser Leu Gly Glu Trp Glu Arg Arg Phe Glu
 50                  55                  60

Ile Phe Lys Glu Thr Leu Arg Phe Ile Asp Glu His Asn Ala Asp Thr
 65                  70                  75                  80

Asn Arg Ser Tyr Lys Val Gly Leu Asn Gln Phe Ala Asp Leu Thr Asp
            85                  90                  95

Glu Glu Phe Arg Ser Thr Tyr Leu Gly Phe Thr Ser Gly Ser Asn Lys
            100                 105                 110

Thr Lys Val Ser Asn Arg Tyr Glu Pro Arg Phe Gly Gln Val Leu Pro
            115                 120                 125

Ser Tyr Val Asp Trp Arg Ser Ala Gly Ala Val Val Asp Ile Lys Ser
 130                 135                 140

Gln Gly Glu Cys Gly Gly Cys Trp Ala Phe Ser Ala Ile Ala Thr Val
145                 150                 155                 160

Glu Gly Ile Asn Lys Ile Val Thr Gly Val Leu Ile Ser Leu Ser Glu
            165                 170                 175

Gln Glu Leu Ile Asp Cys Gly Arg Thr Gln Asn Thr Arg Gly Cys Asn
            180                 185                 190

Gly Gly Tyr Ile Thr Asp Gly Phe Gln Phe Ile Ile Asn Asn Gly Gly
            195                 200                 205

Ile Asn Thr Glu Glu Asn Tyr Pro Tyr Thr Ala Gln Asp Gly Glu Cys
 210                 215                 220

Asn Leu Asp Leu Gln Asn Glu Lys Tyr Val Thr Ile Asp Thr Tyr Glu
225                 230                 235                 240

Asn Val Pro Tyr Asn Asn Glu Trp Ala Leu Gln Thr Ala Val Thr Tyr
            245                 250                 255

Gln Pro Val Ser Val Ala Leu Asp Ala Ala Gly Asp Ala Phe Lys His
            260                 265                 270

Tyr Ser Ser Gly Ile Phe Thr Gly Pro Cys Gly Thr Ala Ile Asp His
            275                 280                 285

Ala Val Thr Ile Val Gly Tyr Gly Thr Glu Gly Ile Asp Tyr Trp
            290                 295                 300

Ile Val Lys Asn Ser Trp Asp Thr Thr Trp Gly Glu Glu Gly Tyr Met
305                 310                 315                 320

Arg Ile Leu Arg Asn Val Gly Gly Ala Gly Thr Cys Gly Ile Ala Thr
            325                 330                 335
```

Met Pro Ser Tyr Pro Val Lys Tyr Asn Asn Gln Asn His Pro Lys Pro
            340                 345                 350

Tyr Ser Ser Leu Ile Asn Pro Pro Ala Phe Ser Met Ser Lys Asp Gly
            355                 360                 365

Pro Val Gly Val Asp Asp Gly Gln Arg Tyr Ser Ala
            370                 375                 380

<210> SEQ ID NO 77
<211> LENGTH: 318
<212> TYPE: PRT
<213> ORGANISM: Homo sapien cathepsin C

<400> SEQUENCE: 77

Thr Met Thr Gly Trp Val His Asp Val Leu Gly Arg Asn Trp Ala Cys
 1               5                  10                  15

Phe Thr Gly Lys Lys Val Gly Thr Ala Ser Glu Asn Val Tyr Val Asn
            20                  25                  30

Thr Ala His Leu Lys Asn Ser Gln Glu Arg Leu Tyr Lys Tyr Asp His
            35                  40                  45

Asn Phe Val Lys Ala Ile Asn Ala Ile Gln Lys Ser Trp Thr Ala Thr
 50                  55                  60

Thr Tyr Met Glu Tyr Glu Thr Leu Thr Leu Gly Asp Met Ile Arg Arg
 65                  70                  75                  80

Ser Gly Gly His Ser Arg Lys Ile Pro Arg Pro Lys Pro Ala Pro Leu
                 85                  90                  95

Thr Ala Glu Ile Gln Gln Lys Ile Leu His Leu Pro Thr Ser Trp Asp
            100                 105                 110

Trp Arg Val Ser Pro Val Arg Asn Gln Ala Ser Cys Gly Ser Cys Tyr
            115                 120                 125

Ser Phe Ala Ser Met Gly Met Leu Glu Ala Arg Ile Arg Ile Leu Thr
130                 135                 140

Asn Asn Ser Gln Thr Pro Ile Leu Ser Pro Gln Glu Val Val Ser Cys
145                 150                 155                 160

Ser Gln Tyr Ala Gln Gly Cys Glu Gly Gly Phe Pro Tyr Leu Ile Ala
                165                 170                 175

Gly Lys Tyr Ala Gln Asp Phe Gly Leu Val Glu Glu Ala Cys Phe Pro
            180                 185                 190

Tyr Thr Gly Thr Asp Ser Pro Cys Lys Met Lys Glu Asp Cys Phe Arg
            195                 200                 205

Tyr Tyr Ser Ser Glu Tyr His Tyr Val Gly Phe Tyr Gly Gly Cys
            210                 215                 220

Asn Glu Ala Leu His Gly Pro Met Ala Val Ala Phe Glu Val Tyr Asp
225                 230                 235                 240

Asp Phe Leu His Tyr Lys Lys Gly Ile Tyr His His Thr Gly Leu Phe
                245                 250                 255

Asn Pro Phe Glu Leu Thr Asn His Ala Val Leu Leu Val Gly Tyr Gly
            260                 265                 270

Thr Gly Met Asp Tyr Trp Ile Val Lys Asn Ser Trp Gly Thr Gly Trp
            275                 280                 285

Gly Glu Asn Gly Tyr Phe Arg Ile Arg Arg Gly Thr Asp Glu Cys Ala
            290                 295                 300

Ile Glu Ser Ile Ala Val Ala Ala Thr Pro Ile Pro Lys Leu
305                 310                 315

<210> SEQ ID NO 78
<211> LENGTH: 286
<212> TYPE: PRT
<213> ORGANISM: Sarcophaga cathepsin B

<400> SEQUENCE: 78

```
Met Arg Gln His Phe Val Ile Ile Cys Ile Ala Phe Leu Ala Phe Gly
  1               5                  10                  15

Gln Val Leu Ala Asn Leu Asp Ala Glu Asn Asp Leu Leu Ser Asp Glu
             20                  25                  30

Phe Leu Glu Ile Val Arg Ser Lys Ala Lys Thr Trp Thr Pro Gly Arg
         35                  40                  45

Asn Tyr Asp Lys Ser Val Pro Arg Ser His Phe Arg Arg Leu Met Gly
     50                  55                  60

Val His Pro Asp Ala His Lys Phe Thr Leu His Glu Lys Ser Leu Val
 65                  70                  75                  80

Leu Gly Glu Glu Val Gly Leu Ala Asp Ser Asp Val Pro Glu Glu Phe
                 85                  90                  95

Asp Ala Arg Lys Ala Trp Pro Asn Cys Pro Thr Ile Gly Glu Ile Arg
            100                 105                 110

Asp Gln Gly Ser Cys Gly Ser Cys Trp Ala Phe Gly Ala Val Glu Ala
        115                 120                 125

Met Ser Asp Arg Leu Cys Ile His Ser Asn Ala Thr Ile His Phe His
    130                 135                 140

Phe Ser Ala Asp Asp Leu Val Ser Cys Cys His Thr Cys Gly Phe Gly
145                 150                 155                 160

Cys Asn Gly Gly Phe Pro Gly Ala Ala Trp Ala Tyr Trp Thr Arg Lys
                165                 170                 175

Gly Ile Val Ser Gly Gly Pro Tyr Gly Ser Ser Gln Gly Cys Arg Pro
            180                 185                 190

Tyr Glu Lys Glu Ile Met Gln Asn Gly Pro Val Glu Gly Ala Phe Thr
        195                 200                 205

Val Tyr Glu Asp Leu Ile Leu Tyr Lys Asp Gly Val Tyr Gln His Val
    210                 215                 220

His Gly Arg Glu Leu Gly Gly His Ala Ile Arg Ile Leu Gly Trp Gly
225                 230                 235                 240

Val Glu Asn Lys Thr Pro Tyr Trp Leu Ile Ala Asn Ser Trp Asn Thr
                245                 250                 255

Asp Trp Gly Asn Asn Gly Phe Phe Lys Met Leu Arg Gly Glu Asp His
            260                 265                 270

Cys Gly Ile Glu Ser Ala Ile Ala Ala Gly Leu Pro Lys Val
        275                 280                 285
```

<210> SEQ ID NO 79
<211> LENGTH: 282
<212> TYPE: PRT
<213> ORGANISM: Homo sapien cathepsin B

<400> SEQUENCE: 79

```
Met Trp Gln Leu Trp Ala Ser Leu Cys Cys Leu Leu Val Leu Ala Asn
  1               5                  10                  15

Ala Arg Ser Arg Pro Ser Phe His Pro Val Ser Asp Glu Leu Val Asn
             20                  25                  30

Tyr Val Asn Lys Arg Asn Thr Thr Trp Gln Ala Gly His Asn Phe Tyr
         35                  40                  45

Asn Val Asp Met Ser Tyr Leu Lys Arg Leu Cys Gly Thr Phe Leu Gly
```

```
                50                      55                      60
Gly Pro Lys Pro Pro Gln Arg Val Met Phe Thr Glu Asp Leu Lys Leu
 65                  70                      75                  80

Pro Ala Ser Phe Asp Ala Arg Glu Gln Trp Pro Gln Cys Pro Thr Ile
                 85                      90                  95

Lys Glu Ile Arg Asp Gln Gly Ser Cys Gly Ser Cys Trp Ala Phe Gly
                100                     105                 110

Ala Val Glu Ala Ile Ser Asp Arg Ile Cys Ile His Thr Asn Ala His
            115                     120                 125

Val Ser Val Glu Val Ser Ala Glu Asp Leu Leu Thr Cys Cys Gly Ser
        130                     135                 140

Met Cys Gly Asp Gly Cys Asn Gly Gly Tyr Pro Ala Glu Ala Trp Asn
145                     150                     155                 160

Phe Trp Thr Arg Lys Gly Leu Val Ser Gly Leu Tyr Glu Ser His
                165                     170                 175

Val Gly Cys Arg Pro Tyr Ser Ala Glu Ile Tyr Lys Asn Gly Pro Val
                180                     185                 190

Glu Gly Ala Phe Ser Val Tyr Ser Asp Phe Leu Leu Tyr Lys Ser Gly
            195                     200                 205

Val Tyr Gln His Val Thr Gly Glu Met Met Gly His Ala Ile Arg
        210                     215                 220

Ile Leu Gly Trp Gly Val Glu Asn Gly Thr Pro Tyr Trp Leu Val Ala
225                     230                     235                 240

Asn Ser Trp Asn Thr Asp Trp Gly Asp Asn Gly Phe Phe Lys Ile Leu
                245                     250                 255

Arg Gly Gln Asp His Cys Gly Ile Glu Ser Glu Val Val Ala Gly Ile
                260                     265                 270

Pro Arg Thr Asp Gln Tyr Trp Glu Lys Ile
            275                     280

<210> SEQ ID NO 80
<211> LENGTH: 339
<212> TYPE: PRT
<213> ORGANISM: Sarcophaga cathepsin L

<400> SEQUENCE: 80

Met Arg Thr Val Leu Val Ala Leu Leu Ala Leu Val Ala Leu Thr Gln
 1               5                      10                  15

Ala Ile Ser Pro Leu Asp Leu Ile Lys Glu Glu Trp His Thr Tyr Lys
                20                      25                  30

Leu Gln His Arg Lys Asn Tyr Ala Asn Glu Val Glu Glu Arg Phe Arg
            35                      40                  45

Met Lys Ile Phe Asn Glu Asn Arg His Lys Ile Ala Lys His Asn Gln
 50                      55                      60

Leu Phe Ala Gln Gly Lys Val Ser Tyr Lys Leu Gly Leu Asn Lys Tyr
 65                  70                      75                  80

Ala Asp Met Leu His His Glu Phe Lys Glu Thr Met Asn Gly Tyr Asn
                 85                      90                  95

His Thr Leu Arg Gln Leu Met Arg Glu Arg Thr Gly Leu Val Gly Ala
                100                     105                 110

Thr Tyr Ile Pro Pro Ala His Val Thr Val Pro Lys Ser Val Asp Trp
            115                     120                 125

Arg Glu His Gly Ala Val Thr Gly Val Lys Asp Gln Gly His Cys Gly
        130                     135                 140
```

```
Ser Cys Trp Ala Phe Ser Ser Thr Gly Ala Leu Glu Gly Gln His Phe
145                 150                 155                 160

Arg Lys Ala Gly Val Leu Val Ser Leu Ser Glu Gln Asn Leu Val Asp
            165                 170                 175

Cys Ser Thr Lys Tyr Gly Asn Asn Gly Cys Asn Gly Gly Leu Met Asp
            180                 185                 190

Asn Ala Phe Arg Tyr Ile Lys Asp Asn Gly Gly Ile Asp Thr Glu Lys
        195                 200                 205

Ser Tyr Pro Tyr Glu Gly Ile Asp Asp Ser Cys His Phe Asn Lys Ala
        210                 215                 220

Thr Ile Gly Ala Thr Asp Thr Gly Phe Val Asp Ile Pro Glu Gly Asp
225                 230                 235                 240

Glu Glu Lys Met Lys Lys Ala Val Ala Thr Met Gly Pro Val Ser Val
            245                 250                 255

Ala Ile Asp Ala Ser His Glu Ser Phe Gln Leu Tyr Ser Glu Gly Val
            260                 265                 270

Tyr Asn Glu Pro Glu Cys Asp Glu Gln Asn Leu Asp His Gly Val Leu
        275                 280                 285

Val Val Gly Tyr Gly Thr Asp Glu Ser Gly Met Asp Tyr Trp Leu Val
        290                 295                 300

Lys Asn Ser Trp Gly Thr Thr Trp Gly Glu Gln Gly Tyr Ile Lys Met
305                 310                 315                 320

Ala Arg Asn Gln Asn Asn Gln Cys Gly Ile Ala Thr Ala Ser Ser Tyr
            325                 330                 335

Pro Thr Val

<210> SEQ ID NO 81
<211> LENGTH: 14
<212> TYPE: PRT
<213> ORGANISM: Sarcophaga peregrina

<400> SEQUENCE: 81

His Cys Gly Ile Glu Ser Ala Ile Ala Ala Gly Leu Pro Lys
 1               5                  10

<210> SEQ ID NO 82
<211> LENGTH: 14
<212> TYPE: PRT
<213> ORGANISM: murine

<400> SEQUENCE: 82

His Cys Gly Ile Glu Ser Glu Ile Val Ala Gly Ile Pro Arg
 1               5                  10

<210> SEQ ID NO 83
<211> LENGTH: 14
<212> TYPE: PRT
<213> ORGANISM: rattus

<400> SEQUENCE: 83

His Cys Gly Ile Glu Ser Glu Ile Val Ala Gly Ile Pro Arg
 1               5                  10

<210> SEQ ID NO 84
<211> LENGTH: 14
<212> TYPE: PRT
<213> ORGANISM: bovine

<400> SEQUENCE: 84
```

```
His Cys Gly Ile Glu Ser Glu Ile Val Ala Gly Met Pro Cys
  1               5                  10
```

<210> SEQ ID NO 85
<211> LENGTH: 14
<212> TYPE: PRT
<213> ORGANISM: Homo sapien

<400> SEQUENCE: 85

```
His Cys Gly Ile Glu Ser Glu Val Val Ala Gly Ile Pro Arg
  1               5                  10
```

<210> SEQ ID NO 86
<211> LENGTH: 14
<212> TYPE: PRT
<213> ORGANISM: chicken

<400> SEQUENCE: 86

```
His Cys Gly Ile Glu Ser Glu Ile Val Ala Gly Val Pro Arg
  1               5                  10
```

<210> SEQ ID NO 87
<211> LENGTH: 14
<212> TYPE: PRT
<213> ORGANISM: Nicotiana

<400> SEQUENCE: 87

```
Glu Cys Glu Ile Glu Asp Glu Val Val Ala Gly Leu Pro Ser
  1               5                  10
```

<210> SEQ ID NO 88
<211> LENGTH: 1916
<212> TYPE: DNA
<213> ORGANISM: Sarcophaga peregrina

<400> SEQUENCE: 88

| | | | | |
|---|---|---|---|---|
| aaacactaca | ttattattca | ttcattttga | acaaaaagaa | gagaattatt ttatcatcat | 60 |
| tttgcaaagt | cattaaaagt | aacaaagaag | actgcgagga | gtgaaagtgc atcagggata | 120 |
| aggaagaaaa | tgcgttgcac | attgattttt | gcaattattg | ctggcattgc aattacagct | 180 |
| ttggccacaa | atccaccacg | ctgggatccc | aactatatag | ttaagggcac attatatatt | 240 |
| ccctatgcgg | aaatagctga | accattttat | gcctggtacg | ataagaatac acgacgttcc | 300 |
| cgtattgatt | actatggtgg | catggtgaaa | acctatcaat | ggcaaatga acatccttt | 360 |
| ggtacttctt | taaaattggc | ccccattacc | actaaatcag | agttaaacaa agtaacatgt | 420 |
| cttcaactga | atggcacttc | tgaagatccc | gtacaagtgc | aagcaatatt gccaaatgcc | 480 |
| aaggacttca | aacttatagg | cactgaaacc | tttttaggct | tcaactgtga caattccgc | 540 |
| ttagaggaaa | caattggcga | taagaaaaat | gtatacactt | tgtgggtacg ttataagaag | 600 |
| tcaccccatt | atccggcttc | aagaatgccc | ataccagtac | gctatgaaat gagaggttac | 660 |
| aatacccttt | tgggttccca | ttatgatcac | tattatctgg | attatgatag ttacgatcac | 720 |
| gatgatatac | ccaatgaagt | atttgaattg | gatgataaca | tggaatgtat gcctttccct | 780 |
| ggacccggca | aaggtcatta | tgccaccttc | aatcccatgc | aagagtttgt tcatcccact | 840 |
| gtagaccatc | atgtggagca | tgcctttaaa | catttcaaaa | acaagcatgg cattgattat | 900 |
| cgcaccgaac | aagagcatga | aatcgtaaa | acatctttta | gacaaaatct gagatttatt | 960 |
| aattcgaaaa | atcgtggcaa | attaagttat | actcttgcca | ttaaccactt ggcagataaa | 1020 |
| agcgatgatg | aactaaaggg | tcgtcgaggt | tataaatcat | cggtgtctt taatacaggc | 1080 |

```
aaaccattcc cttacaattt ggaaaagtac cgtgacacag tgccagatca atatgattgg      1140
cgtttgtatg gtgccgtaac acccgttaaa gatcaatctg tttgcggttc ttgttggtct      1200
tttggcacta ttgccatttt ggagggtgca tttttcctta agaatggcgg caatttggta      1260
cgcttatcgc aacaagcttt aatcgattgc tcttgggagt atggcaacaa cggttgtgat      1320
ggtggcgaag atttccgtgc ctataaatgg atgatgaaa tgggcggtgt acccacagaa       1380
gaagaatatg gtccctattt aggtcaagat ggttattgtc atgccaaaaa tgttagtctg      1440
gtggcaccca ttactggctt cttttaatgtt acacctaatg atcctatggc tttaaaaatt    1500 gccctttta aacatggccc catatcggtt gctattgatg cctcacccaa aacctttagt       1560
ttctattcgc acggtgtcta ctatgaacct acctgcaaga atggtcttga tgaacttgat     1620
catgctgtct tggccgtggg ctatggcaca atcaacggcg aagattactg gctggtaaag     1680
aattcttggt ctacttattg gggcaatgat ggttatattt taatgtctgc ccgtaaaaat     1740
aattgcggtg ttatgaccat gcccacttat gtagagatgt aagcatattg atggtctgct     1800
taaagcttta taaaatgact ttaatttca tttaattttt cttaattttt tttttttata      1860
agttgatcta ctaaaataag aaagaaaata aaaattgttt aaataaaaaa aaaaaa        1916
```

<210> SEQ ID NO 89
<211> LENGTH: 1738
<212> TYPE: DNA
<213> ORGANISM: Drosophila melanogaster
<220> FEATURE:
<223> OTHER INFORMATION: "n" bases represent undetermined nucleotides

<400> SEQUENCE: 89

```
gaanaaactg ttntttcgaa aagataggta ntatagtnga gtcgggatca gttcatattc      60
cagacaattc tctggtgaat tctcaagaat gcaagtgttt ttagctttag ccctgctcgc     120
aggcttggct ttctcagcta atgccacgaa tccgcggaaa tgggatccaa actacatagt     180
caaaggaacc ctgtacattc cgtacgccga gattgcggaa cccttctacg cctggtatga    240
caagaatacg aggcgatccc gcatcgatta ctacggcgga atggtgaaga cataccaact    300
ggctggcgag ggtcagtacg gaaccctgct gaagctggca ccgattacca ccaagacgga    360
gaacaacaag ctaacctgtc tgcaggtgaa tggcaccgcc gaccaggctg tcgatattca    420
gagcatcctg cccgatgcga aacctttcag cctggtgggc accgaatcct ttttgggcta    480
cacgtgcgac aagttccgcc tggagtcgac aattggccaa agaaaaaaca tctatacgct    540
gttggtnnnn nnnnnnnnnn nnnnnnnnnn nnnnnnnnnn nnnnnnnnnn nnnnnnnnnn    600
nnnnnnnnnn nnnnnnnnnn nnnnnnnnnn nnnnnnnnnn nnnnnnnnnn nnnnttgga     660 ctatgacagc tacgagcacg atgatattcc caacgaggtg ttcgagatcg atgacagcct    720
gcagtgcgtc ggattccccg gacccggcac cggtcactat gccaccttca tcccatgca    780 ggagttcata tccggaaccg atgagcatgt ggacaaggcc ttccaccact tcaagcgcaa    840
gcacggagtt gcttatcaca gcgacacgga acacgagcat cgcaagaaca tcttccgtca   900
gaacctgcgc tacatccact ccaagaaccg ggccgaactc acttacactt tggccgttaa    960
tcacttggcc gacaagaccg aagaggagtt gaaggcacga gcggatacaa atcatcggg    1020 catctacaac accggcaaac cgttccccta tgatgtgccc aagtacaagg acgagattcc   1080
cgaccagtac gactggcggc tgtacggcgc tgtcactccg gtgaaagatc aatctgtgtg   1140
cggatcgtgc tggtcatttg gcaccattgg tcacctggag ggcgccttct tcctgaagaa   1200
```

```
tggcggcaat ctggtccggc tttcccagca ggcgttgatt gactgctcgt gggcctatgg   1260
caacaatggc tgcgatggtg gcgaggattt ccgcgtgtac cagtggatgc tgcagtccgg   1320
cggagtgccc acgaggagg  agtacggtcc ctatctgggc caggatggct actgtcacgt   1380
gaacaacgtg acgctggtgg cacccattaa gggattcgtc aatgtgacct ccaacgatcc   1440
gaatgccttc aagctggctt tgctcaagca cggtcctctg tcggtggcca ttgatgcttc   1500
tcccaagaca tttagcttct actcgcacgg agtttactat gagccaacct gcaagaacga   1560
tgtaaatgga ctggatcatg ctgtcttggc cgtgggcggg ggctcagtca atggacaaga   1620
ctattggctg gtaaaaaacc ccnggtccac ctactggggc aacgatggct acatcctgat   1680
gttcgggcaa aaaacaatt  gcggtgttat gaccatgccc acttatgtgg anatgtaa    1738
```

<210> SEQ ID NO 90
<211> LENGTH: 1750
<212> TYPE: DNA
<213> ORGANISM: Periplaneta americana
<220> FEATURE:
<223> OTHER INFORMATION: "n" bases represent undetermined nucleotides

<400> SEQUENCE: 90

```
gtttgtgggg tgcacagtnn acttacaggg aaagggccaa tttntgtatc ggtactttg     60 ctgttcctga tttcgagaac ttcagctgaa gcattacatg gcttggaatc ttttattttc    120
ggcggtgttg ccatcgctt  ttgtgtctgt gctgggtgca gatccaacac caccgaactt    180
cagtgatact tatacagtaa agggaacact ttacattcca tatgcagaga ttcgtgagcc    240
tttcttagcg tattacgact tgactgttgg gtctagccgc attgattact atggaggaat    300
ggtgaaaacg tatcaaatca gcaagtatgg aaatttcgga acaagtttaa aggttgcacc    360
tgtgacaaca gagaaagtag agaataagga aacttgccta caagtcaacg gaaccaaaga    420
caacaaaatc gaaccacaga gtattcttcc agacttaaca ggattcaagt tgattggtac    480
agaaccaata aatggcctga attgcgaaaa atggcgtttg gtggacacaa aaggagccaa    540
ggtcaacaaa tacacaatgt ggattcggta caagaatctg caaatgatcc tggtgttaaa    600
aatcgccatc ccagttcgat acgaaatgaa gggttacnac tctttgctgg gttctcatta    660
tgaccactac tacctggagt acgattgttg ctttcagaaa cctgatccag tgttttccaa    720
gttgaaagca attgacatgc accagcttcc cagtccagga gacagacata tttacacatt    780
taaccctatg aaggagttca ttcataatta tgacgaacat gtagaaaccg catttgatca    840
cttccgaaaa agacacagca aggantacgc cagcaatttg gaacacacaa agagaaaaga    900
aattttccga cagaatttga ggttcatcca ttctaagaat cgtgctagat taggattcac    960
tctggacgtg aaccatttgg tggaccggac agagctcgaa ctgaaagctc tgaggggaa    1020 gcaatacact gacgggtaca atggaggttc tccatttcct tataccaatc ttgacgcaat   1080
catggaccaa attcctgatg atttggactg gagaatttat ggtgctgtga ctccagttaa   1140
agatcagtct gtttgcggct cttgttggag ttttgggact actggcacca tcgaaggagc   1200
ttatttcttg aagtatggac atttggtgcg attgtcacna caggctctaa ttgactgcag   1260
ctggggctat ggtaacaatg gttgtgatgg aggtgaagat ttccgctctt atgaatggat   1320
gatgaagcat ggtggcatcc cactggaaga cgaatatgga ggctatttgg gccaggatgg   1380
ctattgtcat gtcgaaaatg taactctcac agcaaagatc actggctatg tgaacgtcac   1440
atctggagac attgatgnnn nnnnnnnnnn nnnnnnnnnn nnnnnnnnn  nnnnnnnnn    1500 nnnnnnnnnn nnnnnnnnnn nnnnnnnnnn nnnnnnnnnn nnnnnnnnnn nnnnnnnnnn   1560
```

```
nnnnnnnnnn nnnnnnnnnn nnnnnnnnnn nnnnnnnnnn nnnnnnnnnn nnnnnnnnnn    1620
nnnnnnnnnn nnnnnnnnnn nnnnnnnnnn nnnnnnnnnn nnnnnnnnnn nnnnnnnnnn    1680
nnnnnnnnnn nnnnnnnnnn nnnnnnnnnn nnnnnnnnnn nnnnnnnnnn nnnnnnnnnn    1740 nnnnnnnnnn                                                            1750
```

<210> SEQ ID NO 91
<211> LENGTH: 67
<212> TYPE: PRT
<213> ORGANISM: Sarcophaga peregrina

<400> SEQUENCE: 91

```
Pro Asn Tyr Ile Val Lys Gly Thr Leu Tyr Ile Pro Tyr Ala Glu Ile
  1               5                  10                  15

Ala Glu Pro Phe Tyr Ala Trp Tyr Asp Lys Asn Thr Arg Arg Ser Arg
                 20                  25                  30

Ile Asp Tyr Tyr Gly Gly Met Val Lys Thr Tyr Gln Leu Ala Asn Glu
             35                  40                  45

His Pro Phe Gly Thr Ser Leu Lys Leu Ala Pro Ile Thr Thr Lys Ser
         50                  55                  60

Glu Leu Asn
 65
```

<210> SEQ ID NO 92
<211> LENGTH: 67
<212> TYPE: PRT
<213> ORGANISM: Drosophila melanogaster

<400> SEQUENCE: 92

```
Pro Asn Tyr Ile Val Lys Gly Thr Leu Tyr Ile Pro Tyr Ala Glu Ile
  1               5                  10                  15

Ala Glu Pro Phe Tyr Ala Trp Tyr Asp Lys Asn Thr Arg Arg Ser Arg
                 20                  25                  30

Ile Asp Tyr Tyr Gly Gly Met Val Lys Thr Tyr Gln Leu Ala Gly Glu
             35                  40                  45

Gly Gln Tyr Gly Thr Leu Leu Lys Leu Ala Pro Ile Thr Thr Lys Thr
         50                  55                  60

Glu Asn Asn
 65
```

<210> SEQ ID NO 93
<211> LENGTH: 67
<212> TYPE: PRT
<213> ORGANISM: Periplaneta americana

<400> SEQUENCE: 93

```
Asp Thr Tyr Thr Val Lys Gly Thr Leu Tyr Ile Pro Tyr Ala Glu Ile
  1               5                  10                  15

Arg Glu Pro Phe Leu Ala Tyr Tyr Asp Leu Thr Val Gly Ser Ser Arg
                 20                  25                  30

Ile Asp Tyr Tyr Gly Gly Met Val Lys Thr Tyr Gln Ile Ser Lys Tyr
             35                  40                  45

Gly Asn Phe Gly Thr Ser Leu Lys Val Ala Pro Val Thr Thr Glu Lys
         50                  55                  60

Val Glu Asn
 65
```

```
<210> SEQ ID NO 94
<211> LENGTH: 67
<212> TYPE: PRT
<213> ORGANISM: Homo sapien

<400> SEQUENCE: 94

Gly Asn Glu Phe Trp Ser Ala Leu Leu Glu Lys Ala Tyr Ala Lys Val
 1               5                  10                  15

Asn Gly Ser Tyr Glu Ala Leu Ser Gly Ser Thr Ser Glu Gly Phe
            20                  25                  30

Glu Asp Phe Thr Gly Gly Val Thr Glu Trp Tyr Glu Leu Arg Lys Ala
        35                  40                  45

Pro Ser Asp Leu Tyr Gln Ile Ile Leu Lys Ala Leu Glu Arg Gly Ser
    50                  55                  60

Leu Leu Gly
 65

<210> SEQ ID NO 95
<211> LENGTH: 67
<212> TYPE: PRT
<213> ORGANISM: rattus

<400> SEQUENCE: 95

Arg Asn Glu Phe Trp Ser Ala Leu Leu Glu Lys Ala Tyr Ala Lys Leu
 1               5                  10                  15

His Gly Ser Tyr Glu Ala Leu Lys Gly Gly Asn Thr Thr Glu Ala Met
            20                  25                  30

Glu Asp Phe Thr Gly Gly Val Thr Glu Phe Phe Glu Ile Lys Asp Ala
        35                  40                  45

Pro Ser Asp Met Tyr Lys Ile Met Arg Lys Ala Ile Glu Arg Gly Ser
    50                  55                  60

Leu Met Gly
 65

<210> SEQ ID NO 96
<211> LENGTH: 67
<212> TYPE: PRT
<213> ORGANISM: chicken

<400> SEQUENCE: 96

Cys Thr Glu Phe Trp Ser Ala Leu Leu Glu Lys Ala Tyr Ala Lys Leu
 1               5                  10                  15

Asn Gly Cys Tyr Glu Ser Leu Ser Gly Gly Ser Thr Thr Glu Gly Phe
            20                  25                  30

Glu Asp Phe Thr Gly Gly Val Ala Glu Met Tyr Asp Leu Lys Arg Ala
        35                  40                  45

Pro Arg Asn Met Gly His Ile Ile Arg Lys Ala Leu Glu Arg Gly Ser
    50                  55                  60

Leu Leu Gly
 65

<210> SEQ ID NO 97
<211> LENGTH: 67
<212> TYPE: PRT
<213> ORGANISM: Drosophila melanogaster

<400> SEQUENCE: 97

Lys Asn Glu Phe Trp Ser Ala Leu Leu Glu Lys Ala Tyr Ala Lys Leu
 1               5                  10                  15
```

```
His Gly Ser Tyr Glu Ala Leu Lys Gly Gly Ser Thr Cys Glu Ala Met
            20                  25                  30

Glu Asp Phe Thr Gly Gly Val Ser Glu Trp Tyr Asp Leu Lys Glu Ala
            35                  40                  45

Pro Gly Asn Leu Phe Thr Ile Leu Gln Lys Ala Ala Glu Arg Asn Ser
            50                  55                  60

Met Met Gly
 65

<210> SEQ ID NO 98
<211> LENGTH: 67
<212> TYPE: PRT
<213> ORGANISM: nematode

<400> SEQUENCE: 98

Asn Asn Glu Phe Trp Ser Ala Leu Leu Glu Lys Ala Tyr Ala Lys Leu
 1               5                  10                  15

Phe Gly Ser Tyr Glu Ala Leu Lys Gly Gly Thr Thr Ser Glu Ala Leu
            20                  25                  30

Glu Asp Met Thr Gly Gly Leu Thr Glu Phe Ile Asp Leu Lys Asn Pro
            35                  40                  45

Pro Arg Asn Leu Met Gln Met Met Met Arg Gly Phe Glu Met Gly Ser
            50                  55                  60

Leu Phe Gly
 65

<210> SEQ ID NO 99
<211> LENGTH: 67
<212> TYPE: PRT
<213> ORGANISM: fluke

<400> SEQUENCE: 99

Pro Thr Glu Phe Trp Ser Ala Leu Leu Glu Lys Ala Tyr Ala Lys Leu
 1               5                  10                  15

Asn Gly Cys Tyr Ala His Leu Ser Gly Gly Ser Gln Ser Glu Ala Met
            20                  25                  30

Glu Asp Leu Thr Gly Gly Ile Cys Leu Ser Leu Glu Leu Asn Gln Lys
            35                  40                  45

Glu Arg Pro Ser Asp Leu Ile Asp Gln Leu Lys Ile Tyr Ala Gln Arg
            50                  55                  60

Cys Cys Leu
 65

<210> SEQ ID NO 100
<211> LENGTH: 4
<212> TYPE: PRT
<213> ORGANISM: Unknown
<220> FEATURE:
<223> OTHER INFORMATION: Description of Unknown Organism: substrate

<400> SEQUENCE: 100

Leu Leu Val Tyr
 1

<210> SEQ ID NO 101
<211> LENGTH: 4
<212> TYPE: PRT
<213> ORGANISM: Unknown
<220> FEATURE:
<223> OTHER INFORMATION: Description of Unknown Organism: substrate
```

```
<400> SEQUENCE: 101

Ala Ala Pro Phe
```

PROTEASE

This is a Division of Application Ser. No. 09/120,365 filed Jul. 22, 1998. The entire disclosure of the prior application(s) is hereby incorporated by reference herein in its entirety.

BACKGROUND OF THE INVENTION

1. Field of the Invention

This invention relates to an enzyme having a new cysteine protease-like activity. The enzyme of this invention is a bimolecular protease comprising two subunits, that is, one subunit having a molecular weight of about 26 kDa and the other having a molecular weight of about 29 kDa.

2. Prior Art

Proteases are mainly classified into four categories including serine proteases, cysteine proteases, aspartic acid proteases and metalloproteases according to their structure and catalytic activity. Among them, the proteases which include the most numerous members and have been studied most intensively from old times are serine proteases and cysteine proteases. The serine protease includes the majority of digestive proteases and serum proteases, and attention has been paid to their extracellular functions thereof. In contrast, the cysteine protease has been believed to be an important group of enzymes in the intracellular digestion of proteins (Katsunuma, N., "Intracellular digestion of proteins (in Japanese)," pp. 35–50, Tokyo Kagaku-Dojin Publishing Co.).

As representative examples of the cysteine protease, the cathepsin type proteases such as cathepsin L and cathepsin B may be mentioned, and these enzymes have been assumed to be lysosomal proteases. The lysosomal protease is a protease which digests, in the cell, proteins carried into lysosomes or one of intracellular organellae, and is believed, on the basis of its basic role in biological functions, to exist universally in organisms.

Cathepsin L and cathepsin B were also demonstrated in a flesh fly (Sarcophaga peregrina) which undergoes a complete metamorphosis (Kurata, S., et al. (1982) Eur. J. Biochem., 204, 911–914; Takahashi, N., et al. (1933) FBBS. Lett. 334, 153–157; Homma, K., et al. (1994) J. Biol. Chem., 269, 15258–15264). Cathepsin L and cathepsin B demonstrated in the fly, so it was found, not only act as a lysosome enzyme but also function as a secretory enzyme involved in morphogenesis in the manner as described below. Namely, cathepsin B of flesh fly, while the fly is developing from a third-instar larva into an adult, is discharged from body fluid cells and digests unneeded larval tissues and fat bodies discharged from the body fluid (Kurata, S., et al. (1989) J. Insect Physiol. 35, 559–565; Kurata S., et al. (1990) Insect Biochem. 20, 461–465; Kurata, S., et al. (1992) Dev. Biol., 153, 115–121).

Further, cathepsin L of flesh fly is discharged from an imaginal disk when stimulated with ecdysone, and digests the basal membrane of the imaginal disk to help the imaginal disk to develop into the matured structure of the imaginal disk (Homma, K., et al. (1994) J. Biol. Chem. 269, 15258–15264).

As described above, it was discovered that cathepsin L and cathepsin B, which had been originally assumed to be a lysosome enzyme, has a novel property hitherto unknown, that is, they function also extracellularly in certain aspects of insect life.

From the flesh fly, another secretory cysteine protease, that is, 26·29 kDa protease was newly discovered. This 26·29 kDa protease is a protease isolated from the body fluid cells of a flesh fly and purified, and as its activity is inhibited by E64 or a specific inhibitor of cysteine proteases, it has been assumed that the protease in question is one of cysteine proteases. However, in contrast with known cysteine proteases, the protease in question has following new properties.

(1) It has a unique structure, that is, it comprises two subunits having molecular weights of 26 kDa and 29 kDa, respectively.

(2) The protease, so it was demonstrated, is discharged from body fluid cells into the body fluid when sheep red cells are injected as a foreign substance into the body of a third-instar larva of the flesh fly. From this fact, it has been assumed that this protease serves for the body protection of the larva.

Regarding cysteine proteases, various molecular variants have been reported heretofore, but the majority of them have a property of a monomolecularity, and the 26·29 kDa protease was thought possibly a new protease hitherto unknown, because it is a bimolecular type protease. The 26·29 kDa protease never fails to exist as a bimolecule type whenever it was found to have an enzymatic activity, and thus it was assumed that this substance may be a protease advanced in evolution one step ahead of fellow proteases which, comprising two subunits to act in a concerted manner, may execute a new function inaccessible to monomolecular fellow proteases.

Furthermore, there have been no known cysteine proteases that are secreted in response to a nocuous stimulus such as injection of a foreign substance like the one as described in (2) above, and in this respect too, it was assumed that the 26·29 kDa protease is a new cysteine protease.

SUMMARY OF THE INVENTION

This invention relates to a new protease, or the 26·29 kDa protease.

Namely, this invention relates to proteins having amino acid sequences as represented by the attached Sequence Listing, SEQ. ID. NOS. 1, 3 and 5, and having a cysteine protease-like activity.

Further, this invention relates to a DNA sequence having a base sequence as represented by the attached Sequence Listing, SEQ. ID. NOS. 2, 4 or 6.

Furthermore, this invention relates to an enzyme comprising a protein having an amino acid sequence as represented by the attached Sequence Listing, SEQ. ID. NOS. 1, 3 or 5, and having a cysteine protease-like activity.

BRIEF DESCRIPTION OF THE DRAWINGS

FIG. 2 shows the amino acid sequences of partial peptides derived from 26 kDa subunit. The alphabets following the numeral "26" represent thus derived different partial peptides.

FIG. 3 shows the amino acid sequences of partial peptides derived from 29 kDa subunit. The alphabets following the numeral "29" represent thus derived different partial peptides.

FIG. 4 shows the manner how primers to be used for PCR amplification of a fragment which codes for 26 kDa subunit were designed.

FIG. 5 shows the base sequence of c DNA which codes for the precursor of 26·29 kDa protease of Sarcophaga. In each lower row, corresponding amino acids are represented by one-letter codes. The underlined parts in the figure represent sequences corresponding to peptides derived from 26 kDa and 29 kDa subunits.

FIG. 6 shows designing primers to be applied for sequencing c DNA which codes for the precursor of 26·29 kDa protease of Sarcophaga.

FIG. 7 shows the positions of primers in the c DNA which codes for the precursor of 26·29 kDa protease of Sarcophaga SEQ ID NO 1 and 2.

FIG. 8, being a continuation of FIG. 7, shows the positions of primers in the c DNA which codes for the precursor of 26·29 kDa protease of Sarcophaga SEQ ID NO 1 and 2.

FIG. 9 shows a comparison of the amino acid sequence of the precursor of 26·29 kDa protease with those of various known cysteine protease precursors.

Figure 10:
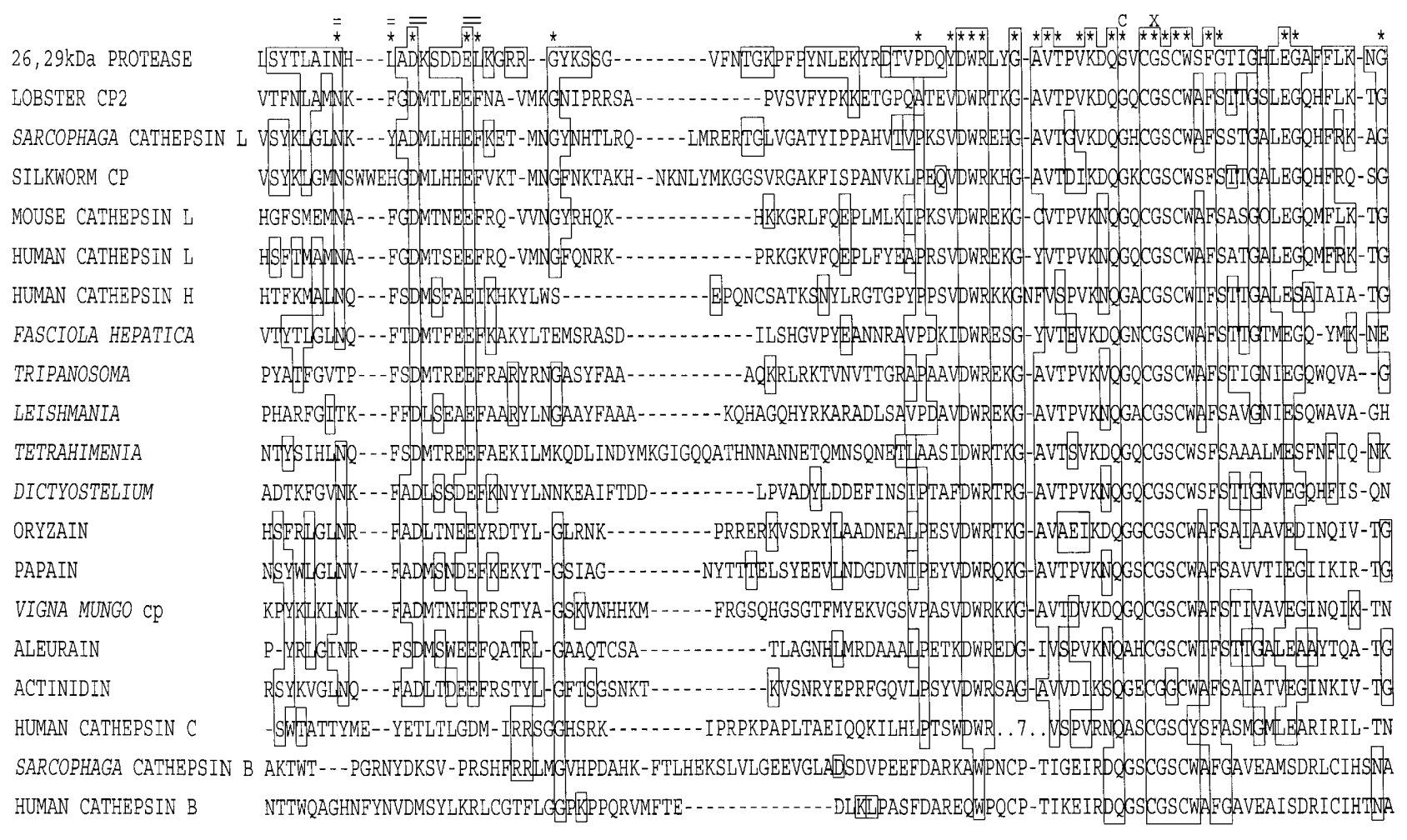

FIG. 10 is a continuation of the amino acid sequences given in FIG. 9.

Figure 11:
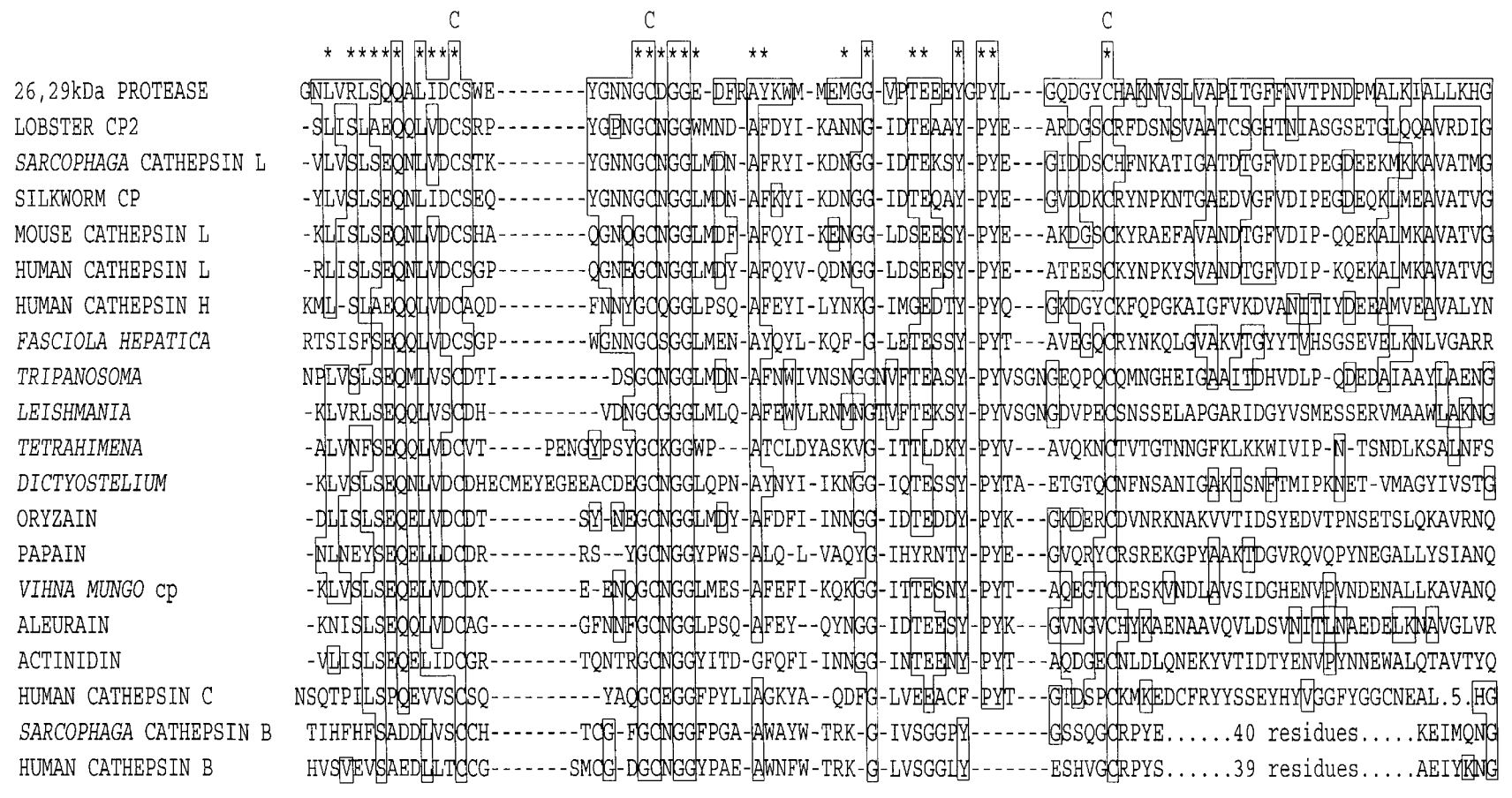

FIG. 11 is a further continuation of the amino acid sequences given in FIG. 10.

FIG. 13 shows a comparison of the amino acid sequence of the precursor of 26·29 kDa protease with that from the cathepsin L precursor of Sarcophaga.

FIG. 17 shows how glutamic acid is conserved in various cathepsin Ls.

Figure 1:
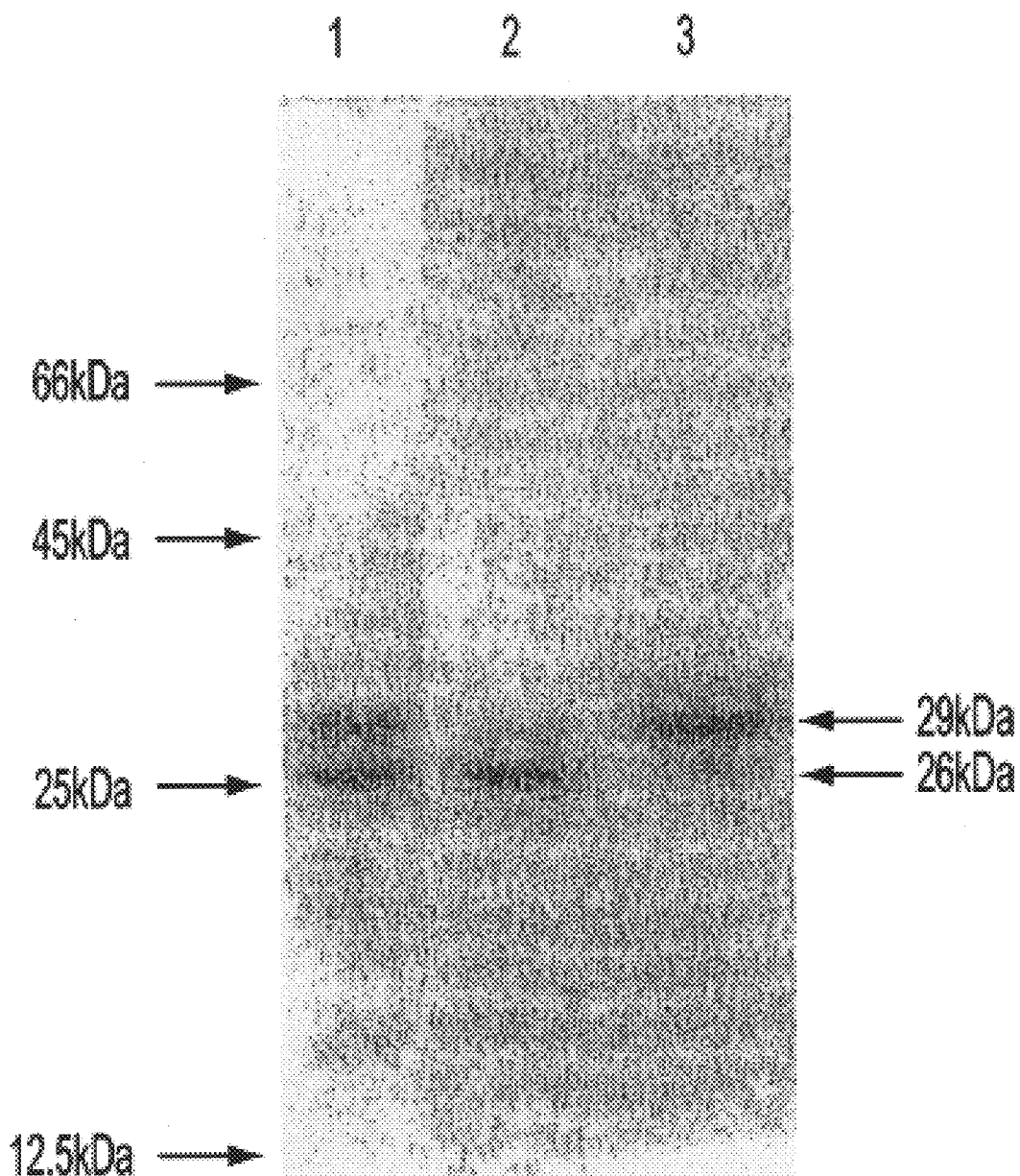
FIG. 1 is a drawing of electrophoretic patterns derived from the purified 26 kDa and 29 kDa subunits.
Figure 12:
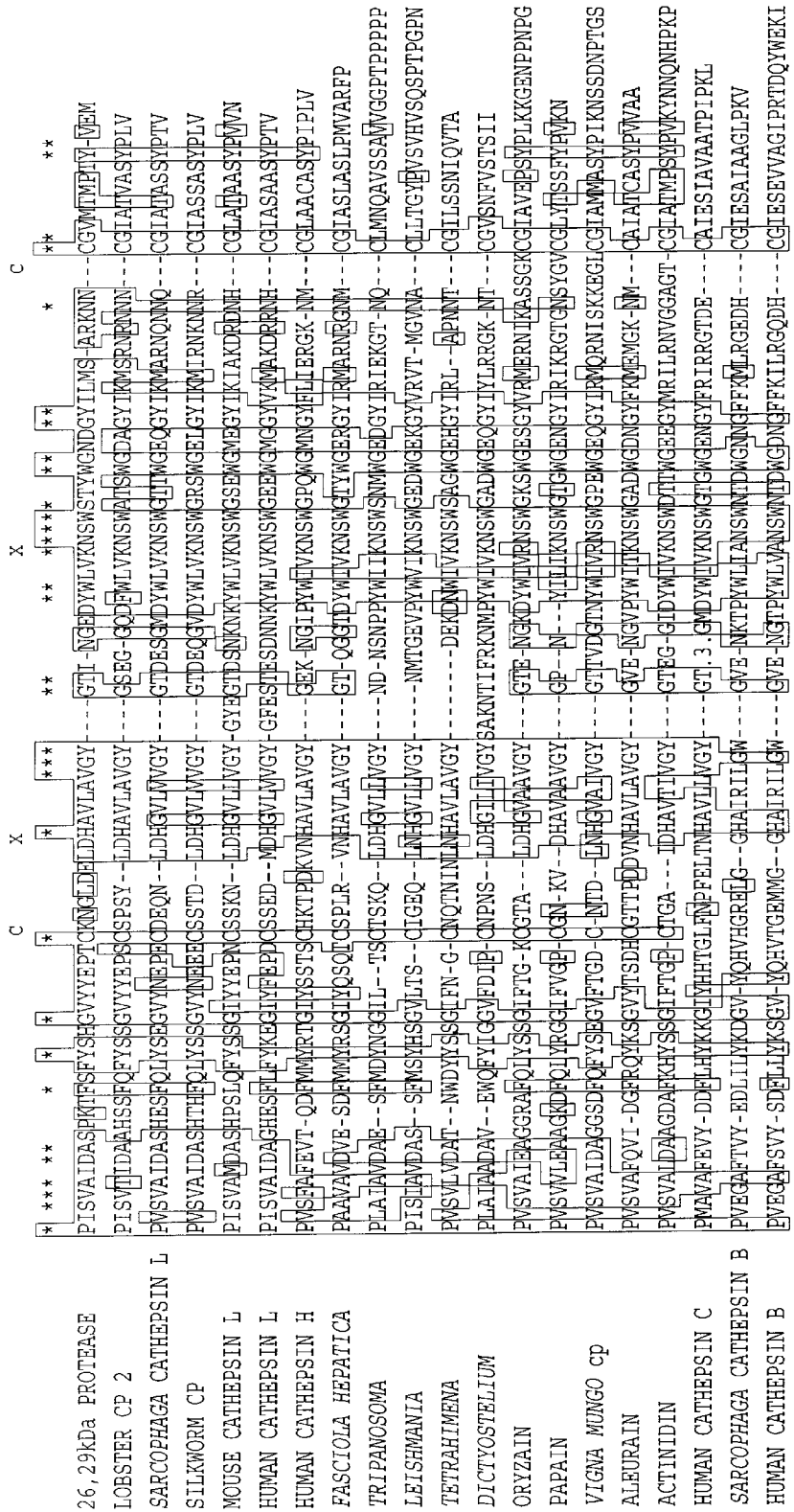
FIG. 12 is a still further continuation of the amino acid sequences given in FIG. 11.

Lane 1 is derived from an unfertilized egg, lane 2 from a fertilized egg of 5 day incubation, lane 3 from an egg of 7 day incubation, lane 4 from an egg of 9 day incubation, lane 5 from a larva of first stage, lane 6 from a larva of second stage, lane 7 from a larva of third stage, lane 8 from a pupa of 1 day metamorphosis, lane 9 from a pupa of 3 day metamorphosis, lane 10 from a larva of 5 day metamorphosis, and lane 11 from an adult. The bands at 18S and 28S show ribosome RNA markers.

Figure 20:
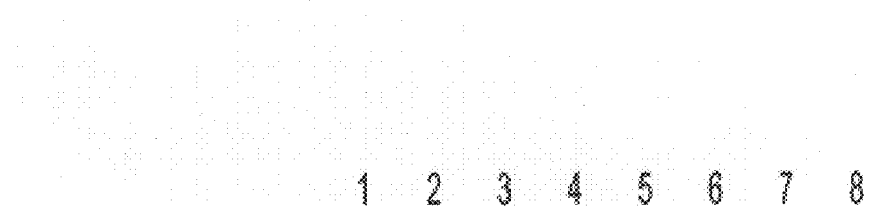

FIG. 20 is a drawing showing the immunoblotting of antibodies against 26 kDa subunit reacted in an unfertilized egg and fertilized egg.

Lane 1 is derived from an unfertilized egg, lane 2 from a fertilized egg of 5 day incubation, lane 3 from an egg of 6 day incubation, lane 4 from an egg of 7 day incubation, lane 5 from an egg of 8 day incubation, lane 6 from an egg of 9 day incubation, lane 7 from an egg of 10 day incubation, and lane 8 from an egg of 11 day incubation.

FIG. 21 shows the base sequences of c DNAs coding for the precursors of 26·29 kDa proteases derived from various insects.

FIG. 22 is a continuation of FIG. 21.

FIG. 23 is a further continuation of FIG. 22.

FIG. 24 is a photographic plate showing the amino acid sequences of the precursors of 26·29 kDa proteases derived from various insects.

FIG. 25 is a drawing showing a comparison of a part of 26 kDa subunit of 26·29 kDa protease with the well-conserved, corresponding parts of various calpain sequences.

Figure 26:
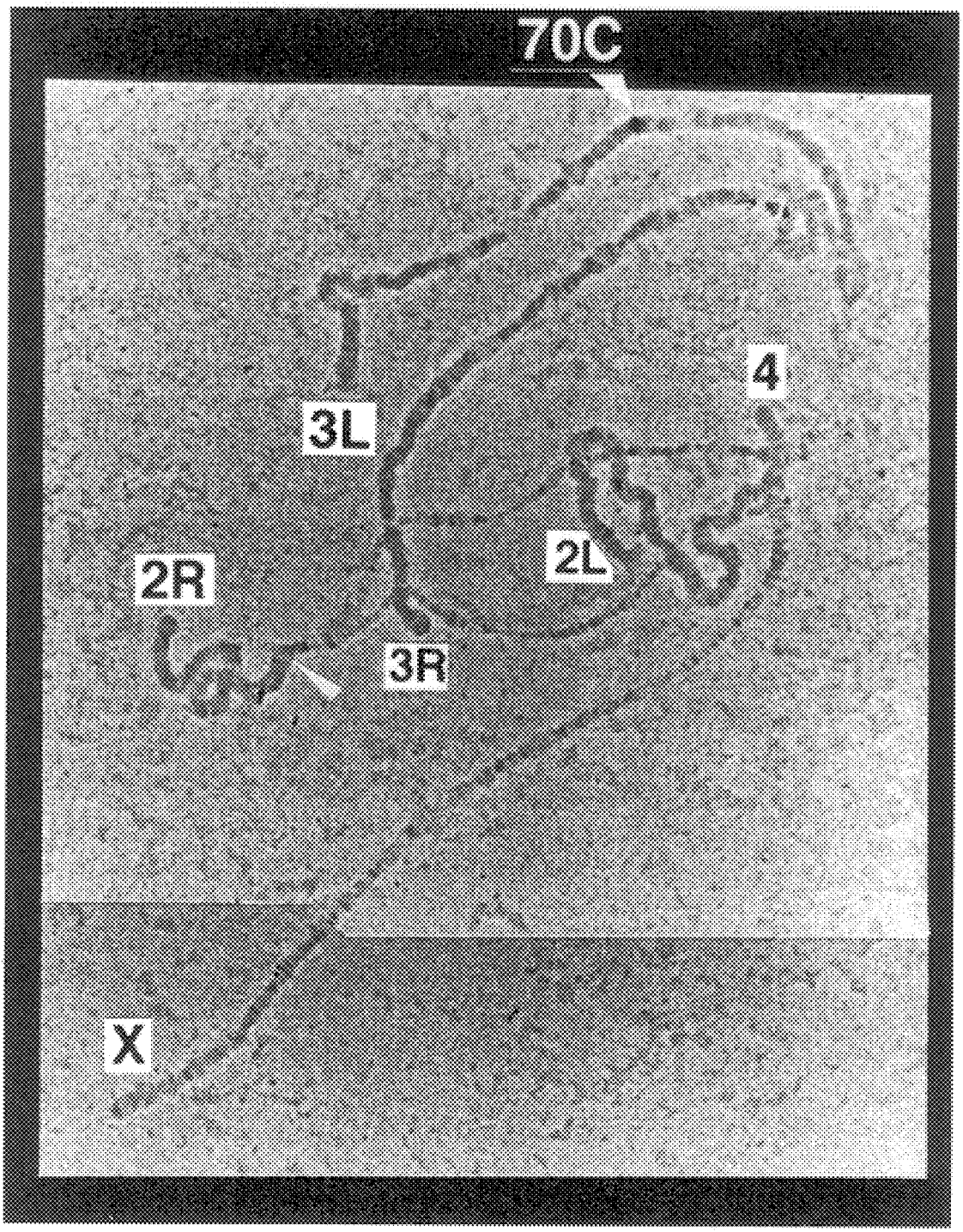

FIG. 26 is a photographic plate, which was taken to check the gene locus of 26·29 kDa protease in a salivary gland chromosome of Drosophila which had been stained for this purpose. From this observation it was found that the gene locus of 26·29 kDa protease is at 70C locus of L arm of the third salivary gland chromosome.

DESCRIPTION OF THE PREFERRED EMBODIMENTS

The structure of the new protease of this invention will be firstly described.

The 26·29 kDa protease, in contrast with other many cysteine proteases, is a bimolecular type protease. The analysis based on peptide mapping suggested that the two subunits are different from each other in their primary structure. To substantiate the suggestion, a trial to determine the partial amino acid sequences of these two subunits was launched.

Firstly, those subunits were separated so that the amino acid sequences of the two subunits might be determined independently of each other. The purified 26·29 kDa protease was submitted to 12.5% SDS-polyacrylamide gel electrophoresis and to CBB staining, and then the two subunits were removed from the gel. The thus removed gel blocks were transferred into a dialysis bag through which an electric current was flowed under the same condition as in the electrophoresis, to electrically elute the proteins of interest. The eluate, after undergoing ethanol precipitation, produced respective subunit proteins, which were then removed of SDS and dissolved anew in 50 mM Tris/HCl (pH 8.5) to produce samples which served for the determination of partial amino acid sequences of the proteins in question.

The purity of thus obtained 26 kDa and 29 kDa subunits was assayed by SDS-PAGE, and the results are shown in FIG. 1.

Next, to the sample solution was added lysyl-end-peptidase or arginyl-end-peptidase and the yield was incubated at 30° C. overnight for digestion. The thus digested solution was applied to reversed phase HPLC (C18 column) to isolate peptides. The thus isolated and purified partial peptides were applied to an automatic peptide sequencer to determine their amino acid sequences.

The thus determined amino acid sequences are shown in FIGS. 2 and 3.

Chart 1, Sequence listing numbers for sequences in FIG. 2.

| | |
|---|---|
| 26KNterm | SEQ. ID NO. 11 |
| 26KE | SEQ. ID NO. 12 |
| 26KD | SEQ. ID NO. 13 |
| 26KR3 | SEQ. ID NO. 14 |
| 26K1 | SEQ. ID NO. 15 |
| 26KA | SEQ. ID NO. 16 |
| 26KB | SEQ. ID NO. 17 |
| 26KC | SEQ. ID NO. 18 |
| 26KG | SEQ. ID NO. 19 |
| 26KR7 | SEQ. ID NO. 20 |
| 26K2 | SEQ. ID NO. 21 |

-continued

| | |
|---|---|
| 26KH | SEQ. ID NO. 22 |
| 26KF | SEQ. ID NO. 23 |
| 26KR2 | SEQ. ID NO. 24 |
| 26K3 | SEQ. ID NO. 25 |
| 26KI | SEQ. ID NO. 26 |
| 26KJ | SEQ. ID NO. 27 |
| 26KR5 | SEQ. ID NO. 28 |

Chart 2, Sequence listing numbers for sequences in FIG. 3.

| | |
|---|---|
| 29KNterm | SEQ. ID NO. 29 |
| 29KD | SEQ. ID NO. 30 |
| 29KB1 | SEQ. ID NO. 31 |
| 29KB2 | SEQ. ID NO. 32 |
| 29KE1 | SEQ. ID NO. 33 |
| 29KE2 | SEQ. ID NO. 34 |
| 29KF | SEQ. ID NO. 35 |
| 29KJ | SEQ. ID NO. 36 |

Further, it was found that the peptides resulting from the digestion by lysyl-end-peptidase have some sequences identical with the peptides resulting from the digestion byarginyl-end-peptidase, and the relative positions of individual component peptides were partly determined on the basis of this finding. It was found as a result of homology search that the sequence of amino acids derived from 29 kDa subunit is quite similar to that of a certain protease or a member of cathepsin L family, while 26 kDa subunit does not show any significant homology to known proteins, suggesting that it is a novel protein. From this finding, it was concluded that the structure of 26·29 kDa protease results from combining a protease subunit having a cathepsin L-like structure with a subunit having a hitherto unknown structure different from any known proteases Next, cloning of c DNAs coding for these subunits were performed as follows. ps (1) Amplification of the c DNA Fragments Coding for 26 kDa Subunit by PCR Firstly, for acquisition of probes for screening, a c DNA fragment coding for 26 kDa subunit was amplified by PCR.

As it had been found through immunoblotting analysis that the adult primodium contained in a third-instar larva of flesh fly already contains 26·29 kDa protease, a DNA fragment (prepared by T. Kunieda) extracted from a c DNA library prepared from the adult primodium of a third-instar larva of flesh fly was used as the template for amplification. The primer used consists of a sense primer designed from an amino acid sequence at N-terminal of 26 kDa subunit and an antisense primer designed from an amino acid sequence located at a position other than N-terminal, and they were used in unison (see FIG. 4).

Chart 3, Sequence listing numbers for sequences in FIG. 4.

| | |
|---|---|
| 26K1 | SEQ. ID NO. 37 |
| 26K5'-1 | SEQ. ID NO. 38 |
| 26K5'-3 | SEQ. ID NO. 39 |
| 26K5'-2 | SEQ. ID NO. 40 |
| 26K3'-N | SEQ. ID NO. 41 |
| 26K3 | SEQ. ID NO. 42 |
| 26K3'-2 | SEQ. ID NO. 43 |
| 26K3'-1 | SEQ. ID NO. 44 |
| 26K1 | SEQ. ID NO. 45 |
| 26K3'-I | SEQ. ID NO. 46 |

The yields obtained by PCR were submitted to 2% agarose electrophoresis for analysis. Firstly, 26K5'-1 and 26K3'-1 primers, and 26K5'-1 and 26K3'-1 primers were combined respectively for PCR, but the yields did not appear as a single band. Then, primers are prepared anew such that they locate more medially in terms of amino acid sequence than the primers initially used for PCR, and PCR was performed for a second time. Combinations of 26K5'-2 and 26K3'-1 primers, of 26K5'-2 and 26K3'-2 primers, and of 26K5'-2 and 26K3'-N primers were used, and from each combination a single band was amplyfied.

These yields were introduced into a PCRII vector, and the vector was allowed to infect E. coli and then cloned (TA cloning). Screening consisted of choosing insert-positive cells through blue/white selection, and of submitting DNA from the chosen cells to PCR using the cell body of E. coli as the template. As a result it was confirmed that the sequence of insert DNA contains two sequences coding respectively for 26 kD peptide and 26 KH peptide shown in FIG. 2 jointed in series, and that the yield derived from PCR is a part of c DNA coding for 26 kDa subunit.

(2) Cloning of c DNA Coding for 26 kDa Subunit by Colony Hybridization

The thus obtained c DNA fragment coding for 26 kDa subunit was labeled with 32P by the random primer labeling method, and used as a probe for screening.

This probe was applied to a c DNA library prepared from the adult primodium of a third stage larva of flesh fly which had been transformed into an E. coli type by in vivo excision, and screening was performed by colony hybridization. It was found, however, that there was no clone that gave duplicate positive results.

(3) Cloning by PCR of c DNA Coding for 26 kDa Subunit

Then, the previous screening was modified such that PCR using an E. coli type c DNA library as the template was introduced. The library used included a c DNA library prepared from the primodium of a third stage larva of flesh fly which had been transformed into an E. coli type in step (2). Screening was performed by the limiting dilution method described below. Screening by the limiting dilution method E. coli cells containing the c DNA library in plasmids were allowed to multiply to the full growth; 10× serially diluted solutions were prepared therefrom; and each diluted solution was used as the template for PCR. PCR was performed two times such that an inward crossing might result.

For the first PCR 26K5'-1 and 26K3'-1 primers were used while for the second PCR 26K5'-2 and 26K3'-1 primers were used. As a result it was found that, although PCR gave a positive result as long as the test solution was diluted ten thousand times or less, the solution diluted hundred thousand times or more gave no positive result.

Next, condensation of c DNA coding for 26·29 kDa protease was performed as described below. The aforementioned ten thousand times diluted cell solution was cultivated to the full growth, and the yield was diluted a hundred thousand times. The diluted sample was inoculated into 33 tubes, and for each tube it was checked whether or not it contained any positive PCR yields. As a result it was found that seven tubes gave positive PCR yields. From this it can be said that choosing any one from the seven tubes is equivalent to condensation of the original c DNA coding for 26·29 kDa protease or a target protein as much as about 4.7 fold (33/7=4.7). Similarly, for a second condensation, the thus chosen cell solution was cultivated to the full growth, diluted three million times, and inoculated into 288 wells of a microtiter plate. Out of these wells, two wells gave positive PCR yields. Through this procedure, the cell population in question was condensed 144 times (288/2=144). A 0.001 μl aliquot was sampled from one of them, and plated on agar medium. The resulting colonies were checked for the existence of PCR yields. As a result, PCR yields were detected in one colony out of 23 colonies studied. This clone was thought to be a clone containing the c DNA for 26·29 kDa protease here concerned.

The length of insert contained in this clone was estimated to be approximately 1900 bp, a value considerably larger than the shortest necessary length for coding for 26 kDa protein or about 700 bp.

The base sequence of insert was determined (see FIG. 5 and Sequence Listing, SEQ ID NO. 2). The sequence was determined sequentially from 5' end. During the process in which the sequence was read out one by one from 5' end, segments coding for the peptides constituting 26 kDa subunit were discovered one after another (the underlined sequences in FIG. 5 SEQ ID NO 1 and SEQ ID NO 2). From this it was concluded that this clone certainly comprises cells with the gene for 26 kDa subunit. As reading progressed, however, it was found that segments coding for peptides constituting 29 kDa subunit then appeared one after another until all the components thereof were obtained (the underlined sequences in FIG. 5).

Chart 4, Sequence listing numbers for sequences in FIG. 6.

| seq SA | SEQ. ID NO. 47 |
| seq SB | SEQ. ID NO. 48 |
| seq SC | SEQ. ID NO. 49 |
| seq SD | SEQ. ID NO. 50 |
| seq SE | SEQ. ID NO. 51 |
| seq SF | SEQ. ID NO. 52 |
| seq AA | SEQ. ID NO. 53 |
| seq AB | SEQ. ID NO. 54 |
| seq AC | SEQ. ID NO. 55 |
| seq AD | SEQ. ID NO. 56 |
| seq AE | SEQ. ID NO. 57 |
| seq AF | SEQ. ID NO. 58 |
| seq AG | SEQ. ID NO. 59 |

From this it was found that this clone contains the gene coding for both of 26 kDa and 29 kDa subunits.

The two subunits were encoded by the sequences contained in one open reading frame (ORF) with no frame shifts occurring in the middle. Within this ORF, a stop codon exists at 28 bp position from 5' end of c DNA, then at 130 bp position a first methionine codon appears, and finally at 1780 bp position a second stop codon appears. The ORF is perfect in its form. This ORF is the longest of all ORFs contained in the c DNA and there was no other ORFs with such a long sequence. Further, this longest ORF was followed by signals studded with poly (A) appearing at 1887 bp and 1902 bp positions, and the latter signal studded with poly (A) was then followed by a true poly (A) sequence.

From these findings, it was concluded that the c DNA isolated in this trial consists of a perfect sequence free from any flaws as long as the untranslated region of 5' end is excluded from consideration, and that the above-described ORF region will be actually translated into a corresponding protein. If this ORF were employed for study, the protein it encodes would have a length of 550 amino acids because it has a total length of 1650 bp. This protein would contain both of the sequences coding respectively for 26 kDa and 29 kDa subunits and thus the two subunits would be produced initially as one cluster, or one precursor.

Figure 16:
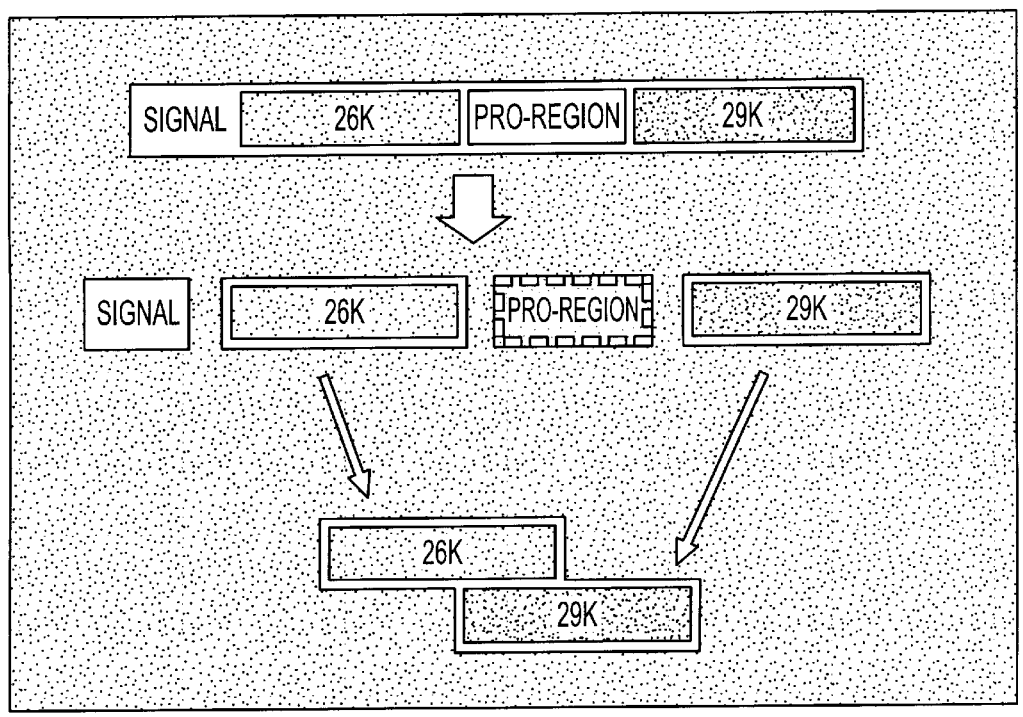
FIG. 16 is a schematic diagram to show how the precursor of 26·29 kDa protease is processed.

The precursor protein of 26·29 kDa protease has a composition as represented at the top row in FIG. 16, and consists of four domains. They are, from N terminal in order, a secretion signal (the left end domain in FIG. 16), 26 kDa subunit (the second domain in FIG. 16), a pro-sequence observed in the precursor of cathepsin L-like protease (the third domain from left in FIG. 16), and 29 kDa subunit (the right end domain in FIG. 16).

Next, the structural features of individual domains constituting 26·29 kDa protease precursor will be described.

(i) About secretion signal

Firstly, the translation start methionine (N terminal) of this precursor protein is positioned by 19 amino acids closer to N terminal of c DNA insert than N terminal of 26 kDa subunit (see FIG. 5). These 19 amino acid residues were judged to be a secretion signal because they have following three features: they are located closest to N terminal of c DNA insert of all the translation products, they are rich in hydrophobic activity, and they are absent in 26 kDa subunit constituting a purified 26·29 kDa protease. Thus, the precursor protein of 26·29 kDa protease, like the precursors of many other cysteine proteases, has the structure characteristic with a secretory type protein.

(ii) About 26 kDa subunit

The 26 kDa subunit was found to have a novel structure because homology search did not show the existence of any known proteins having a significantly large homology.

(iii) About 29 kDa subunit

The 29 kDa subunit was found, as a result of homology search, to be similar, in its structure, to various adult type proteases belonging to cathepsin L family (see FIGS. 9–12 and Table 1).

Figure 9:
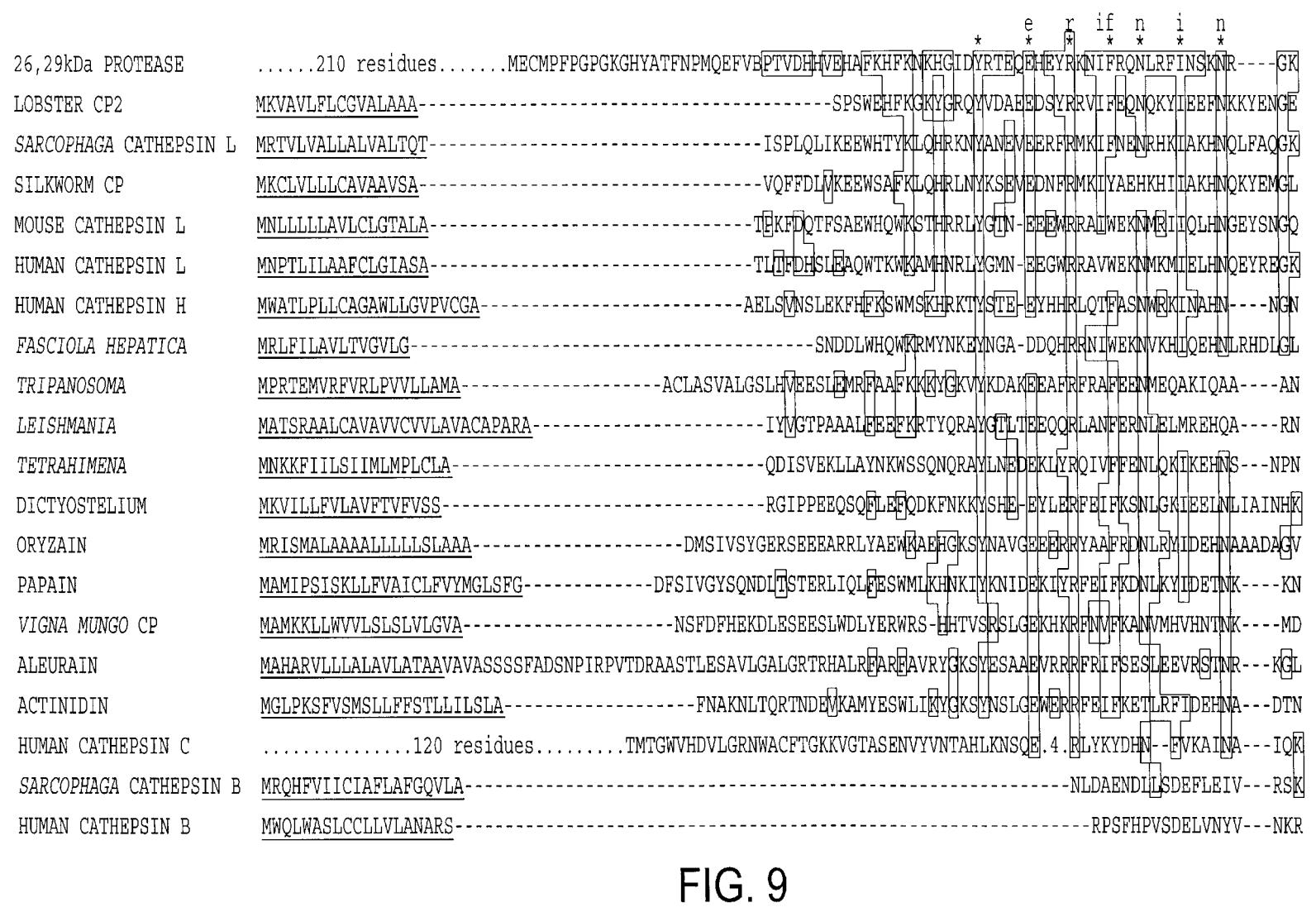

Chart 5, Sequence listing numbers for sequences in FIG. 9.

| 26, 29 kDa protease | SEQ. ID NO. 60 |
| lobster CP2 | SEQ. ID NO. 61 |
| Sarcophaga cathepsin L | SEQ. ID NO. 62 |
| silkworm CP | SEQ. ID NO. 63 |
| mouse cathepsin L | SEQ. ID NO. 64 |
| human cathepsin L | SEQ. ID NO. 65 |
| human cathepsin H | SEQ. ID NO. 66 |
| *Fasciola hepatica* | SEQ. ID NO. 67 |
| Tripanosoma | SEQ. ID NO. 68 |
| Leishmania | SEQ. ID NO. 69 |
| Tetrahimena | SEQ. ID NO. 70 |
| Dictyostelium | SEQ. ID NO. 71 |
| oryzain | SEQ. ID NO. 72 |
| Papain | SEQ. ID NO. 73 |
| *Vigna mungo* CP | SEQ. ID NO. 74 |
| Aleurain | SEQ. ID NO. 75 |
| Actinidin | SEQ. ID NO. 76 |
| human cathepsin C | SEQ. ID NO. 77 |
| Sarcophaga cathepsin B | SEQ. ID NO. 78 |
| Human cathepsin B | SEQ. ID NO. 79 |

It particularly most closely resembles an adult type enzyme or cathepsin L of flesh fly: 52% of amino acids was identical between the two (see FIG. 13 and (SEQ ID NO 80) Table 1). By contrast, only 20% of the amino acids it contains corresponds in sequence with those from another adult type enzyme or cathepsin B of flesh fly (see FIGS. 9 to 12 and Table 1) or it is less similar in sequence to proteases of cathepsin B family than to proteases of cathepsin L family.

TABLE 1

| Proteases | Number of identical amino acids | Identity |
|---|---|---|
| Sarcophaga cathepsin L | 116 | 52.5% |
| lobster CP2 | 111 | 50.2% |
| mouse cathepsin L | 108 | 48.9% |

TABLE 1-continued

| Proteases | Number of identical amino acids | Identity |
|---|---|---|
| human cathepsin L | 97 | 43.9% |
| human cathepsin H | 84 | 38.0% |
| rice oryzain | 82 | 37.1% |
| papaya papain | 81 | 36.7% |
| human cathepsin C | 67 | 30.3% |
| Sarcophaga cathepsin B | 48 | 21.7% |

Table 1 shows a comparison of the amino acid sequence of 29 kDa subunit derived from 26·29 kDa protease with the corresponding amino acid sequences of various cysteine proteases, and represents the numbers of identical amino acids and the identities (%) calculated based on the following equation.

Identity (%)=(number of identical amino acids)/(total number of amino acids contained in 29 kDa subunit or 221 amino acids)× 100

The conserved amino acid sequence includes three amino acids comprising cysteine, histidine and asparagine or the elements which have been thought to act as an active site of cysteine protease (amino acids marked by interrupted lines in FIG. 13 SEQ ID NO 1 and SEQ ID NO 80), and six cysteines which have been thought to form disulfide bonds in cathepsin L or the like (see FIGS. 9 to 12). Further, the process site (cut site) at N terminal of 29 kDa subunit has a sequence well correspondent with the sequences of other cathepsin L type proteases (see FIGS. 9 to 12). As seen from above, because 29 kDa subunit shares many basic properties possessed by cathepsin L-like proteases, it was presumed to be equivalent to a maturation type member of cathepsin L-like proteases.

(iv) About pro-sequence-like sequence

The majority of cysteine proteases belonging to cathepsin L family are initially produced as precursor proteins, and these precursor proteins are then processed to yield maturation type enzymes. The precursor protein exists as a maturation type enzyme conjugated at its N terminal with a peptide called a pro-sequence, and during processing this pro-sequence is cut off and removed. For a human cathepsin L to express a protease activity, it is necessary, so it has been suggested, to be initially produced as a precursor (Smith, S. M., et al. (1989) J. Biol. Chem. 264, 20487–20495). The precursor protein of 26·29 kDa protease was found to contain also a corresponding sequence which became obvious by comparison thereof with pro-sequences from other cathepsin L-like protease precursors (FIGS. 9–12, and FIG. 13). A region consisting of about 80 residues (colored amino acid sequences underlined by a thick solid line in FIG. 13, upper rows) adjacent to and upstream of N terminal of 29 kDa subunit may represent such a pro-sequence, and they have 25% amino acids in common with those contained in the pro-sequence region of a flesh fly cathepsin L precursor (amino acids framed by thick lines in FIG. 13). This region consisting of about 80 residues contains ERFININ motif (motif introduced and defined by Karrer, K. M., et al. (1993) Proc. Natl. Acad. Sci. U.S.A. 90, 3063–3077) and Ishidoh, et al. (Ishidoh, K., et al. (1987) FEBS LETT. 226, 33–37) (see FIGS. 9 to 12). From this it was concluded that the sequence in question was truly a pro-sequence of a cysteine protease. From this it was found that the precursor protein of 26·29 kDa protease contains a cysteine protease like cathepsin L in the form of a precursor, and that 26·29 kDa protease, like other known cathepsin L-like proteases, will undergo a process whereby the pro-sequence region is removed, to become an adult type enzyme.

(v) About C terminal of 26 kDa subunit

The boundary between this pro-sequence-like region and 26 kDa subunit, or C terminal of 26 kDa subunit is not necessarily clear. Assumed that C terminal of 26 kDa subunit corresponds with C terminal of the pro-sequence-like region, and C terminal of 26 kDa subunit connects directly with N-terminal of 29 kDa subunit, 26 kDa subunit will have a molecular weight of 36.3 kDa by calculation, and thus differ by as much as 10 kDa from the result obtained from SDS-PAGE. Thus it was concluded that C terminal of 26 kDa does not correspond with C terminal of pro-sequence region or is located at a position upstream (toward N terminal) of the latter. For determination of C terminal of 26 kDa subunit, two methods were used: one consists of determining the sequence from C terminal using a C terminal sequencer and the other of isolating the peptide of C terminal and of determining its sequence by Edman's method. But the two methods did not bring clear results. However, use of mass analysis (MALDI-MS) revealed that the molecular weight of 26 kDa subunit is about 24.3 kDa, supporting the result obtained by SDS-PAGE. If 24.3–26 kDa is used as a molecular weight of 26 kDa subunit, its C terminal will be positioned at 220–240th amino acid residue counted from the translation start methionine. As this position forms a boundary behind which (towards C terminal) the sequence shows a notable homology with the pro-sequence, and ahead which (towards N terminal) the sequence does not show any homology with the pro-sequence (FIG. 13), the position in question forms a boundary between the two domains in terms of their primary structures. Thus, the present inventor assume C terminal of 26 kDa subunit to be present close to that position.

(vi) About site to which a sugar-chain is linked

Each of 26 kDa and 29 kDa subunits has an asparagine at one site which may serve as a linking site for an N type sugar chain (FIG. 13). While 29 kDa subunit may be stained by CBB staining following SDS-PAGE, 26 kDa subunit can be detected as a clear, sharp band, and thus the latter may have no or little sugar chains linked thereto. The majority of cathepsin L-like cysteine proteases are secretory proteins, and contain asparagines which may allow N type sugar chains to link thereto, and the same may also hold true for 26·29 kDa protease.

(vii) About hydropathy profile

Figure 14:
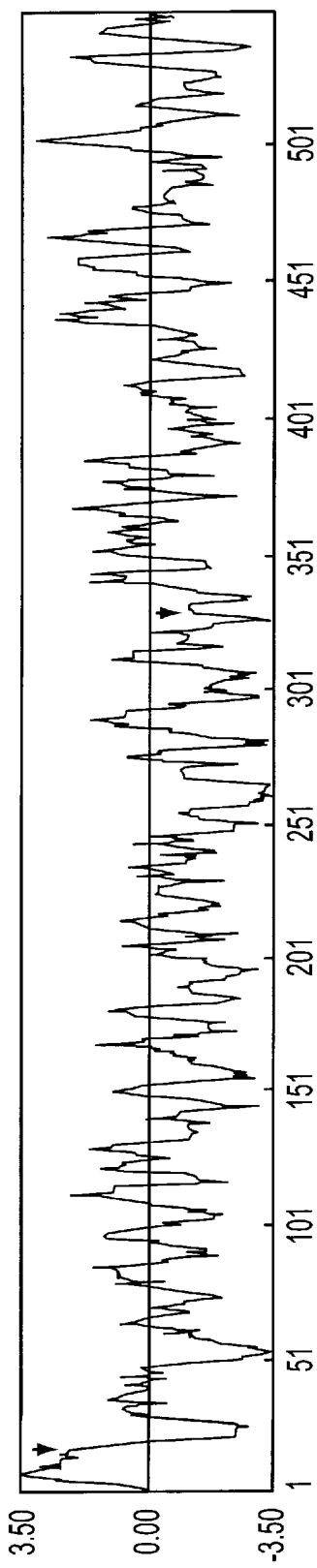
FIG. 14 shows the hydropathy profile of the precursor of 26·29 kDa protease of Sarcophaga.
Figure 15:
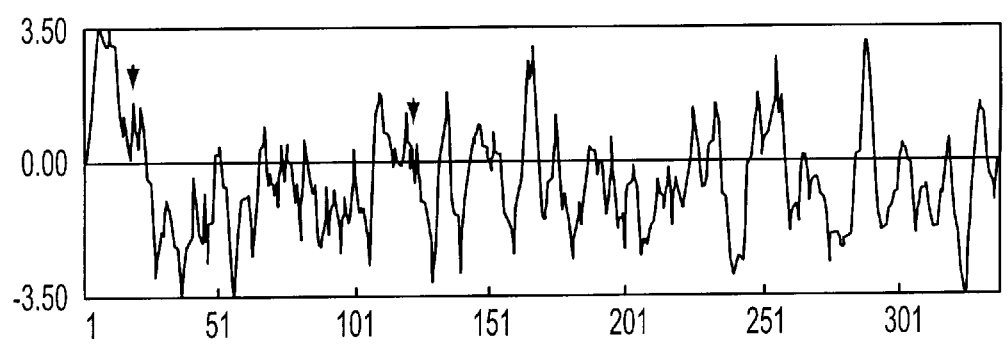
FIG. 15 shows the hydropathy profile of cathepsin L of Sarcophaga.

Hydropathy profile of 26·29 kDa protease precursor was examined, and the result indicated as shown in FIG. 14 that there is no region rich in hydrophobic activity except for N terminal, and thus the protein in question has a structure soluble to water except for the secretory signal at N terminal. Accordingly, it was found that 26·29 kDa protease is a water-soluble secretory protein, a trait which is commonly observed among many other cathepsin-like cysteine proteases. As one example showing such trait, FIG. 15 shows the hydropathy profile from the precursor of a cathepsin L of flesh fly.

From above observations, it was concluded that the two subunits of 26·29 kDa protease about which above findings were obtained are not encoded by two different genes, but encoded as a cluster or a precursor by a single gene. As this precursor protein, except for the region for 26 kDa subunit, has a structure typical of a cathepsin L-like protease precursor, it was concluded that 26·29 kDa protease precursor has a novel structural 26 kDa subunit inserted between a secretory signal of the cathepsin L-like protease precursor and a pro-sequence. Further, it was presumed that 26·29 kDa protease isolated and purified from body fluid cells is an adult type protease which results after two subunits separated in the precursor protein have been cleaved and joined together (FIG. 16).

Of cysteine proteases that join, from one precursor, a protease subunit and another subunit which has a structure clearly distinct from that of a protease, there is scarcely any other example than the one here concerned, except for a single example of cathepsin C. Cathepsin L is a cysteine protease like cathepsin L, and has a similar structure to that of 26·29 kDa protease: it has a novel subunit inserted between a secretion signal and a pro-sequence (Nikawa, T., et al. (1992) Eur. J. Biochem. 204, 381–393; Dolenc, I., et al. (1995) J. Biol. Chem. 270, 21626–21631), and the subunit is kept linked to the protease subunit even after processing.

Cathepsin C has been hitherto cloned from rats, humans, and schistosomes (Ishidoh, K., et al. (1991) J. Biol. Chem. 266, 16312–16317; Paris, A., et al. (1995) FBBS Lett. 369, 326–330; Butler, R., et al. (1995) Protein Rept. Let. 2. 313–320), and these three kinds of cathepsin C proteins have a conserved sequence within the novel subunit. The 26·29 kDa protease does not have the same conserved sequence. Further, although each of the three kinds of cathepsin C has a length of about 460 amino acids, the precursor of 26·29 kDa protease has a length of 550 amino acids, being different in length from the former by 90 amino acids. From this it was concluded that 26·29 kDa protease is not cathepsin C, but a novel bimolecular cysteine protease hitherto unknown.

What is most interesting with respect to the structure of the precursor of 26·29 kDa protease of this invention is this: although structurally the sequence behind 26 kDa subunit (towards C terminal) is apparently the precursor of a cathepsin L type protease, 26 kDa subunit has no homology with known proteases. To put it otherwise, the structure of these proteins may be of a chimera type consisting of cathepsin L or a basic enzyme (or its precursor) universally shared by many organisms, and of 26 kDa subunit or a protein having a quite new structure. The fact that 26·29 kDa protease has such a structure as described above suggests that the responsible genes may come into being through following processes: a sequence coding for 26 kDa subunit was introduced into an ancestor gene resembling the gene coding for cathepsin L, or conversely a gene coding for 26·29 kDa protease lost a sequence coding for 26 kDa subunit to give birth to the gene for cathepsin L.

As described above, it becomes evident that 26·29 kDa protease is structurally similar to various proteases belonging to cathepsin L family. Generally, a protease of cathepsin L family, although it actively hydrolyzes Z-Phe-Arg-MCA (Z=carbobenzoxy), scarcely hydrolyzes Z-Arg-Arg-MCA.

This has been demonstrated for cathepsin L from mammals including human, rat and mouse, cathepsin L from flesh fly, papain, and cathepsin C (Methods in Enzymology 80, 536–543; Khouri, H. E., et al. (1991) Biochemistry 30, 8929–8936; Nikawa, T., et al. (1992) Eur. J. Biochem. 204, 381–393). By contrast, cathepsin B from mammals hydrolyzes both of Z-Phe-Arg-MCA and Z-Arg-Arg-MCA. No other cysteine protease has been known to have a property to actively hydrolyze Z-Arg-Arg-MCA, and it has been believed that digestion of Z-Arg-Arg-MCA is characteristically observed in cathepsin B.

Table 2 lists specific activities of 26·29 kDa protease, cathepsin B from flesh fly and cathepsin L from flesh fly to various substrates, which were measured in terms of their hydrolytic activities against the fluorescence-attached synthetic substrates. The numeral represents the mass of fluorescent synthetic substrate hydrolyzed by a unit weight of protease, or a specific activity of that enzyme. For the numerals of Table, one unit of activity is defined as a weight of enzyme necessary for hydrolyzing 1 μmol of substrate in 10 minutes. "ND" in Table represents no result because the test not being made. Sequence listing numbers for sequences in Table 2 are: SEQ ID NO:100 and SEQ ID NO:101.

TABLE 2

| | Activity (units/mg enzyme) | | |
|---|---|---|---|
| Substrate | 26 · 29 kDa protease | cathepsin B | cathepsin L |
| z-Arg-Arg-MCA | 4.29 | 0.86 | 0.17 |
| z-Phe-Arg-MCA | 2.25 | 20.6 | 180 |
| Suc-Leu-Leu-Val-Tyr-MCA | 0.03 | 18.7 | 0.04 |
| Boc-Val-Leu-Lys-MCA | 0.61 | ND | ND |
| Suc-Ala-Pro-Phe-MCA | 0.01 | 0.83 | ND |
| Suc-Ala-Ala-Pro-Phe-MCA | 0.01 | 0.5 | ND |
| Pyr-Gly-Arg-MCA | 0.03 | 0.29 | ND |
| Boc-Phe-Ser-Arg-MCA | 0.15 | ND | ND |

The 26·29 kDa protease, unlike cathepsin L from flesh fly, well hydrolyzes Z-Arg-Arg-MCA. Further, it has also a hydrolyzing activity against Z-Phe-Arg-MCA, and thus this protease has a substrate-specificity similar to that of cathepsin B. From this result, it was found that 26·29 kDa protease, although its subunit or 29 kDa subunit is structurally close to cathepsin L, in its substrate specificity more closely resembles cathepsin B, and thus this protease is novel not only in structure but in activity.

Although cathepsin L from flesh fly is structurally close to 29 kDa subunit of 26·29 kDa protease, it practically does not hydrolyze Z-Arg-Arg-MCA as distinct from 29 kDa subunit. From this it was assumed that 26·29 kDa protease owes its enzymatic activity to its own specific structure. Namely, of all the structural components of 26·29 kDa protease, certain parts differently structured from cathepsin L may be responsible for the hydrolysis of Z-Arg-Arg-MCA. The specific structures possibly responsible for the characteristic enzymatic activity of 26·29 kDa protease may be principally accounted for by two factors: one is the presence of 26 kDa subunit and the other is the different amino acid sequence from that of cathepsin L.

Although 26·29 kDa protease well hydrolyzes Z-Arg-Arg-MCA, cathepsin B from flesh fly scarcely hydrolyzes Z-Arg-Arg-MCA (see Table 2)(Kurata, S., et al. (1992) Eur. J. Biochem. 204, 911–914; Takahashi, N., et al. (1993) FEBS Lett. 334, 153–157).

Generally, cathepsin B hydrolyzes Z-Arg-Arg-MCA, by binding a positive charge of glutamic acid located close to C terminal to a negative charge of arginine adjacent to Z (Khouri, H. E., et al. (1991) Biochemistry 30, 8929–8936; Hasnain, S. et al. (1993) J. Biol. Chem. 268, 235–240; Bromme, D. et al. (1994) J. Biol. Chem. 269, 30238–30242).

Therefore, the glutamic acid in question is conserved in various cathepsin B members (FIG. 17).

Chart 6, Sequence listing numbers for sequences in FIG. 17.

| Flesh fly 242 | SEQ. ID NO. 81 |
| mouse 239 | SEQ. ID NO. 82 |
| rat 239 | SEQ. ID NO. 83 |
| bovine 239 | SEQ. ID NO. 84 |
| human 239 | SEQ. ID NO. 85 |

-continued

| chicken 240 | SEQ. ID NO. 86 |
| tobacco 236 | SEQ. ID NO. 87 |

(Khouri, H. E. et al. (1991) Biochemistry 30, 8929–8936). By contrast, with cathepsin B from flesh fly, the glutamic acid is substituted for alanine, and thus the enzyme can not hydrolyze Z-Arg-Arg-MCA (Takahashi, N., et al. (1993) FEBS Lett. 334, 153–157).

Although cathepsin B from flesh fly can not hydrolyze Z-Arg-Arg-MCA, it hydrolyzes Suc-Leu-Leu-Val-Tyr-MCA (Suc=succinyl) that is indigestible to cathepsin B from mammals (Kurata, S. et al. (1992) Eur. J. Biochem. 204, 911–914). This substrate is originally one of the substrates that are digestible to chymotripsin. Cathepsin B is discharged by the body fluid cells into the body fluid while a flesh fly exists as a pupa or a stage at which it transforms from a third-instar larva to an adult, and it digests body fats or remnant of larva tissues left as a waste after metamorphosis. For the waste to be digested, what is needed is this chymotripsin-like activity (Kurata, S., et al. (1990) Insect Biochem. 20, 461–465; Kurata, S., et al. (1992) Dev. Biol. 153, 115–121). Cathepsin B has been thought heretofore as a lysosome enzyme, but cathepsin B from flesh fly has a function to act as a secretory enzyme, and thus achieves a function exceeding in importance that achieved by a mere lysosome enzyme. From above results it seems plausible to assume that in the flesh fly cathepsin B has taken a different course in evolution from that taken by cathepsin B of mammals, and, in association, its substrate-specificity comes to have a different character from that of the latter.

The above results can be summarized as follows: with the flesh fly, cathepsin B evolves such that it loses a trait necessary for hydrolyzing Z-Arg-Arg-MCA, while, as a compensation for that loss, 26·29 kDa protease or a cathepsin L-like enzyme acquires a trait necessary for hydrolyzing Z-Arg-Arg-MCA. To substantiate above hypothesis, however, it is necessary to demonstrate that the hydrolyzing activity of 26·29 kDa protease towards Z-Arg-Arg-MCA is used for the same purpose as in the corresponding hydrolyzing activity of cathepsin B of other animal species towards the same substrate. The biological significance of the hydrolyzing activity of 26·29 kDa protease towards Z-Arg-Arg-MCA is not known yet, but in this connection it is interesting to note that, according to the suggestion offered by Katsunuma et al., cathepsin B may be involved in phagocytosis or disposal of cellular waste, because, in mammalian cells, cathepsin B is located more preferably to outer lysosomes than cathepsin L, and because it exists at a higher concentration in an activated macrophage. The 26·29 kDa protease is also secreted as a response to the intrusion by foreign substances, and thus its hydrolyzing activity towards Z-Arg-Arg-MCA may be utilized for the digestion of such foreign substances.

The most conspicuous structural difference between 26·29 kDa protease and cathepsin L is that the former contains 26 kDa subunit while the latter does not. To further inquire into the role played by 26 kDa subunit in the protease activity of 26·29 kDa protease, the present inventor tried to assay the protease activity of 29 kDa subunit alone. For this purpose, a recombinant protein of 29 kDa subunit was prepared.

Figure 18:
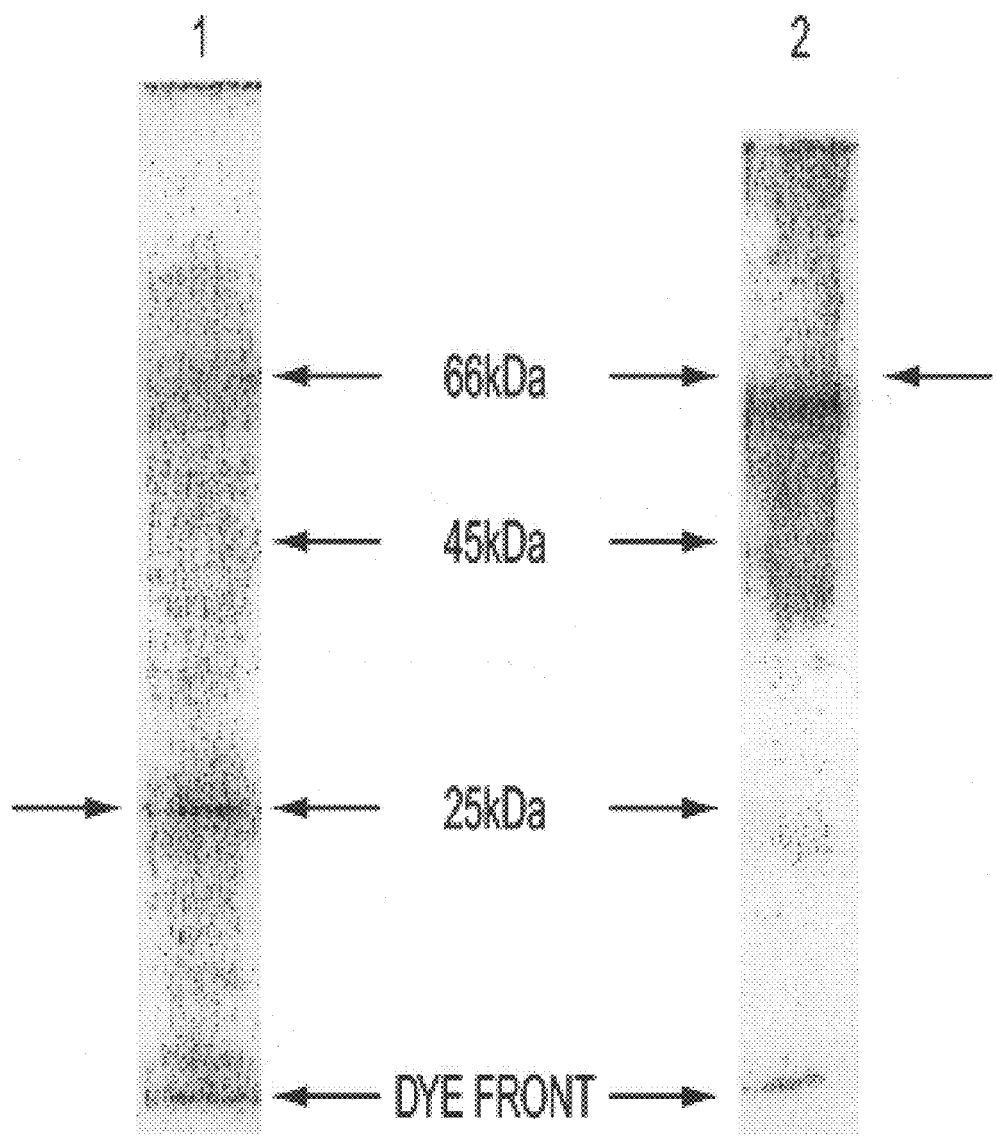
FIG. 18 is a drawing showing the electrophoretic analysis results of the precursor of a recombinant 26·29 kDa protease, and of a recombinant 29 kDa subunit.

For expression, E. coli was used. As a consequence, principally 25 kDa protein was expressed on SDS-PAGE (FIG. 18). The amino acid sequence from N terminal of this protein was completely correspondent with that of 29 kDa subunit except that the first residue was methionine, and thus it was concluded that a recombinant gene of 29 kDa subunit was successfully prepared.

The recombinant homologue of 29 kDa subunit has a molecular weight of 25dDa when measured on SDS-PAGE, which is different from the molecular weight (29 kDa) of 29 kDa subunit of 26·29 kDa protease isolated from the body fluid cells.

The molecular weight of 29 kDa subunit becomes 24.6 kDa when calculated on the basis of an amino acid sequence expected from the sequence of c DNA; 29 kDa subunit contains one asparagine to which an N type sugar chain may be bound; and 29 kDa subunit obtained from a natural source gives a vague band like a smear when extended by SDS-PAGE and later submitted to CBB staining, in contrast with the recombinant homologue of 29 kDa subunit which gives a sharp band. The three points described above suggest that the difference in molecular weight may be accounted for by the inclusion of a sugar chain within the naturally obtained 29 kDa subunit.

Practically all of the expressed 29 kDa subunit could be recovered as inclusion bodies which precipitate when submitted to a centrifugation of 10,000 g. A homogenate from the expressed E. coli cells was assayed for the protease activity towards Z-Arg-Arg-MCA, but it showed an activity only as much as the control E. coli cells into which were introduced plasmids with no insert. Thus, the recombinant homologue of 29 kDa subunit was not expressed in a form capable of exercising a protease activity.

This is probably because the recombinant homologue of 29 kDa subunit could not take a proper conformation necessary for the protease activity, as far as judged from the observation that the majority of expressed proteins form inclusion bodies. Many recombinant homologues of cysteine protease prepared through E. coli cells did not express a proper activity (Hasnain, S., et al. (1992) J. Biol. Chem. 267, 4713–4721). The only exception to this is a recombinant homologue of the precursor of human cathepsin L which, after being recovered from inclusion bodies, expresses a protease activity (Smith, S. M., et al. (1989) J. Biol. Chem. 264, 20487–20495). The present inventor put our recombinant homologue of 29 kDa subunit under the same condition which was effective for the recovery of activity for the above recombinant homologue, but could not recover its activity. During this trial, the present inventor used, as the control, 26·29 kDa protease isolated and purified from the body fluid cells of flesh fly. They denatured the control protease and later tried to recover its activity with no positive effects. From this it was concluded that the protease has to take a proper conformation to express its activity, and that the protease can not take that conformation of its own accord after it becomes a matured type enzyme, once it has undergone a processing.

In view of this, to examine whether the precursor of 26·29 kDa protease can take of its own accord the conformation necessary for activity, the present inventor prepared a recombinant protein of the precursor of 26·29 kDa protease.

The method was completely the same with that used for the preparation of a recombinant protein of 29 kDa subunit. In this case too, the expressed product forms inclusion bodies, and did not show an activity. The inclusion bodies were further treated so as to express an activity with no positive result. Thus, it was found that the recombinant protein from the precursor protein does not take a proper conformation of its own accord. For an active 26·29 kDa protease sample to be prepared, it may be necessary to reproduce a condition close to the physiological state.

FIG. 18 gives the SDS-PAGE profile of recombinant protein of the precursor of 26·29 kDa protease which has been purified from inclusion bodies. The protein in question has a molecular weight of 62 kDa on SDS-PAGE.

From this study using *E. coli* cells, following estimates were raised: the formation of inclusion bodies annihilated the possibility of the recombinant protein to act as an active protease; and to improve the experimental condition so that the activity may be expressed, it may be necessary to resort to yeast which will allow the expression of a secretory type protein; or alternatively to a baculovirus which will allow the expression of a recombinant protein under a more physiological condition.

In order to find the time when 26·29 kDa protease is put into action, the inventor sought the time when it expresses its activity.

(1) Northern Blotting Analysis

The expression time of m RNA coding for this protease was studied by Northern blotting analysis for the fresh flies at various developmental stages. To put it more specifically, RNA strands were sampled from an unfertilized egg, germ cell, larva, pupa and adult at various developmental stages, and examined.

Figure 19A:
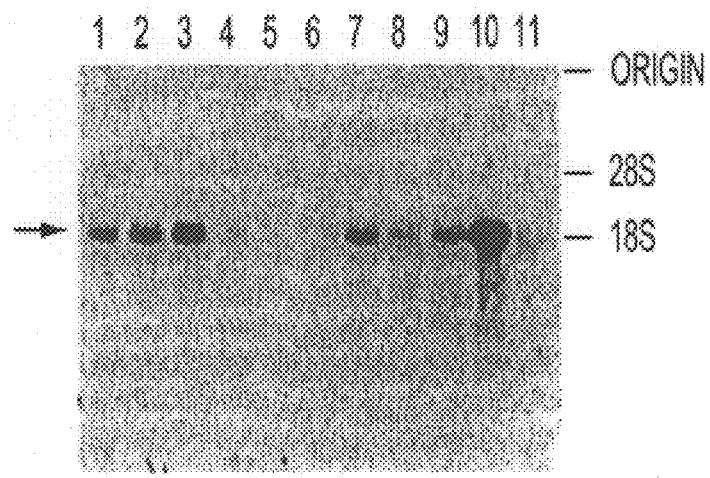
FIG. 19 is a drawing showing the expression of m RNAs coding for 26·29 kDa protease of Sarcophaga at its various development stages.
Figure 19B:
Figure 19C:

By the analysis a single band of about 2 kbp length was detected. This neatly corresponds with 1.9 kbp or the total length of c DNA which has been cloned above, and thus was assumed to be an m RNA coding for 26·29 kDa protease. It was found that this RNA strongly expresses itself when the test insect is at a stage between an unfertilized state and mid-term germination, or is a third-instar larva or a pupa. Thus it was assumed that this protease is active during development (FIG. 19). Further, only the band of about 2 kbp length was detected throughout the whole life of flesh fly, and thus it was concluded that what the m RNA for 26·29 kDa protease transcripts is expressed practically as a single product.

(2) Immunoblotting Analysis

As it was known that, for flesh fly cathepsin L and flesh fly cathepsin B, the m RNA coding for those proteins and the proteins themselves increase their concentrations temporarily during the development of a germ (Takahashi, N., et al. (1993) FEBS. Lett. 334, 153–157; Yano, T., et al. (1995) Eur. J. Biochem. 234, 39–43; Homma, K., et al. (1994) J. Biol. Chem. 269, 15258–15264), the change in concentration of 26·29 kDa protease during germination was also followed by immunoblotting.

While flesh flies were developing from an unfertilized state through fertilization until they become first-stage larvae, germs at each stage were sampled daily, and a homogenate was prepared from each sample. The homogenate, being 33 µg in terms of protein weight, was applied to SDS-PAGE, and 26·29 kDa protease was detected by immunoblotting (FIG. 20). The antibody used in this assay was highly specific against 26 kDa subunit. As a result it was found that 26 kDa subunit strongly expresses up to Day 2 after fertilization, but later subsides, that is, its expression shows a temporary rise during development.

From this observation it was confirmed that all the three cysteine proteases hitherto known, that is, cathepsin L, cathepsin B and 26·29 kDa protease undergoes a temporary rise in expression during development, and from this it was seen that these proteases are put into action during germination.

These three proteases have different substrate specificities as mentioned earlier, and thus it is possible for them to achieve a common object by executing different functions in a concerted manner. This hypothesis could be more validated, if it were possible to examine whether the maximally expressed times of the three proteases during germination are different from each other, and whether the locations of the three proteases are different from each other. Further, although it is still unknown whether the three proteases are intracellularly active like lysosome enzymes or they work as secretory type enzymes, it becomes increasingly evident that cathepsin L of flesh fly is secreted outside.

Further, to check whether 26·29 kDa protease or a novel protein of this invention is universally present in the animal world exceeding the boundaries between different species, like the previous cysteine proteases such as cathepsin L or cathepsin B, PCR was used so that isolation of a homologue of 26·29 kDa protease might be achieved.

First of all, isolation of a homologue of fruit fly (*Drosophila melanogaster*) or a species close to flesh fly (*Sarcophaga peregrina*) in evolution was tried. The primers for PCR included those depicted in FIGS. 4, 6, 7 and 8, and those introduced into the vector. They were used being combined as appropriate. A c DNA library (λZAP vector) prepared from the whole body of adult fruit fly served as the template. As a consequence, combinations of 26K3'-2 primer and SK primer of vector, of 26K3'-N primer and SK primer as depicted in FIG. 4 gave yields of about 330 bp and 280 bp respectively. These PCR yields were determined for their base sequences, and the thus obtained sequences revealed that the translation yield might be closely similar to the amino acid sequence of 26·29 kDa protease of flesh fly. However, the base sequence itself contains parts whose sequences are clearly distinct from the corresponding sequences of flesh fly, and thus the obtained sequence was assumed to represent a c DNA fragment coding for a homologue of 26·29 kDa protease of fruit fly. With this c DNA fragment as the template, PCR was applied to yield a longer fragment. The thus derived c DNA fragment was determined for its base sequence and the amino acid sequence expected from that base sequence was obtained, both of which are listed in FIGS. 21–24.

Chart 7, Sequence listing numbers for sequences in FIG. 23.

| flesh fly | SEQ. ID NO. 88 |
| fruit fly | SEQ. ID NO. 89 |
| cockroach | SEQ. ID NO. 90 |

Through the combined use of the same primers, PCR was attempted for a c DNA library from the fat body of adult cockroach (*Periplaneta americana*) as the template, to produce an amplified yield. This was determined for its base sequence which showed that the yield is also a homologue of the present protease (FIGS. 21–24).

The amino acid sequences of 26·29 kDa protease extracted from flesh fly, fruit fly and cockroach, and the base sequences coding for them are listed in Sequence Listing SEQ ID NOs. 1, 3 and 5, and 2, 4, 6 and 7 respectively. The sequences listed under SEQ ID Nos. 6 and 7 represent the base sequences of 26·29 kDa of cockroach, and the base sequence in the middle is still unknown and awaits a further study for its elucidation.

With a view to further examine the same protease among other animal species than the insect, isolation of a homologue from an earth worm (*Eisenia foetida*) belonging to the annelida family was attempted. The annelida represents a group of invertebrates positioned, from an evolutionary point of view, close to the insect. It was found that a number of combinations of primers yielded amplified samples, all of which showed a high similarity to cathepsin L. Thus, it was concluded that in this trial cathepsin L of earth worm was amplified, and a homologue of 26·29 kDa protease of earth worm was not obtained. With a view to further examine the same protease among vertebrates, besides those from invertebrates, PCR was applied to c DNA from mouse but a homologue of 26·29 kDa protease could not be obtained.

From these results it was found that 26·29 kDa protease is demonstrated in the inset undergoing incomplete metamorphosis such as cockroaches as well as in the insect undergoing complete metamorphosis such as flies, and that this protease can be taken as a newly found cysteine protease widely conserved in the insect world. Further, from these results it was presumed that this protease may come into being at a time when the insect group undergoing complete metamorphosis were separated from the insect group undergoing incomplete metamorphosis, or about three hundred millions years ago.

A comparison of the amino acid sequences of 26·29 kDa protease homologues from flesh fly, fruit fly and cockroach showed that the aforementioned four domains are conserved in all of the three homologues (FIG. 24). The 26 kDa subunit characteristic with this protease is quite similar not only in its amino acid sequence but also in its length among the three homologues, suggesting that its structure is also stably conserved. From this it was inferred that 26 kDa subunit is not a mere, random extension of pro-sequence, but rather a significant structure. Namely, 26 kDa subunit may play some important role for helping the protease to achieve its own specific function.

In addition to above, 26 kDa subunit conserves asparagine which can bind to an N type sugar chain (FIG. 24), and cysteines at the first and second positions from N terminal (FIG. 24). The two cysteines may be possibly used for disulfide bonds. Further, 26 kDa subunit has a sequence of about 40 residues whose structure is well conserved (FIG. 24).

As bimolecular cysteine proteases other than 26·29 kDa protease, cathepsin C and calpain have been known. The present inventor compared 26·29 kDa protease with calpain for their structural similarity, and found that the aforementioned well conserved region of about 40 residues closely resembles a certain region of the enzyme domain of calpain (FIG. 25).

Chart 7, Sequence listing numbers for sequences in FIG. 25.

|  |  |
|---|---|
| 26 kDa flesh fly | SEQ. ID NO. 91 |
| 26 kDa fruit fly | SEQ. ID NO. 92 |
| 26 kDa cockroach | SEQ. ID NO. 93 |
| calpain human | SEQ. ID NO. 94 |
| calpain rat | SEQ. ID NO. 95 |
| calpain chicken | SEQ. ID NO. 96 |
| calpain fruit fly | SEQ. ID NO. 97 |
| calpain nematode | SEQ. ID NO. 98 |
| calpain fluke | SEQ. ID NO. 99 |

This region of calpain is well preserved in the calpain homologues extracted from various animal species. Calpain is a cysteine protease which is present in the cytoplasm, varies its activity dependent on the concentration of calcium, and has been thought to be involved in information transmission. Calpain is a bimolecular protease, but, unlike 26·29 kDa protease, the two subunits are encoded by two different genes.

Next, the present inventor identified the loci of genes coding for 26·29 kDa of fruit fly. The fruit fly is an organism whose genetics has been intensively studied and thus the function of its genes has been elucidated by various genetic methods. With a view to elucidate the physiological function of 26·29 kDa protease by the genetic method, the present inventor determined the loci of its gene on a chromosome.

A c DNA fragment coding for 26·29 kDa protease of fruit fly labeled with digoxygenin was hybridized with the salivary gland chromosomes from a third stage larva of fruit fly, and anti-digoxygenin antibodies coupled with alkaline phosphatase were applied to the hybrid for detection. As a consequence, as indicated by an arrow (blue) in FIG. 26, a single band was detected on L arm of the third chromosome, and the locus in question was determined to be 70C through inspection of the stripe pattern of the chromosome. It was established that the gene for cathepsin L of fruit fly resides at locus 50C of R arm of the second chromosome (indicated by another arrow (red) of FIG. 26) (Matusmoto, I., et al. (1955) Eur. J. Biochem. 227, 582–587), and thus it was found that the two genes are located at different loci apart from each other.

For the function of 26·29 kDa protease to be analyzed, it is necessary to obtain an insect in which only the gene for this protease has been specifically mutated. To date a wide variety of mutants have been reported for the fruit fly. Of those mutants there are many for which no DNA level analysis has been made, but if it were revealed that the gene for 26·29 kDa protease is deleted or modified in one of those mutants, that mutant would serve for elucidation of the function of the protease in question.

In another aspect, because the gene for 26·29 kDa protease is determined to be located at 70C, it becomes possible to prepare a library including the genomic fragment adjacent to 70C, and, by cloning the fragment, to determine the structure of a gene coding for 26·29 kDa protease and its transcription control area. In vivo expression of an anti-sense RNA for 26·29 kDa protease or for dominant negative type 26·29 kDa protease in a fruit fly specifically inhibits the expression of 26·29 kDa protease, and thus it will be useful for analysis of the function of the protease in question. Further, it will be possible to examine in detail the transcription onto m RNA for the expression of 26·29 kDa protease by allowing GFP or Lac Z to express in vivo under the command of this transcription control area, and thus to determine on what part of the body this protease exerts its effect.

This invention will be illustrated more concretely below by means of examples, but the present invention should not be limited to those examples.

EXAMPLE 1 (Organisms)

The flesh fly was fed by the method provided by Otaki, et al. The flies were fed on sugar, water and dry milk at 27° C. The larvae were fed on pig liver. Third stage larvae were removed from liver, collected, washed, and kept in a plastic container filled with a small volume of water.

EXAMPLE 2 (Collection of blood cells)

The head of third stage larvae of flesh fly was cut off with sharp scissors, the body fluid was collected into a tube, and the fluid was stored being cooled with ice. Collection of blood cells was performed by centrifuging the body fluid at 100 g at 4° C. for five minutes, and the thus obtained blood cells were washed with physiological saline for insects (130 mM NaCl, 5 mM KCl and 1 mM CaCl2), and stored at −80° C. Example 3 (Partial purification of 26·29 kDa protease) Blood cells collected from 180 ml of body fluid were homogenized in insect saline containing 0.1% TritonX-100, and the homogenate was centrifuged at 16,000 rpm at 4° C. for 15 minutes. The supernatant was further centrifuged at 18,000 rpm at 4° C. for 15 minutes. The supernatant was diluted 10 fold with addition of buffer A (20 mM sodium acetate buffer (pH 5.0) containing 1 mM EDTA), and the diluted solution was transferred into a DEAE-sephalose CL6B (1.5×7 cm, Pharmacia Biotec) and allowed to equilibrate with buffer A. The adsorbed substance was eluted with a linear gradient of 0–200 mM NaCl as a background. Each fraction was assayed for its protease activity, and the protein content thereof was determined by SDS-PAGE.

EXAMPLE 4 (Assay of protease activity)

Assay of enzymatic activity was performed using 0.2 ml of 5 mM sodium phosphate (pH 6.0) containing 0.05 mM peptidyl-MCA substrate, 100 mM NaCl, 1 mM EDTA, 5 mM 2-mercaptoethanol, and 10 μl of the test fraction. The solution was incubated at 27° C. for 10 minutes, to which was added 0.2 ml of 20% aqueous solution of acetic acid to stop the reaction. Fluorescence at 380 nm and 460 nm was observed. The amount necessary for hydrolyzing 1 μmol substrate in 10 minutes under the above condition was defined as one unit of protease activity.

For purification of 26·29 kDa protease, carbobenzoxy-Arg-Arg-MCA was used as the substrate. Further, for determination of substrate specificity, various peptidyl-MCAs were used.

EXAMPLE 5 (Purification of 26 kDa and 29 kDa subunits)

Partial purification of 26·29 kDa protease was performed using 12.5% SDS-polyacrylamide gel electrophoresis. The yield was submitted to CBB staining and washed with distilled water, and the bands containing 26 kDa and 29 kDa bands were cut and removed from gel. These gel strips were allowed to equilibrate with SDS-PAGE sample buffer until their color turned from dark blue to light blue, and transferred into a dialysis bag containing the same volume of SDS-PAGE sample buffer. The dialysis bag containing the gel strips were fixed on the plate of SDS-polyacrylamide gel, and the proteins in the gel strips were eluted by electrophoresis. The voltage and electric current used were the same as in SDS-PAGE. The eluted protein was collected in a micro-centrifugation tube with a capacity of 1.5 ml, and dried. One ml of ethanol was added to the dried protein sample, incubated at 60° C., and centrifuged at 10,000 g. The supernatant was discarded, and the thus obtained precipitate was dried, dissolved in 50 mM Tris/HCl (pH 9.0) to serve as a sample to digest proteins. Example 6 (Digestion of proteins by purified 26 kDa and 29 kDa subunits).

Each of purified 26 kDa and 29 kDa subunits was dissolved in 50 mM Tris/HCl (pH 9.0), and was incubated at 30° C. for 20 hours together with lysyl-end-peptidase or arginyl-end-peptidase. The ratio of enzyme against substrate was 1/50 (weight/weight). After incubation, resulting peptides were submitted to reverse phase HPLC (4.6×250 mm reverse phase synchro-pack RP-P (C18) column, Gilson HPLC System) and was eluted at a rate of 1 ml/min for 60 minutes against a linear gradient of 0–60% acetonitryl in the presence of 0.05% TFA. The eluted peptides were monitored with rays of 220 and 280 nm. The fractions containing the peptides under study were dried under a reduced pressure, dissolved in 10 μl of aqueous solution of acetonitryl and had their sequences automatically analyzed with a protein sequencer (Shimadzu PPSQ-10).

EXAMPLE 7 (PCR amplification of c DNA fragment coding for 26 kDa subunit)

The c DNA in question was amplified by PCR. Designing of oligonucleotide primers was based on the amino acid sequences of partial peptides of 26 kDa subunit (FIG. 4). The template used for the first stage amplification included a phage DNA extracted from a c DNA library of a third stage larva of flesh fly. The template used for the second stage amplification consisted of the PCR yield obtained through the first stage amplification which had been diluted 100 fold. The amplification condition consisted of a repetition of 30 cycles each comprising warming at 94° C. for 30 seconds, cooling at 45° C. for 30 seconds and rewarming at 72° C. for 60 seconds. The yield by PCR was submitted to agarose electrophoresis for analysis.

The PCR yield obtained by the second stage amplification was ligated to a PCR II vector by means of a Takara ligation kit, and the vector was introduced into competent E. coli cells of the strain JM109 (Takara). The cells were plated on an LB agar plate containing 100 μg/ml of ampicillin. The insert positive clone was isolated by PCR where an M13 forward primer and M13 reverse primer were used. From the insert positive clone was extracted the plasmid.

The DNA sequence of insert was determined.

EXAMPLE 8 (Agarose gel electrophoresis)

Electrophoresis of the DNA was performed on a gel plate soaked with agarose 1600 (Wako) and AGE buffer. The composition of AGE buffer included 40 mM Tris/acetic acid (pH 8.0), 2 mM EDTA and 5 mM sodium acetate. This buffer was also used as an electrode buffer. After electrophoresis, the plate was stained with ethyl bromide so that bands could be detected, which were then photographed.

EXAMPLE 9 (DNA sequencing)

Determination of the DNA sequences was performed by the Sanger's dideoxy chain termination method which employed an AB1373A DNA sequencer prepared in accordance with a tack dideoxy terminator cycle sequencing kit (Applied Biosystems). The sequence of double-stranded nucleotides was determined. For determination of the sequence of c DNA, the plasmid was purified through alkaline lysis. For direct determination of the sequence of PCR yields, isolated DNA fragments were purified with SUPREC 02 (Takara).

EXAMPLE 10 (Colony hybridization)

Construction of a c DNA library of the adult primodium of a third stage larva of flesh fly was achieved by the use of a gigapack in-vitro packaging kit (Stratagene) and a λZAP II c DNA synthesis kit (Stratagene). Colonies comprising E. coli cells of SOLR strain which had been transformed by a recombinant pBluescript (Stratagene) were transferred to a replication set consisting of a nylon filter. These colonies were submitted to screening for which a DNA probe was used.

Production of the probe was achieved by PCR where a 26K5'-2 primer and 26K3'-1 primer (see FIG. 4) were used in the presence of [α-32P] d CTP. The template included a plasmid containing a DNA fragment which had been amplified by PCR where 26K5'-2 and 26K3'-1 primers were used.

EXAMPLE 11 (Isolation of c DNA coding for 26·29 kDa protease of Sarcophaga)

Colonies comprising SOLR strain E. coli cells which had been transformed by pBluescript (Stratagene) were screened by PCR. Positive clones were concentrated by limiting dilution.

EXAMPLE 12 (Mass analysis)

The purified 26·29 kDa protease was denatured with 6M guanidine/HCl, and submitted to HPLC (4.6×250 mm reversed phase synchro pack RP-P (C18) column, Gilson HPLC System) whereby it was eluted at a rate of 1 ml/min for 60 minutes against a linear gradient of 0–60% acetonitryl in the presence of 0.05% TFA. The purified 26 kDa subunit was submitted to a meter MALD1-MS (MALDI-IV, Shimadzu/Klatoscompact) with BSA as a molecular weight standard. The matrix used included α-cyano-4-hydroxy-cinnamic acid (CHCA).

EXAMPLE 13 (Expression of the recombinant protein)

(i) Recombinant 29 kDa subunit

For preparation of an insert DNA, the c DNA region coding for 29 kDa subunit of 26·29 kDa protease of Sarcophaga was amplified by PCR where a recombinant 29K5' primer (5' ccacatatgGACACAGTGCCAGATCAAT 3') and a recombinant 26<29K3' primer (5' ccctcgagTTACATCTC-TACATAAGTGG 3'), and a pfu polymerase were used. The amplified DNA was purified through phenol extraction, and digested at 37° C. overnight by Ndel and Xhol. The digested DNA was submitted to 2% agarose gel electrophoresis incorporating GTG agarose, and stained with ethyl bromide. Bands are removed from the gel, and submitted to SUPREC01 (Takara) so that DNA strands were extracted therefrom. For preparation of a vector DNA, a plasmid p ET17b was digested at 37° C. overnight by Ndel and Xhol. The digested plasmid DNA was separated by 1.5% agarose gel electrophoresis, and stained with ethyl bromide. Bards are removed from the gel, and submitted to GENECLEAN III (Bio 101) for extraction of DNA.

Ligation of the purified insert and vector was achieved by the use of a Takara ligation kit (second version), and the resulting vector was introduced into competent *E. coli* cells of JM109 strain (Takara) which were then placed on an LB agar plate containing 100 μg/ml of ampicillin. Insert positive clones were isolated by PCR screening where a T7 promoter primer and seq A-B primer were used. The DNA sequence of insert was determined, but no mutant was observed. The plasmid was introduced into competent *E. coli* cells of BL21 strain (Novagen) which were then placed on an LB agar plate. One clone was removed and allowed to grow on 5 ml of LB medium. It was cultivated until the OD600 of IPTG became 0.6 so that the expression of recombinant protein could be induced. The expression of recombinant 29 kDa subunit was checked as follows. Bacteria were recovered by centrifugation, dissolved/separated in 1% SDS and 2% 2-mercaptoethanol and submitted to SDS-PAGE. Purification of a recombinant 29 kDa subunit consisted of collecting bacteria from 40 ml of medium, dissolving/separating cell elements by means of a supersonic wave, and collecting inclusion bodies by centrifugation. The inclusion bodies were dissolved in 6M urea in 30 mM Tris/HCl (pH 7.4) and separated by DEAE-TOYOPEARL column chromatography. The purified 29 kDa subunit was analyzed by SDS-PAGE.

(ii) Recombinant 26·29 kDa protease precursor

The necessary steps were practically the same as described in (I) except that a recombinant 26K5' (5' aaa-catatgACAAATCCACCACGCTGGG 3') and a recombinants 26, 29K3' were used as primers. The expressed proteins were recovered from inclusion bodies by centrifugation, washed five times with 1OmM Tris/HCl (pH 8.0) containing 1 mM EDTA, and submitted to SDS-PAGE for analysis.

EXAMPLE 14 (Northern blotting)

RNA blot hybridization dependent on the use of 50% (v/v) formamide, 5× SSPE, 5× Denhard's solution, 50 mM phosphate buffer, 1% SDS, and single strand sermon sperm DNA solution (200 μg/ml) was allowed to proceed at 42° C. for 16 hours. The yield was filtered, and washed at room temperature and 50° C. each time for 10 minutes with 0.1× SSC containing 0.1% SDS. The filtrate was submitted at −80° C. to autoradiography. A DNA fragment used as the probe was obtained by PCR where a recombinant 29K5' primer and a recombinant 26, 29K3' primer were used. The probe was labeled with [α-32P]d CTP via a random primer labeling kit.

EXAMPLE 15 (Protein assay)

The protein was determined by the Lowery's method dependent on the use of bovine serum albumin.

EXAMPLE 16 (Immunoblotting analysis)

The sample was submitted to SDS-PAGE, and isolated proteins were transferred by electrophoresis to a polyvinylidene difluoride membrane filter. The filter was placed in 5% skim milk solution for one hour, transferred to a rinse solution [10 mM Tris/HCl (pH 7.9) containing 150 mM NaCl, 1 mM EDTA, 0.1% (volume) Triton X-100 and 0.25% skim milk] containing anti-26·29 kDa protease antibodies, and allowed to stand at 4° C. overnight. The yield was washed thoroughly with the rinse solution, and submitted to autoradiography for which a Kodak XAR film was used.

EXAMPLE 17 (PCR amplification of 26·29 kDa proteases from fruit fly and cockroach)

Amplification of a c DNA fragment for 26·29 kDa protease of fruit fly was performed by using a c DNA library for the whole adult body of flesh fly of Canton S strain as the template. Amplification of a c DNA fragment for 26·29 kDa fragment of cockroach was performed by using a c DNA library for the whole fat body of cockroach as the template. The primer used was as depicted in the figure.

EXAMPLE 18 (Chromosome hybridization)

(i) Preparation of a third stage larva of fruit fly

Third stage larvae of fruit fly of Canton S strain were fed until they became third stage adults. This feeding condition was important for acquisition of large larvae having large salivary gland chromosomes.

(ii) Fixation of salivary glands

The salivary gland of the third stage larva of fruit fly dipped in 135 mM NaCl was removed under a microscope. The removed gland was immersed in 6 μl of 45% acetic acid for one minute and in lactic acid/DDW/acetic acid (1:2:3) for 12 minutes for fixation, and then covered with silicone-treated cover glass. Pressure was applied with a finger onto the fixed gland to crush it, and chromosomes were painted onto the cover glass. For further fixation, the specimen was kept at 4° C. for one to two days and nights. After fixation, the specimen was frozen with liquid nitrogen, and the cover glass was removed. The specimen was immersed in ethanol for five minutes, and then dried. The slide was kept at 4° C. until it was used for observation.

(iii) Labeling the probe with digoxygenin

A 1.5 kbp fragment of c DNA for 26·29 kDa protease was amplified by PCR where a Dros 26' 29K5'-2 primer and a 29K3'-2 primer were used, and purified by phenol extraction. A 250 ng of purified DNA was labeled with digoxygenin in a 100 μl scale reaction for which a DIG DNA labeling kit (Boehringer Mannheim) was used.

(iv) Hybridization

The slide was immersed in 0.07N NaOH for three minutes, in 2×SSC two times each for five minutes, in 70% ethanol two times each for five minutes, and in 100% ethanol for five minutes, and dried. The hybridization solution was dropped onto the tissue that had been fixed and denatured, and the tissue was covered with a new cover strip, sealed with a "top coat," and incubated overnight at 37° C. After hybridization, the top coat was removed, and the tissue was immersed in 6×SSC at room temperature for 10 minutes, in 2×SSC at 50° C. for 10 minutes, and in 1×SSC at 50° C. for 10 minutes.

(v) Detection of bands

The hybridizing probe was detected through a coloring reaction which took place after application of anti-digoxygenin antibodies carrying alkaline phosphatase and subsequent addition of a DIG detection kit (Boehringer Mannheim). Chromosomes stained dark blue were submitted to photography.

Next, Sequence Listings will be presented. In the Listings, amino acids are represented not by ordinary three-letter symbols, but by one letter symbols, and the symbols are separated not by ordinary one blank space but by two blank spaces. Undefined amino acids are represented by "x," instead of the symbol as formally used. Further, numbers to be attached to amino acids are given on the right side of amino acids rows, in stead of below tha amino acid rows as is the case with ordinary listing.

What is claimed is:

1. As isolated protein having the amino acid sequence as represented by Sequence Listing, SEQ ID NO. 3, and having a cysteine protease activity.

2. As isolated DNA having a nucleic acid sequence as represented by Sequence Listing SEQ ID NO. 4.

3. An isolated enzyme comprising a protein which has the amino acid sequence as represented by Sequence Listing SEQ ID NO. 3, and having a cysteine protease activity.

* * * * *